United States Patent [19]

Suzue et al.

[11] Patent Number: 5,244,892

[45] Date of Patent: Sep. 14, 1993

[54] CEPHEM COMPOUNDS, AND ANTIBACTERIAL AGENTS

[75] Inventors: Seigo Suzue, Kuki; Kikoh Obi; Tatsuhiro Saito, both of Nogi; Keiji Hirai, Washimiya; Hideyuki Fukuda, Utsunomiya, all of Japan

[73] Assignee: Kyorin Pharmaceutical Co., Ltd., Tokyo, Japan

[21] Appl. No.: 774,844

[22] Filed: Oct. 11, 1991

[30] Foreign Application Priority Data

Oct. 16, 1990 [JP] Japan .......................... HEI2-276852

[51] Int. Cl.$^5$ ................ C07D 501/20; A61K 31/545
[52] U.S. Cl. .................................... 514/206; 540/226; 540/227
[58] Field of Search ...................... 540/227, 226, 225; 514/206

[56] References Cited

U.S. PATENT DOCUMENTS

| | | |
|---|---|---|
| 3,904,618 | 9/1975 | Pioch . |
| 4,513,149 | 4/1989 | Megi et al. ............................ 540/227 |
| 4,546,176 | 10/1989 | Maduda et al. ...................... 540/227 |
| 5,057,511 | 10/1991 | Jung et al. ............................ 540/227 |

FOREIGN PATENT DOCUMENTS

| | | |
|---|---|---|
| 0003115 | 7/1979 | European Pat. Off. . |
| 0062328 | 10/1982 | European Pat. Off. . |
| 0251330 | 1/1988 | European Pat. Off. . |
| 0271064 | 6/1988 | European Pat. Off. . |
| 2287230 | 5/1976 | France . |
| 49-20319 | 5/1974 | Japan . |
| 57-165389 | 12/1982 | Japan . |
| 57-165390 | 12/1982 | Japan . |
| 58-72590 | 4/1983 | Japan . |
| 58-154588 | 9/1983 | Japan . |
| 63-264487 | 11/1988 | Japan . |

OTHER PUBLICATIONS

Journal of the American Chemical Society, 90:2, Jan. 17, 1968.
J. Org. Chem., vol. 35, No. 7, 1970.
J. Antibiotics, 38, 1738 (1985). Synthetic Communications, 16(9), 1029–1035 (1986).
Tetrahedron Lett., 22, 3915 (1985).
Chem. Pharm. Bull., 35, 3115 (1977).
Tetrahedron, 34, 725 (1978).
J. Natl. Pro., 53, 50 (1990).
JCS Perkin Trans I, 837 (1980).

*Primary Examiner*—Nicholas S. Rizzo
*Attorney, Agent, or Firm*—Oblon, Spivak, McClelland, Maier & Neustadt

[57] ABSTRACT

Novel cephem compounds represented by a formula [I] and pharmacologically admissible salts or capable of physiologically hydrolyzable nontoxic esters thereof are disclosed.

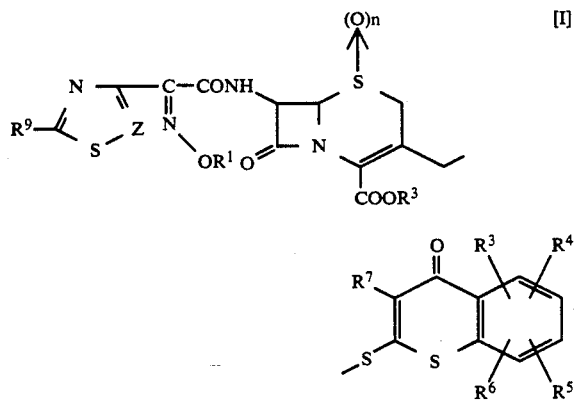

[wherein $R^1$ indicates a straight-chain or branched lower alkyl group, which may be substituted by carboxyl group which may be protected, trityl group, hydrogen atom or fluorine-substituted lower alkyl group, $R^2$ indicates a hydrogen atom, metal atom, protective group for carboxyl group or ester residue producible hydrolyzable ester in vivo, $R^3$, $R^4$, $R^5$ and $R^6$, which may be identical or different, indicate hydrogen atoms, halogen atoms, straight-chain or branched lower alkyl groups, which may be substituted, mercapto groups, which may be substituted, lower alkylamino groups, (Abstract continued on next page.)

hydroxyl groups, which may be protected, lower alkoxy groups, lower alkanoyl groups, lower alkoxycarbonyl groups, or lower alkylenedioxy groups, which may be substituted, being maybe formed with $R^3$ and $R^4$, $R^7$ indicates a hydrogen atom, cyano group, halogen atom or $COOR^8$ ($R^8$ is hydrogen or lower alkyl group), $R^9$ indicates an amino group, which may be protected, Z indicates N or CH, and n indicates 0 or 1].

Preparation processes for them and antibacterial agents containing them as effective ingredients are also claimed.

3 Claims, No Drawings

CEPHEM COMPOUNDS, AND ANTIBACTERIAL AGENTS

BACKGROUND OF THE INVENTION

The present invention relates to novel cephem compounds useful as antibacterial agents, salts permissible as medicinal drugs, preparation processes for them and further antibacterial agents having them as effective ingredients.

Cephalosporin type antibacterial agents exhibit a broad antibacterial activity against Gram-positive bacteria and Gram-negative bacterial and various cephasporin compounds have already been synthesized. Among these compounds, however, only few therapeutic agents exhibit the antibacterial activity against Pseudomonas aeruginosa and there is no agent which exhibits potent antibacterial effect broadly from Gram-positive bacterial including staphylococcus aureus to Gram-negative bacterial including Pseudomonas aeruginosa.

Moreover, compounds having the thiochromone skeleton in cephem are disclosed in Japanese Unexamined Patent Publication No. Sho 54-109995, No. Sho 57-165389 and No. Sho 57-165390 and U.S. Pat. No. 3,904,618. These link 2- or 3-position of thiochromone skeleton to part of 7-position side chain of cephem and, with respect to compounds having thiochromone skeleton at 3-position side chain of cephem, synthesis, to say nothing of disclosure and suggestion in specification are not made at all.

Since cephalosporin type antibacterial agents exhibit the selective toxicity only against bacteria and do not affect on the animal cells, they are broadly used for the therapy of infective diseases due to bacteria as antibiotics with less side-effects, thus they are drugs with high usefulness.

In recent, however, glucose-nonfermentable Gram-negative bacillus, in particular, Pseudomonas aeruginosa is often isolated from patients, whose immune power has decreased, as a inflaming bacterium for hard-to-cure infective diseases. On the other hand, in the Gram-positive bacteria, staphylococcus aureus (MRSA) resistant to overall antibacterial agents has clinically become a serious object of public concern.

From such situation, antibacterial agents being well-balanced against both Gram-positive bacteria including MRSA and Gram-negative bacteria including Pseudomonas aeruginosa and yet exhibiting potent antibacterial power are sought.

Aiming at providing novel cephalosporin derivatives having excellent antibacterial power, the inventors diligently studied on novel cephalosporin derivatives having 2-(2-aminothiazole-4-yl)-2-substituted-oxyiminoacetamide group or 2-(5-amino-1,2,4-thiadiazole-3-yl)-2-substituted-oxyiminoacetamide group at 7-position of cephem skeleton and unusual thiochromone skeleton at 3-position through sulfide linkage. As a result, a surprising fact has been found that the compounds of the invention have potent antibacterial activity against Gram-positive bacteria and Gram-negative bacteria, simultaneously have well-balanced road antibacterial spectra against up to Staphylococcus aureus (MRSA) and Pseudomonas aeruginosa resistant to overall antibacterial agents and yet increase also the antibacterial activity, leading to the completion of the invention.

Namely, the inventive compounds having 2-(2-aminothiazole-4-yl)-2-substituted-oxyiminoacetamide group or 2-(5-amino-1,2,4-thiadiazole-3-yl)-2-substituted-oxyiminoacetamide group at 7-position of cephem skeleton and (substituted-thiochromone-2-yl) thiomethyl group at 3-position are novel compounds never found in the literatures and have well-balanced broad spectra and potent antibacterial activity against from Gram-positive bacteria including MRSA to Gram-negative bacteria including Pseudomonas aeruginosa.

SUMMARY OF THE INVENTION

The invention relates to compounds represented by a general formula [I]

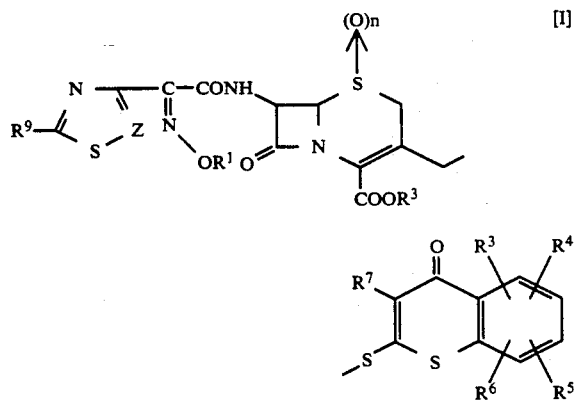

[wherein $R^1$ indicates a straight-chain or branched lower alkyl group, which may be substituted by carboxyl group which may be protected, trityl group, hydrogen atom or fluorine-substituted lower alkyl group, $R^2$ indicates a hydrogen atom, metal atom, protective group for carboxyl group or ester residue producible hydrolyzable ester in vivo, $R^3$, $R^4$, $R^5$ and $R^6$, which may be identical or different, indicate hydrogen atoms, halogen atoms, straight-chain or branched lower alkyl groups, which may be substituted, mercapto groups, which may be substituted, lower alkylamino groups, hydroxyl groups, which may be substituted, lower alkoxy groups, lower alkanoyl groups, lower alkoxycarbonyl groups, or lower alkylenedioxy group which may be substituted, $R^7$ indicates a hydrogen atom, cyano group, halogen atom or $COOR^8$ ($R^8$ is hydrogen or lower alkyl group), $R^9$ indicates an amino group, which may be protected, Z indicates N or CH, and n indicates 0 or 1], preparation processes therefor and antibacterial agents containing said compounds as effective ingredients.

DETAILED DESCRIPTION OF THE INVENTION

In following, explanation will be made about the symbols and terminologies described in this apecification.

The substituent $R^1$ in the compounds of general formula [I] means a straight-chain or branched lower alkyl group, which may be substituted by carboxyl group which may be protected, trityl group, hydrogen atom or fluorine-substituted lower alkyl group.

Here, the straight-chain or branched lower alkyl group indicates an alkyl group with carbon atoms of 1 to 6. Concretely, methyl group, ethyl group, n-propyl group, i-propyl group, n-butyl group, i-butyl group, sec-butyl group, t-butyl group, n-pentyl group, n-hexyl group, etc. can be mentioned and, as particularly preferable examples, for example, methyl group, ethyl group, n-propyl group and i-propyl group are mentioned.

As the fluorine-substituted lower alkyl groups, fluoromethyl group, difluoromethyl group, trifluoromethyl group, 2-fluoroethyl group, 2,2-difluoroethyl group, 2,2,2-trifluoroethyl group, 1-fluoroethyl group, 1,2-difluoroethyl group, etc. can be mentioned and, as particularly preferable examples, fluoromethyl group and 2-fluoroethyl group are mentioned.

As preferable examples for the substituent $R^1$ which may be substituted by carboxyl group, carboxymethyl group, 1-carboxy-1-methylethyl group, 1-carboxy-1-methylpropyl group and 1-carboxy-1-methylbutyl group are mentioned.

The substituent $R^2$ in the compounds of general formula [I] means a hydrogen atom, metal atom or ester residue producible hydrolyzable ester in vivo.

Here, as the metal atoms, alkali metals such as sodium and potassium and alkaline earth metals such as calcium and magnesium can be mentioned and, as preferable examples, sodium and potassium are mentioned.

As the ester residues producible hydrolyzable ester in vivo, lower alkoxycarbonyloxyalkyl group, alkanoyloxymethyl group, (2-oxo-1,3-dioxolene-4-yl)methyl group which may be substituted, etc. can be mentioned, and, as particularly preferable examples 1-(ethoxycarbonyloxy)-ethyl group, acetoxymethyl group, pivaloyloxymethyl group and 5-methyl-2-oxo-1,3-dioxolene-4-ylmethyl group can be mentioned.

The substituents $R^3$, $R^4$, $R^5$ and $R^6$, in the compounds of general formula [I], which may be identical or different, mean hydrogen atoms, halogen atoms, straight-chain or branched lower alkyl groups, which may be substituted, mercapto groups, which may be substituted, lower alkylamino groups, hydroxyl groups, which may be protected, lower alkoxy groups, lower alkanoyl groups, lower alkoxy carbonyl groups, or lower alkylenedioxy group, which may be substituted.

Here, as the halogen atoms, fluorine atom, chlorine atom, bromine atom and iodine atom are mentioned.

The straight-chain or branched lower alkyl group, which may be substituted, indicates an alkyl group with carbon atoms of 1 to 6, which may have substituent. Here, the substituent means an alkoxy group, halogen atom, hydroxyl group, which may be protected, and amino group, which may be substituted by lower alkyl group, lower acyl group, etc. As particularly preferable examples of lower alkyl group, which may be substituted, methyl group, ethyl group, n-propyl group, i-propyl group, n-butyl group, i-butyl group, sec-butyl group, t-butyl group, methoxymethyl group, ethoxymethyl group, 1-methoxyethyl group, 2-methoxyethyl group, fluoromethyl group, 2-fluoroethyl group, 1-fluoroethyl group, chloromethyl group, 2-chloroethyl group, 1-chloroethyl group, hydroxymethyl group, 2-hydroxyethyl group, 1-hydroxyethyl group, 1,2-dihydroxyethyl group, aminomethyl group, 2-aminoethyl group, 1-aminoethyl group, methylaminomethyl group, dimethylaminomethyl group, pyrrolidinylmethyl group and cyclopropylaminomethyl group are mentioned.

As particularly preferable examples of mercapto group, which may be substituted, methylmercapto group, ethylmercapto group, phenylmercapto group, (4-methyl-1,2,4-triazole-3-yl) mercapto group and (1-methyltetrazole-5-yl)mercapto group are mentioned.

The lower alkylamino group indicates an amino group substituted by alkyl group with carbon atoms of 1 to 6 and the substituent on N can form a ring. As particularly preferable examples of lower alkylamino group, methylamino group, dimethylamino group, ethylamino group, diethylamino group, cyclopropylamino group, n-propylamino group, i-propylamino group, pyrrolidinyl group, piperidinyl group, morpholinyl group, piperazinyl group and N-methylpiperazinyl group are mentioned.

The lower alkoxy group has a straight-chain or branched alkyl group with carbon atoms of 1 to 6. Concretely, methoxy group, ethoxy group, n-propoxy group, i-propoxy group, cyclopropoxy group, etc. can be mentioned and, as particularly preferable examples, methoxy group and ethoxy group are mentioned.

The lower alkanoyl group indicates a straight-chain or branched alkanoyl group with carbon atoms of 1 to 6 and, as particularly preferable examples, acetyl group and pivaloyl group are mentioned.

The lower alkoxycarbonyl group has a straight-chain or branched alkyl group with carbon atoms of 1 to 6 and, concretely, methoxycarbonyl group and t-butoxycarbonyl group are mentioned.

As particularly preferable examples of lower alkylenedioxy group which is formed with $R^3$ and $R^4$ and which may be substituted, methylenedioxy group, ethylenedioxy group and dimethylmethylenedioxy group are mentioned.

The substituent $R^7$ in the compounds of general formula [I] means a hydrogen atom, cyano group, halogen atom or $COOR^8$ ($R^8$ is hydrogen or lower alkyl group). Here, as the halogen atoms, fluorine atom, chlorine atom, bromine atom and iodine atom are mentioned. The lower alkyl group in this $COOR^8$ indicates an alkyl group with carbon atoms of 1 to 6. Concretely, methyl group, ethyl group, n-propyl group, i-propyl group, n-butyl group, sec-butyl group, t-butyl group, etc. can be mentioned and, as particularly preferable examples, methyl group and ethyl group are mentioned.

Moreover, for the partial structure

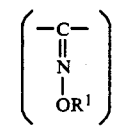

in the oxyimino group of general formula [I], there exist syn isomer

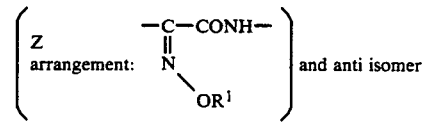

and anti isomer

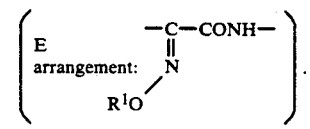

Generally, the syn isomer exhibits more excellent antibacterial activity, hence every $OR^1$ group is syn isomer in this specification. E/Z nomenclature is described in J. Am. Chem. Soc., 90, 509 (1968).

The compounds of general formula [I] can be converted to their pharmacologically permissible salts or physiologically hydrolyzable nontoxic esters by usual methods.

The nontoxic salts of the compounds of general formula [I] mean medicinally permissible common ones and salts of 4-position carboxyl group of cephem skeleton or carboxyl group in the substituent of group $R^1$ at 7-position of cephem skeleton, or salts in 2-amino-thiazole group or 5-amino-1,2,4-thiadiazole group at 7-position of cephem skeleton can be mentioned. Metal salts, for example, with sodium, potassium, calcium, magnesium, aluminum, etc., organic amine salts, for example, triethylamine salt, pyridine salt, ethanolamine salt, triethanolamine salt, etc., inorganic acid salts, for example, with hydrochloric acid, hydrobromic acid, nitric acid, sulfuric acid, perchloric acid, etc., organic acid salts with acetic acid, lactic acid, propionic acid, maleic acid, fumaric acid, malic acid, tartaric acid, citric acid, etc., sulfonic acid salts, for example, with methanesulfonic acid, isethionic acid, p-toluenesulfonic acid, etc., amino acid salts with glutamic acid, aspartic acid, lysine, arginine, etc., and the like can be mentioned.

The nontoxic esters of general formula [I] mean medicinally permissible common ones at 4-position carboxyl group of cephem skeleton and alkanoyloxymethyl group, for example, acetoxymethyl group, pivaloyloxymethyl group, etc., alkoxycarbonyloxyalkyl group, for example, 1-(ethoxycarbonyloxy)ethyl group etc., 5-substituted-2-oxo-1,3-dioxol-4-ylmethyl group, for example, 5-methyl-2-oxo-1,3-dioxol-4-ylmethyl group etc., and the like can be mentioned.

Next, explanation will be made about the preparation processes for the compounds of the invention.

The compounds of general formula [I] can be prepared through either of following processes of preparation process A and preparation process B.

Preparation process A

The inventive compounds [I] can be prepared by reacting compounds represented by a general formula [II]

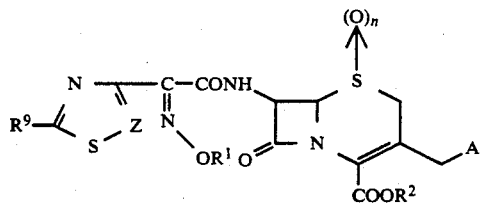

[wherein $R^1$ indicates a straight-chain or branched lower alkyl group, which may be substituted by carboxyl group which may be protected, trityl group, hydrogen atom or fluorine-substituted lower alkyl group, $R^2$ indicates a hydrogen atom, metal atom, protective group for carboxyl group or ester residue producible hydrolyzable ester in vivo, $R^9$ indicates an amino group, which may be protected, Z indicates N or CH, n indicates 0 or 1, and A indicates an eliminating group], with compounds represented by a general formula [III]

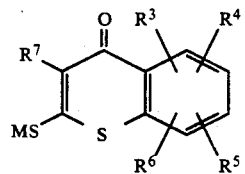

[wherein $R^3$, $R^4$, $R^5$ and $R^6$, which may be identical or different, indicate hydrogen atoms, halogen atoms, straight-chain or branched lower alkyl groups, which may be substituted, mercapto groups, which may be substituted, lower alkylamino groups, hydroxyl groups, which maybe protected, lower alkoxy groups, lower alkanoyl groups, lower alkoxycarbonyl groups, or lower alkylenedioxy group, which may be substituted, being maybe formed with $R^3$ and $R^4$, $R^7$ indicates a hydrogen atom, cyano group, halogen atom or $COOR^8$ ($R^8$ is hydrogen or lower alkyl group), and M indicates a hydrogen atom, metal atom or quaternary ammonium), and, if necessary, by reducing and/or removing the protective group.

Here, as the eliminating groups A in the compounds of general formula [II]. concretely, halogen atoms such as chlorine, bromine and iodine or acetoxy group, carbamoyloxy group, trifluoromethanesulfonyl group, p-toluenesulfonyloxy group, etc. can be mentioned and, particularly, chlorine atom, bromine atom, iodine atom and acetoxy group are preferable.

Moreover, M in the compounds of general formula [III] means a hydrogen atom, metal atom or quaternary ammonium. Here, as the metal atoms, for example, sodium, potassium, calcium, magnesium, aluminum, etc. can be mentioned and, as particularly preferable examples, sodium and potassium are mentioned. As the quaternary ammoniums, for example, triethylhydrogenammonium, tri-n-butylhydrogenammonium, tripropylhydrogenammonium, tri-i-propylhydrogenammonium, di-i-propylethylhydrogenammonium, tetraethylammonium, tetra-n-butylammonium, hydrogenpyridinium, etc. can be mentioned and, as particularly preferable examples, triethylhydrogenammonium, tri-n-butylhydrogenammonium and hydrogenpyridinium are mentioned.

The reaction between compounds of general formula [II] and thiochromone derivatives of general formula [III] can be conducted in organic solvents, for example, methylene chloride, chloroform, ether, ethyl acetate, tetrahydrofuran, acetonitrile, N,N-dimethylformamide, dimethyl sulfoxide, etc. or in mixed solvents thereof. In the reaction, 1 to 2 mol of thiochromone derivative of general formula [III] are used for 1 mol of compound of general formula [II]. The reaction temperature is 0° to 40° C. and the reaction time is 0.5 to 10 hours.

Moreover, the reaction between compounds of general formula [II],. A being acetoxy group, and thiochromone derivatives of general formula [III] can be conducted in solvents, for example, water, phosphate buffer, acetone, acetonitrile, methanol, ethanol, tetrahydrofuran, dioxane, N,N-dimethylformamide, dimethyl sulfoxide, etc. or mixed solvents thereof. The reaction is preferable to be conducted in the vicinity of neutral condition. The reaction temperature is from room temperature to 90° C. and the reaction time is 1 to 10 hours. Moreover, this reaction is promoted by conducting in the presence of iodides such as sodium iodide and potassium iodide, thiocyanates such as sodium thiocyanate and potassium thiocyanate, and the like.

Compounds of general formula [I], n being 0, can be prepared by reducing sulfoxide group according to the processes described in J. Org. Chem., 35, 2430 (1970) etc. Namely, compounds of general formula [I], n being 1, are reacted for 1 to 5 hours after dropwise addition of acetyl chloride at −40° to 0° C. in acetone solvent in the presence of sodium iodide or potassium iodide, or compounds of general formula [I], n being 1, are reacted for 0.5 to 5 hours after dropwise addition of phosphorus tribromide or phosphorus trichloride at −40° to 0° C. in the solvent of N,N-dimethylformamide, methylene chloride, ethyl acetate or the like to reduce. In the reaction, 3.5 to 10 mol of iodide and 1,5 to 5 mol of acetyl chloride or 1.1 to 6 mol of phosphorus trichloride or phosphorus tribromide are used for 1 mol of compound of general formula [I], n being 1.

In the inventive compounds [I], the protective group can be removed, if need be.

For the protective groups for carboxyl group, amino group and hydroxyl group in the general formula aforementioned, it is possible to use the protective groups usually used in the field of β-lactam synthesis of appropriate selection.

For introducing and removing the protective group, methods described in, for example, "Protective Groups in Organic Synthesis" written by T. W. Green and published by Wiley Inc. in 1981 etc. can be used by appropriate selection depending on the type of that protective group.

As the protective groups for carboxyl group, for example, t-butyl group, 2,2,2-trichloroethyl group, acetoxymethyl group, propionyloxymethyl group, pivaloyloxymethyl group, 1-acetoxyethyl group, benzyl group, 4-methoxybenzyl group, 3,4-dimethoxybenzyl group, 4-nitrobenzyl group, benzhydryl group, bis(4-methoxyphenyl)methyl group, trialkylsilyl group, etc. can be mentioned and, particularly, 4-methoxybenzyl group, benzhydryl group, t-butyl group, trimethylsilyl group, t-butyldimethylsilyl group, etc. are preferable.

As the protective groups for amino group, for example, trityl group, formyl group, chloroacetyl group, trifluoroacetyl group, t-butoxycarbonyl group, trimethylsilyl group, t-butyldimethylsilyl group, etc. can be mentioned.

As the protective groups for hydroxyl group, for example, 2-methoxyethoxymethyl group, methoxymethyl group, methylthiomethyl group, tetrahydropyranyl group, phenacyl group, i-propyl group, t-butyl group, benzyl group, 4-nitrobenzyl group, acetyl group, 2,2,2-trichloroethoxycarbonyl group, benzyloxycarbonyl group, t-butoxycarbonyl group, trimethylsilyl group, t-butyldimethylsilyl group, also, for example, orthoesters such as methoxymethylidene and methoxyethylidene, cyclic acetals such as benzylideneacetal, methyleneacetal and ethyleneacetal, cyclic ketals such as acetonide, alkylenedioxys such as methylenedioxy group and cyclic carbonate, which are formed by linking the protective groups one another, and the like can be mentioned.

Concretely explaining the removing methods of protective group, the removal of protective groups such as trityl group, formyl group, t-butoxycarbonyl group, benzhydryl group, 2-methoxyethoxymethyl group and 4-methoxybenzyl group can be performed with inorganic or organic acids, for example, hydrochloric acid, formic acid, trifluoroacetic acid, benzenesulfonic acid, p-toluenesulfonic acid, etc. and particularly trifluoroacetic acid is preferable.

Besides, when using trifluoroacetic acid as an acid, the reaction is promoted and the side reaction is also suppressed by adding anisole, thioanisole or phenol.

Moreover, the reaction can be conducted in solvents, for sample, water, methylene chloride, chloroform, benzene, etc., which do not participate with the reaction, or mixed solvents thereof. The reaction temperature and the reaction time are appropriately selected depending on the chemical properties of the inventive compounds [I] and the type of protective groups and, particularly, it is preferable to conduct under conditions of from ice-cooling to warming or so.

The starting material compounds [II] in the preparation process A can be prepared as follows:

Compounds of general formula [II], n being 0, can be prepared by reacting 7-amino-3-chloromethyl-3-cephem-4-carboxylic acid derivatives [synthesizable according to, for example, the process of J. Antibiotics, 38, 1738 (1985)], 7-aminocephalosporanic acid or its ester with compounds represented by a general formula [V]

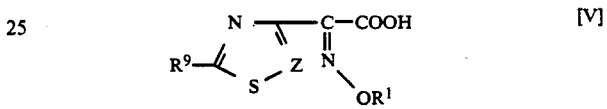

[wherein $R^1$ indicates a straight-chain or branched lower alkyl group, which may be substituted by carboxyl group which may be protected, trityl group, hydrogen atom of fluorine-substituted lower alkyl group, Z indicates N or CH, and $R^9$ indicates an amino group, which may be protected], or their reactive derivatives (for example, acid halide, mixed acid anhydride, active ester, etc.).

Compounds of general formula [II], n being 1, can be prepared by oxidizing compounds of general formula [II], n being 0, with equimolar of m-chloroperbenzoic acid, hydrogen peroxide or metaperiodic acid under ice-cooling to at room temperature in organic solvents, for example, methylene chloride, ethylene chloride, chloroform, ether, acetic acid, etc., which do not participate with the reaction, or mixed solvents thereof according to the process described in J. Org. Chem., 35, 2430 (1970).

Compounds of general formula [II], group A being iodine atom, are prepared by reacting compounds of general formula [II], group A being chlorine atom, with iodides such as sodium iodide and potassium iodide under ice-cooling to at room temperature in organic solvents, for example, acetone, N,N-dimethylformamide, dimethylsulfoxide, etc., or in two-layer systems according to, for example, the process described in Synth. Commun., 16, 1029 (1986), or they can also be prepared by reacting compounds [II], group A being acetoxy group, with iodotrimethylsilane in, for example, methylene chloride, chloroform, ether, ethylacetate, tetrahydrofuran, acetonitrile, N,N-dimethylformamide, dimethyl sulfoxide or mixed solvents thereof according to the process described in Tetrahedron Lett., 22, 3915 (1981). They may be used for next reaction without isolation or purification.

2-(2-Aminothiazole-4-yl)-2-substituted-oxyiminoacetic acid derivatives or 2-(5-amino-1,2,4-thiodiazole-3-yl)-2-substituted-oxyiminoacetic acid derivatives can be prepared by using 2-(2-aminothiazole-4-yl)glyoxylic acid derivatives, 2-(5-amino-1,2,4-thiadiazole-3-yl)glyoxylic acid derivatives, 2-(2-aminothiazole-4-yl)-2-hydroxyiminoacetic acid derivatives or 2-(5-amino-1,2,4-thiadiazole-3-yl)-2-hydroxyiminoacetic acid derivatives according to the processes described in Chem. Pharm. Bull., 25, 3115 (1977) etc.

Thiochromone derivatives of general formula [III] can be prepared according to the processes described in Tetrahedron, 34, 725 (1978) etc.

Preparation process B

The inventive compounds [I] can be prepared by acylating compounds represented by a general formula [IV]

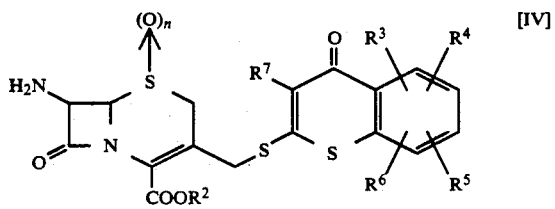

[wherein $R^2$ indicates a hydrogen atom, metal atom, protective group for carboxyl group or ester residue producible hydrolyzable ester in vivo, $R^3$, $R^4$, $R^5$ and $R^6$, which may be identical or different, indicate hydrogen atoms, halogen atoms, straight-chain or branched lower alkyl groups, which may be substituted, mercapto groups, which may be substituted, lower alkylamino groups, hydroxyl groups, which may be protected, lower alkoxy groups, lower alkanoyl groups, lower alkoxycarbonyl groups, or lower alkylenedioxy group, which may be substituted, being maybe formed with $R^3$ and $R^4$, $R^7$ indicates a hydrogen atom, cyano group, halogen atom or $COOR^8$ ($R^8$ is hydrogen or lower alkyl group), and n indicates 0 or 1], or their salts with compounds represented by the general formula [V] or their reactive derivatives and, if necessary, by reducing said compounds and/or removing the protective group.

In more detail, it is possible to prepare by reacting compounds of general formula [IV] with compounds of general formula [V] or their reactive derivatives (for example, acid halide, mixed acid anhydride, active ester, etc.) in solvents, for example, water, acetone, dioxane, acetonitrile, tetrahydrofuran, methylene chloride, chloroform, benzene, ethyl acetate, N,N-dimethylformamide, dimethyl sulfoxide, etc., which do not influence on the reaction, or mixed solvents thereof.

In the reaction, 1 to 1.5 mol of compounds of general formula [V] or its reactive derivative are used for 1 mol of compound of general formula [IV]. The reaction temperature is −40° to 40° C. and the reaction time is 0.5 to 10 hours.

When using acid halide as a reactive derivative of compound of general formula [V], it is preferable to conduct in the presence of deacidifying agents, for example, triethylamine, N-methylmorpholine, N,N-dimethylaniline, pyridine, etc.

In the reaction of forming acid halide, 1 to 10 mol, preferably 1 to 1.5 mol of halogenating agents such as thionyl chloride, phosphorus trichloride, phosphorus tribromide, phosphorus pentachloride, phosphorus oxychloride, oxalyl chloride and phosgene are used for 1 mol of compound [V]. The reaction temperature is −40° to 100° C., preferably −20° to 20° C. and the reaction completes for the reaction time of 10 to 120 minutes.

In the reaction of forming mixed acid anhydride, 1 to 1.2 mol of deacidifying agents, for example, triethylamine, N-methylmorpholine, N,N-dimethylaniline, pyridine, etc. and 1 to 1.2 mol of chloroformates, for example, methylchloroformate, ethylchloroformate, i-butylchloroformate, etc. are used for 1 mol of compound [V]. The reaction temperature is −40° to 20° C., preferably −20° to 5° C. and the reaction time is 10 to 60 minutes.

In the reaction of forming active ester, 1 to 1.2 mol of N-hydroxy compounds (for example, N-hydroxysuccinimide, 1-hydroxybenzotriazole, etc.) or phenol compounds (for example, 4-nitrophenol, 2,4-dinitrophenol, 2,4,5-trichlorophenol, etc.) and 1 to 1.4 mol of N,N-dicyclohexylcarbodiimide are used for 1 mol of compound [V]. The reaction temperature is −10° to 50° C. and the reaction time is 0.5 to 2 hours.

Moreover, when using compounds of general formula [V] as the form of free acids in acylation, compounds of general formula [I] can also be prepared in the presence of condensing agents such as carbodiimides such as N,N-dicyclohexylcarbodiimide or phosphorus oxychloride or N,N-dimethylformamide.phosphorus oxychloride adduct.

The starting material compounds [IV] in the preparation process B can be prepared through the processes described in "Cephalosporins and Penicillins" written by Flynn, Academic Press, p. 151-171 (1972) etc. For example, they can be prepared in a way that 7-acylamino-3-halomethyl-3-cephem-4-carboxylic acid derivatives (synthesizable according to the processes in Japanese Unexamined Patent Publication No. Sho 58-72590 and No. Sho 58-154588) or 7-acylaminocephalosporanic acid derivatives or 7-benzylideneaminocephalospranic acid derivatives are reacted with thiochromone derivatives of general formula [III] to convert to compounds represented by a general formula [VI]

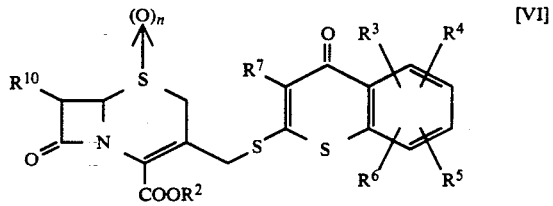

[wherein $R^2$ indicates a hydrogen atom, metal atom, protective group for carboxyl group or ester residue producible hydrolyzable ester in vivo, $R^3$, $R^4$, $R^5$ and $R^6$, which may be identical or different, indicate hydrogen atoms, halogen atoms, straight-chain or branched lower alkyl groups, which may be substituted, mercapto groups, which may be substituted, lower alkylamino groups, hydroxyl groups, which may be protected, lower alkoxy groups, lower alkanoyl groups, lower alkoxycarbonyl groups, or lower alkylenedioxy group, which may be substituted, being maybe formed with $R^3$ and $R^4$, $R^7$ indicates a hydrogen atom, cyano group, halogen atom or $COOR^8$ ($R^8$ is hydrogen or lower alkyl group), $R^{10}$ indicates an acylamino group or benzylideneamino group, and n indicates 0 or 1], and then by deacylating and debenzylidenating them.

The deacylating reaction is already publicly known in the same field and, when $R^{10}$ is, for example, phenylacetylamino group, phenoxyacetylamino group or aminoadipylamino group in the compounds represented by said general formula, it can be removed according to the method described in Japanese Patent Publication No. Sho 49-20319. Namely, after said compounds were reacted with phosphorus pentachloride or phosphorus oxychloride for 0.5 to 2 hours at −80° to 50° C., preferably −65° to 0° C. in benzene, toluene, ethylacetate, methylene chloride, ethylene chloride or mixed solvents thereof in the presence of deacidifying agents, for example, N,N-dimethylaniline, pyridine, triethylamine, sodium hydrogencarbonate, potassium hydrogencarbonate, etc., they are treated with lower alcohols, for example, methanol, ethanol, propanol, etc. and then hydrolyzed, thus the acyl group in acylamino group of $R^{10}$ can be removed.

Further, the removal of phenylacetyl group, phenoxyacetyl group or aminoadipyl group in acylamino group can also be carried out by the method described in Japanese Unexamined Patent publication No. Sho 63-264487, wherein penicillin G acylase or fixed penicillin G acylase is treated at a pH of 7 to 8, preferably 7.5 to 7.8 at room temperature in water or mixed solvents of organic solvents, for example, acetone, acetonitrile, methanol, ethanol, tetrahydrofuran, etc. with water. It is preferable to conduct the reaction by adding the bases, for example, lithium hydroxide, sodium hydroxide, potassium hydroxide, triethylamine, tripropylamine, pyridine, etc. and by keeping pH constant.

The removal of benzylidene group in acylamino group can be performed by treating at −20° to 60° C., preferably under ice-cooling to at room temperature in acids, for example, hydrochloric acid, sulfuric acid, formic acid, acetic acid, trifluoroacetic acid, etc. or mixtures thereof according to the method described in "Protective Groups in Organic Synthesis" written by T. W. Green and published by Wiley Inc. in 1981.

[Antibacterial activity]

The inventive compounds [I] or their salts are novel compounds and exhibit strong antibacterial activity that inhibits the growth of a wide range of pathogenic microorganisms including Gram-positive and Gram-negative bacteria. In order to demonstrate the usefulness of the inventive compounds [I], the in vitro antibacterial activity determined according to the standard method of the Japan Chemotherapy Society using cefotaxime (CTX) and ceftazidime (CAZ) as referential compounds is shown in Table 1.

drugs, liquid drugs such as injections, syrups and emulsions, solid drugs such as tablets, capsules and granules, external drugs such as ointments and suppositories, and the like can be mentioned. Moreover, in these drugs, additives such as auxiliary agent, stabilizier, lubricant, emulsifiers, absorption promoter and suffactant, which are used ordinarily, may be contained, if necessary. As the additives, distilled water for injection, Ringer's solution, glucose, sucrose syrup, gelatin, edible oil, cacao fat, ethylene glycol, sucrose, corn starch, magnesium stearate, talc, etc. can be mentioned.

Further, the compounds of the invention can be used for the therapy and the prevention of bacterial infections of human or animals. The dosage differs depending on the states of age, distinction of sex, etc. of patient, but it is preferable to administer in amounts of 1 to 1000 mg/kg a day once or five times.

In following, the invention will be illustrated in more detail on the basis of examples, but the invention is not confined to these.

EXAMPLE 1 p-Methoxybenzyl 3-chloromethyl-7-[(Z)-2-methoxyimino-2-(2-tritylaminothiazole-4-yl)acetamide]-3-cephem-4-carboxylate 1-oxide

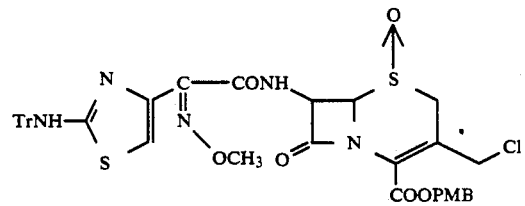

(Note) PMB: p-methoxybenzyl group

To a solution of 0.4 g (0.504 mmol) of p-methoxybenzyl 3-chloromethyl-7-[(Z)-2-methoxyimino-2-(2-tritylaminothiazole-4-yl)acetamido]-3-cephem-4-carboxylate in 6 ml of dichloromethane was added a solution of 137 mg (0.554 mmol) of 70% m-chloroperbenzoic acid in 5 ml of dichloromethane at 0° C. under stirring, and the mixture was stirred for 15 minutes at the same temperature. The solution was poured into saturated sodium-bicarbonate solution. The organic layer was washed with saturated saline solution, dried over anhydrous sodium sulfate and then solvent was

|  |  | Minimum inhibitory concentration for growth (μg/ml) | | | | | | |
|---|---|---|---|---|---|---|---|---|
| Tested microorganism ($10^6$ cells/ml) | Gram | Example 75 | Example 90 | Example 100 | Example 108 | Example 110 | CTX | CAZ |
| *Staphylococcus aureus* 209P | (+) | 0.39 | 1.56 | 12.5 | 6.25 | 6.25 | 0.78 | 3.13 |
| *S. epidermidis* IID 866 | (+) | 0.78 | 1.56 | 12.5 | 12.5 | 12.5 | 0.78 | 3.13 |
| *Streptococcus pneumoniae* Type III | (+) | 0.10 | 0.10 | 3.13 | 0.78 | 0.78 | 0.10 | 0.39 |
| *Escherichia coli* ATCC 10536 | (−) | ≦0.0063 | ≦0.0063 | ≦0.0063 | ≦0.0063 | ≦0.0063 | 0.025 | 0.05 |
| *Klebsiella pneumoniae* 1-220 S | (−) | ≦0.0063 | ≦0.0063 | ≦0.0063 | ≦0.0063 | ≦0.0063 | 0.05 | 0.20 |
| *Pseudomonas aeruginosa* IFO 12689 | (−) | 0.39 | 0.05 | 0.10 | 0.05 | 0.05 | 25 | 3.13 |

Hence, the compounds of general formula [I] and their pharmacologically permissible salts or physiologically hydrolyzable nontoxic esters are useful as antibacterial agents.

The compounds of the invention can be used in the forms of medicinal drugs suitable for parenteral administration, oral administration or external administration by mixing with solid or liquid carriers of excipients publicly known in the same field. As the medicinal distilled off. The residue was purified by means of silica gel column chromatography ($CHCl_3$-AcOEt 5:1) to obtain 0.252 g (0.311 mmol) of title compound (field 62%).

$^1$H - NMR (400MHz, $CDCl_3$, δ): 3.38 (1H, d, J=18.6Hz), 3.78 (1H, d, J=18.6Hz), 3.81 (3H, s), 4.07 (3H, s), 4.24 (1H, d, J=12.7Hz), 4.54 (1H, d, J=4.9Hz), 4.97 (1H, d, J=12.7Hz), 5.25 (2H, s), 6.15 (1H, dd, J=4.9, 10.3Hz), 6.69 (1H, s), 6.9–7.4 (19H, m).

EXAMPLE 2 p-Methoxybenzyl 3-(3-ethoxycarbonyl-6,7,8-trifluoro-4-oxo-4H-1-benzothiopyran-2-yl)thiomethyl-7-[(Z)-2-methoxyimino-2-(2-trithylaminothiazole-4-yl)acetamido]-3-cephem-4-carboxylate 1-oxide

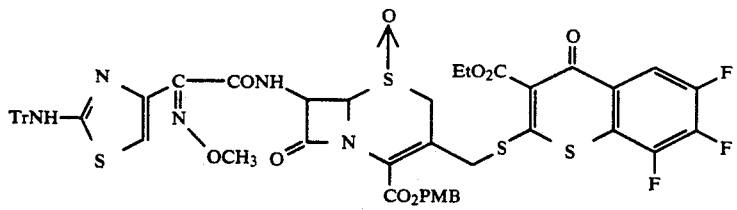

To a solution of 78.3 mg (0.297 mmol) of ethyl 3-(2,3,4,5-tetrafluorophenyl)-3-oxopropionate, 0.2 ml of dried dimethyl sulfoxide and 22.7 mg (0.298 mmol) of carbon disulfide were added 60.2 mg (0.595 mmol) of triethylamine, and the mixture was stirred for 1 hour (liquor A).

Separately, to a solution of 241 mg (0.297 mmol) of p-methoxybenzyl 3-chloromethyl-7-[(Z)-2-(2-tritylaminothiazole-4-yl)-2-methoxyimino acetamido]-3-cephem-4-carboxylate 1-oxide in 5 ml of dried dimethyl sulfoxide were added 281 mg (1.87 mmol) of sodium iodide, and the mixture was stirred for 1 hour (liquor B).

Liquor B was added dropwise to liquor A and the mixture was stirred for 3 hours, which was poured into ice-water and extracted twice with dichloromethane. The organic layer was washed with water and with saturated saline solution, dried over anhydrous sodium sulfate and then solvent was distilled off. The residue was purified by means of silica gel column chromatography (CHCl$_3$-AcOEt 2:1→1:1) to obtain 192 mg (0.176 mmol) of title compound (yield 59%).

$^1$H - NMR (90MHz, CDCl$_3$, δ): 1.37 (3H, t, J=7.0 Hz), 3.59 (2H, brs), 3.79 (3H, s), 4.07 (3H, s), 4.37 (2H, q, J=7.0 Hz) 4.76 (1H, d, J=4.8 Hz), 4.9-5.3 (4H, m), 6.16 (1H, dd, J=4.8, 10.0Hz), 6.77 (1H, s), 6.8-7.4 (19H, m), 7.9-8.2 (1H, m).

EXAMPLE 3 p-Methoxybenzyl 3-(3-ethoxycarbonyl-6,7,8-trifluoro-4-oxo-4H-1-benzothiopyran-2-yl)thiomethyl-7-[(Z)-2-methoxyoxo-imino-2-(2-trithylaminothiazole-4-yl)acetamido]-3-cephem-4-carboxylate

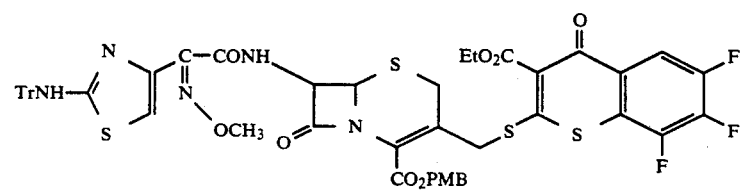

To a solution of 572 mg (0.523 mmol) of the compound of Example 2 in 7 ml of dimethylformamide were added dropwise 0.05 ml (0.523 mmol) of phosphorus tribromide under cooling with ice, and the mixture was stirred for 30 minutes at the same temperature. The reaction mixture was poured into ice-water and extracted twice with dichloromethane. The organic layer was washed with water and with saturated saline solution, dried over anhydrous sodium sulfate and then solvent was distilled off. the residue was purified by means of silica gel column chromatography (CHCl$_3$-AcOEt 10:3) to obtain 402 mg (0.373 mmol) of title compound (yield 71%).

EXAMPLE 4

Sodium 7β-[(Z)-2-(2-aminothiazole-4-yl)-2-methoxyiminoacetamido]-3-(3-ethoxycarbonyl-6,7,8-trifluoro-4-oxo-4H-1-benzothiopyran-2-yl)thiomethyl-3-cephem-4-carboxylate

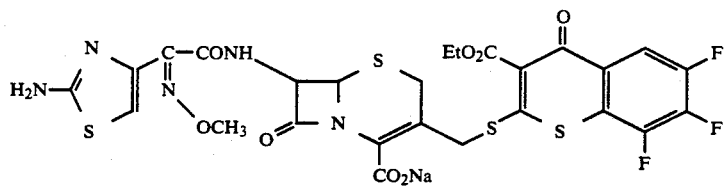

To a solution of 402 mg (0.373 mmol) of the compound of Example 3 in 0.527 ml of anisole were added dropwise 2.64 ml of trifluoroacetic acid under cooling with ice, and the mixture was stirred for 4 hours at the same temperature. The reaction mixture was poured into 79 ml of isopropyl ether cooled with ice. The crystals deposited were collected by filtration and dried. The crystals were suspended into 3 ml of water and saturated sodium bicarbonate solution was added under cooling with ice, pH was adjusted to 7.6, insolubles were removed, and the aimed product was eluted with CH$_3$CN-H$_2$O 3:7 using column chromatography packed with Lichroprep RP-8 Lobar. After freeze-drying, 153 mg (0.217 mmol) of title compound were obtained (yield 58%).

$^1$H-NMR (90 MHz, CD$_3$ OD, δ): 1.37 (3H, t, J=7.0Hz), 3.32 (1H, d, J=7.0 Hz), 3.82 (1H, d, J=7.0 Hz), 3.96 (3H, s) 4.39 (2H, q, J=7.0 Hz), 4.0-4.8 (2H, m), 5.09 (1H, d, J=4.4 Hz), 5.74 (1H, d, J=4.4 Hz), 6.81 (1H, s), 8.0-8.2 (1H, m), dd), J=4.9, 10.0 Hz), 6.67 (1H, s), 6.8-7.4 (20H, m), 8.0-8.2 (1H, m).

EXAMPLE 6 p-Methoxybenzyl 3-(6,7,8-trifluoro-4-oxo-4H-1-benzothiopyran-2-yl)thiomethyl-7-[(Z)-2-methoxyimino-2-(2-tritylaminothiazole-4-yl)acetamide]-3-cephem-4-carboxylate

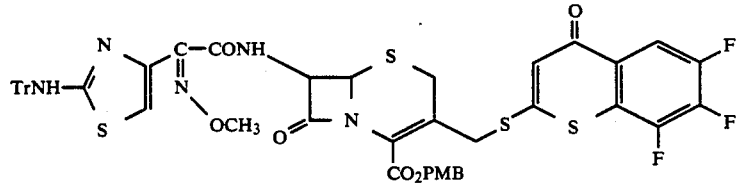

IR (KBr, cm$^{-1}$) : 1750, 1600.

EXAMPLE 5 p-Methoxybenzyl 3-(6,7,8-trifluoro-4-oxo-4H-1-benzo-thiopyran-2-yl)thiomethyl-7-[(Z)-2-methoxyimino-2-(2-tritylaminothiazole-4-yl)acetamido]-3-cephem-4-carboxylate 1-oxide Similarly to Example 3, 242 mg (0.241 mmol) of title compound were obtained from 363 mg (0.355 mmol) of the compound of Example 5 (yield 68%).

$^1$H - NMR (90 MHz, CDCl$_3$, δ): 3.40 (1H, d, J=18.0Hz), 3.6-3.8 (1H, m), 3.78 (3H, s), 4.0-4.2 (1H, m) 4.07 (3H, s), 4.10 (1H, d, J=14.0Hz), 4.36 (1H, d, J=14.0Hz), 5.01 (1H, d, J=4.8Hz), 5.14 (2H, s), 5.91 (1H, dd, J=4.8, 10.0Hz), 6.71 (1H, s), 6.8-7.4 (19H, m), 7.0-7.3 (1H, m).

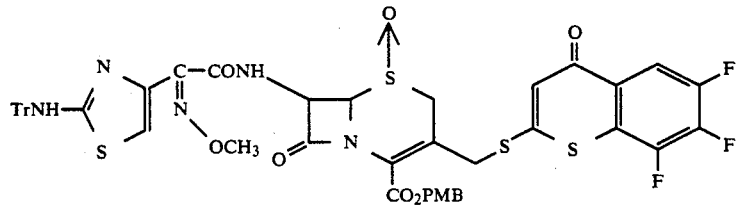

To a solution of 300 mg (1.56 mmol) of 2',3',4',5'-tetrafluoroacetophenone, 3.17 ml of dried dimethyl sulfoxide and 119 mg (1.56 mmol) of carbon disulfide were added little by little 125 mg (3.13 mmol) of 60% sodium hydride, and the mixture was stirred for 5 hours (liquor A).

Separately, to a solution of 1.27 g (1.56 mmol) of the compound of Example 1 in 26 ml of dried dimethyl sulfoxide were added 281 mg (1.87 mmol) of sodium iodide, and the mixture was stirred for 1.3 hours (liquor B).

Liquor B was added dropwise to liquid A and the mixture was stirred for 1 hour, which was poured into 1.5 liters of ice-water and extracted twice with dichloromethane. The organic layer was washed with water and with saturated saline solution, dried over anhydrous sodium sulfate and then solvent was distilled off. The residue was purified by means of silica gel column chromatography (CHCl$_3$-AcOEt 2:1→1:1) to obtain 363 mg (0.355 mmol) of title compound (yield 23%).

$^1$H - NMR (90 MHz, CDCl$_3$, δ): 3.7-3.8 (2H, m), 3.79 (3H, s), 3.9-4.1 (1H, m), 4.07 (3H, s), 4.54 (1H, d, J=4.9 Hz), 4.80 (1H, d, J=14.0 Hz), 5.1-5.3 (2H, m), 6.14 (1H,

EXAMPLE 7

Sodium 7β-[(Z)-2-(2-aminothiazole-4-yl)-2-methoxyiminoacetamido]-3-(6,7,8-trifluoro-4-oxo-4H-1-benzothiopyran-2-yl)thiomethyl-3-cephem-4-carboxylate

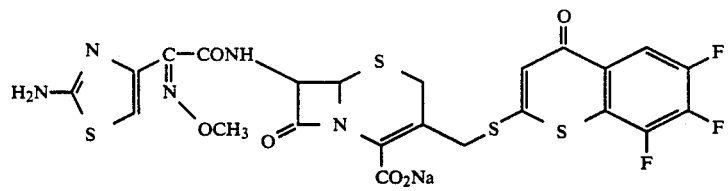

Similarly to Example 4, 443 mg (0.0699 mmol) of title compound were obtained from 242 mg (0.241 mmol) of the compound of Example 6 (yield 29%).

$^1$H-NMR (90MHz, CD$_3$OD, δ): 3.3-3.4 (1H, m), 3.78 (1H, d, J=18.0Hz), 3.96 (3H, s) 4.16 (1H, d, J=13.0Hz), 4.60 (1H, d, J=13.0Hz), 5.08 (1H, d, J=4.8Hz), 5.74 (1H, d, J=4.8Hz), 6.82 (1H, s), 7.97 (1H, s), 8.0-8.2 (1H, m),

IR (KBr, cm$^{-1}$): 1750, 1600.

EXAMPLE 8 p-Methoxybenzyl 3-(4-oxo-4H-1-benzothiopyran-2-yl)thiomethyl-7-[(Z)-2-methoxyimino-2-(2-tritylaminothiazole-4-yl)acetamido]-3-cephem-4-carboxylate 1-oxide

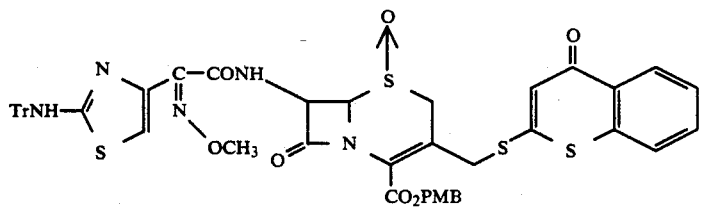

Similarly to Example 5, 401 mg (0.414 mmol) of title compound were obtained from 1.27 g (1.56 mmol) of the compound of Example 1 and 216 mg (1.56 mmol) of 2'-fluoroacetophenone (yield 27%).

$^1$H-NMR (90MHz, CDCl$_3$, δ): 3.6–3.8 (2H, m), 3.77 (3H, s), 3.7–3.9 (1H, m) 4.06 (3H, s), 4.51 (1H, d, J=5.0Hz), 4.90 (1H, d, J=15.0Hz), 5.1–5.3 (2H, m), 6.12 (1H, dd, J=5.0, 11.0Hz), 6.67 (1H, s), 6.8–7.6 (23H, m), 8.4–8.6 (1H, m).

EXAMPLE 9 p-Methoxybenzyl 3-(4-oxo-4H-1-benzothiopyran-2-yl)thiomethyl-7-[(Z)-2-methoxyimino-2-(2-tritylaminothiazole-4-yl)acetamido]-3-cephem-4-carboxylate

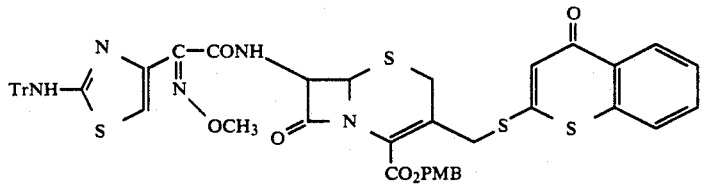

Similarly to Example 3, 305 mg (0.32 mmol) of title compound were obtained from 401 mg (0.414 mmol) of the compound of Example 8 (yield 77%).

$^1$H - NMR (90MHz, CDCl$_3$, δ): 3.40 (1H, d, J=18.0Hz), 3.6–3.8 (1H, m), 3.77 (3H, s), 3.9–4.1 (1H, m), 4.06 (3H, s), 4.37 (1H, d, J=13.0Hz), 5.00 (1H, d, J=4.8Hz), 5.15 (2H, s), 5.90 (1H, dd, J=4.8, 8.0Hz), 6.71 (1H, s), 6.8–7.6 (23H, m), 8.4–8.6 (1H, m).

EXAMPLE 10

Sodium 7 β-[(Z)-2-(2-aminothiazole-4-yl)-2-methoxyiminoacetamido]-3-(4-oxo-4H-1-benzothiopyran-2-yl)thiomethyl-3-cephem-4-carboxylate

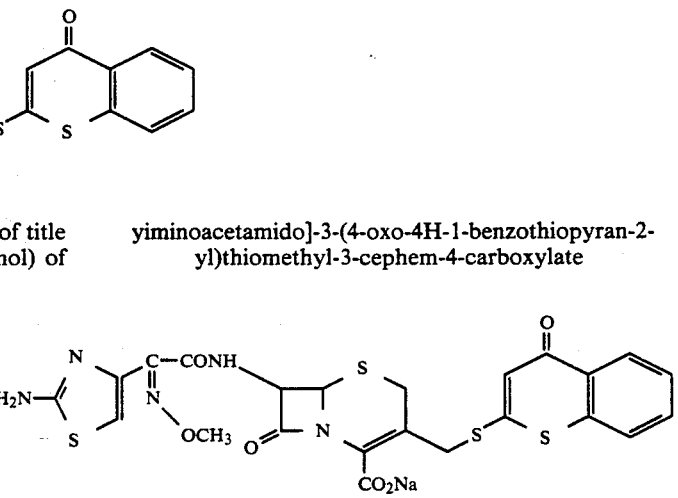

Similarly to Example 4, 129 mg (0.223 mmol) of title compound were obtained from 305 mg (0.321 mmol) of the compound of Example 9 (yield 69%).

$^1$H-NMR (90MHz, CD$_3$ OD, δ): 3.42 (1H, d, J=17.0Hz), 3.78 (1H, d, J=17.0Hz), 3.96 (3H, s), 4.10 (1H, d, J=13.0Hz), 4.74 (1H, d, J=13.0Hz), 5.04 (1H, d, J=4.8Hz), 5.74 (1H, d, J=4.8Hz), 6.82 (1H, s), 7.04 (1H, s), 7.5–7.9 (3H, m), 8.4–8.5 (1H, m).

IR (KBr, cm$^{-1}$): 1760, 1580.

EXAMPLE 11 p-Methoxybenzyl 3-[3-ethoxycarbonyl-6,8-difluoro-4-oxo-7-(1-pyrrolidinyl)-4H-1-benzothiopyran-2-yl]thiomethyl-7-[(Z)-2-methoxyimino-2-(2-tritylaminothiazole-4-yl)acetamido]-3-cephem-4-carboxylate 1-oxide

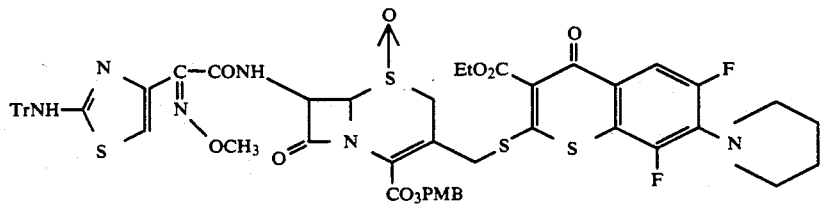

Similarly to Example 5, 915 mg (0.799 mmol) of title compound were obtained from 491 mg (1.56 mmol) of ethyl 3-(2,3,5-trifluoro-4-pyrrolidinylphenyl)-3-oxopropionate (Yield 51%).

¹H-NMR (90MHz, CDCl₃δ): 1.36 (3H, t, J=7.0Hz), 1.8–2.0 (4H, m), 2.2–2.8 (6H, m), 3.79 (3H, s), 4.06 (3H, s), 4.35 (2H, q, J=7.0Hz), 4.8–5.4 (5H, m), 6.10 (1H, dd, J=5.0, 10.0Hz), 6.67 (1H, s), 6.7–7.4 (19H, m), 7.79 (1H, dd, J=1.0, 13.0Hz).

EXAMPLE 12 p-Methoxybenzyl 3-(3-ethoxycarbonyl-6,8-difluoro-4-oxo-7-(1-pyrrolidinyl)-4H-1-benzothiopyran-2-(2-tritylamino-thiazole-4-yl)acetamido]-3-cephem-4-carboxylate

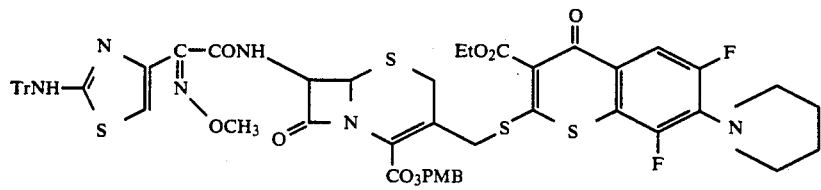

Similarly to Example 3, 567 mg (0.502 mmol) of title compound were obtained from 903 mg (0.788 mmol) of the compound of Example 11 (yield 64%).

¹H-NMR (90MHz, CDCl₃, δ): 1.38 (3H, t, J=7.0Hz), 1.8–2.0 (4H, m), 3.30 (1H, d, J=1.80Hz), 3.6–3.8 (4H, m), 3.78 (3H, s), 3.9–4.1 (1H, m), 4.06 (3H, s), 4.1–4.8 (2H, m), 4.40 (2H, q, J=7.0Hz), 4.9–5.3 (1H, m), 5.11 (2H, d, J=2.0Hz) 5.89 (1H, dd, J=4.8, 9.0Hz), 6.69 (1H, s), 6.8–7.4 (19H, m), 7.8 (1H, dd, J=1.8, 15.0Hz).

EXAMPLE 13

Sodium 7β-[(Z)-2-(2-aminothiazole-4-yl)-2-methoxyiminoacetamido]-3-[3-ethoxycarbonyl-6,8-difluoro-4-oxo-7-(1-pyrrolidinyl)-4H-1-benzothiopyran-2-yl]thiomethyl-3-cephem-4-carboxylate

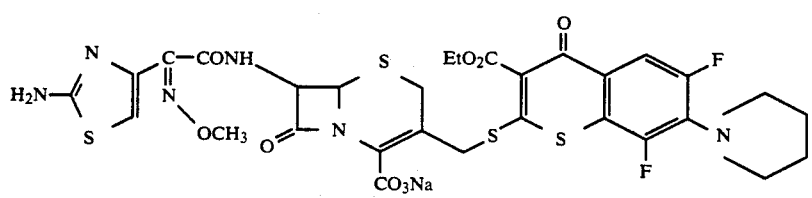

Similarly to Example 4, 60.9 mg (0.0772 mmol) of title compound were obtained from 530.2 mg (0.470 mmol) of the compound of Example 12 (yield 16%).

EXAMPLE 14 p-Methoxybenzyl 3-[3-ethoxycarbonyl-6,8-difluoro-7-(4-methylpiperazine-1-yl)-4-oxo-4H-1benzothiopyran-2-yl]-thiomethyl-7-[(Z)-2-methoxyimino-2-(2-tritylaminothiazole-4-yl)acetamido]-3-cephem-4-carboxylate 1-oxide

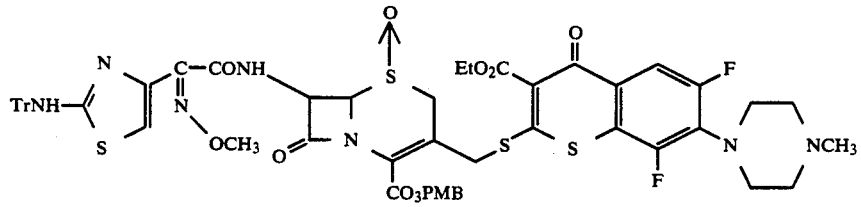

Similarly to Example 5, 818 mg (0.697 mmol) of title compound were obtained from 429 mg (1.25 mmol) of ethyl 3-[2,3,5-trifluoro-4-(4-methylpiperazine)-1-yl]-3-oxopropionate (yield 56%).

¹H-NMR (90MHz, CDCl₃, δ): 1.36 (3H, t, J=7.0Hz), 2.34 (3H, s), 2.4–2.6 (8H, m), 3.6–4.0 (2H, m), 3.79 (3H, s), 4.0–4.6 (4H, m), 4.07 (3H, s), 4.8–5.3 (3H, m), 6.12 (1H, dd, J=5.0, 10.0Hz), 6.67 (1H, s), 6.8–7.4 (19H, m), 7.92 (1H, dd, J=2.0, 12.0Hz).

EXAMPLE 15 p-Methoxybenzyl 3-[3-ethoxycarbonyl-6,8-difluoro-7-(4-methylpiperzine-1-yl)-4-oxo-4H-1-benzothiopyran-2-yl]-thiomethyl-7-[(Z)-2-methoxyimino-2-(2-tritylaminothiazole-4-yl)-acetamido]-3-cephem-4-carboxylate

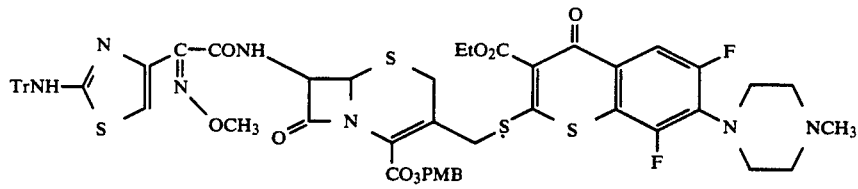

Similarly to Example 3, 319 mg (0.275 mmol) of title compound were obtained from 806 mg (0.686 mmol) of the compound of Example 14 (yield 40%).

¹H-NMR (90MHz, CDCl₃, δ): 1.38 (3H, t, J=7.0Hz), 2.34 (3H, s), 2.4-2.6 (4H, m), 3.3-3.5 (4H, m), 3.6-4.0 (2H, m), 3.78 (3H, s), 4.0-4.6 (4H, m), 4.06 (3H, s), 5.0-5.2 (3H, m), 5.90 (1H, dd, J=5.0, 10.0Hz), 6.71 (1H, s), 6.8-7.4 (19H, m), 7.92 (1H, dd, J=2.0, 12.0Hz).

EXAMPLE 16

Sodium 7β-[(Z)-2-(2-aminothiazole-4-yl)-2-methoxyiminoacetamido]-3-[3-ethoxycarbonyl-6,8-difluoro-7-(4-methylpiperazine-1-yl)-4-oxo-4H-1-benzothiopyran-2-yl]thiomethyl-3-cephem-4-carboxylate.

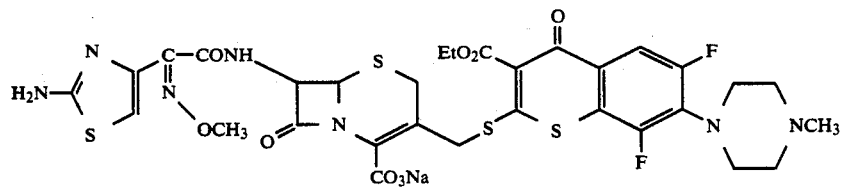

Similarly to Example 4, 8.5 mg (0.0104 mmol) of title compound were obtained from 319 mg (0.275 mmol) of the compound of Example 15 (yield 4%).

EXAMPLE 17

3-Ethoxycarbonyl-2-methylthio-4-oxo-4H-1-benzothiopyran

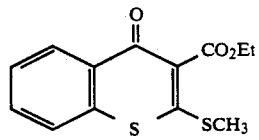

To a suspension of 3.04 g (76.1 mmol) of 60% sodium hydride in 50 ml of dried dimethyl sulfoxide was added a solution of 8.00 g (38.1 mmol) of ethyl 2-fluorobenzoylacetate, 2.89 g (38.0 mmol) of carbon disulfide and 20 ml of dried dimethyl sulfoxide at room temperature, and the mixture was stirred for 2 hours at 100° C. Then, this was cooled to room temperature by allowing to stand and, after added 6.48 g (45.7 mmol) of methyl iodide, the mixture was stirred for 2 hours, which was poured into ice-water and extracted with dichloromethane. The organic layer was washed with water and with saturated saline solution, dried over anhydrous sodium sulfate and then solvent was distilled off. The residue was purified by means of silica gel column chromatography (CHCl₃→CHCl₃-AcOEt 40:1) to obtain 3.06 g (10.9 mmol) of title compound (yield 29%).

¹H-NMR (90MHZ, CDCl₃, δ): 1.41 (3H, t, J=7.0Hz), 2.66 (3H, s), 4.44 (2H, q, J=7.0Hz), 7.4-7.6 (3H, m), 8.4-8.6 (1H, m).

EXAMPLE 18

3-Ethoxycarbonyl-2-methylsulfinyl-4-oxo-4H-1-benzothiopyran

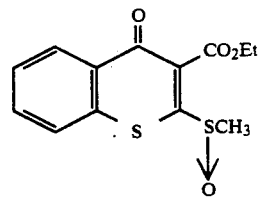

To a solution of 3.06 g (10.0 mmol) of the compound of Example 17 in 63 ml of dichloromethane was added a solution of 2.35 g of 70% m-chloroperbenzoic acid in 52 ml of dichloromethane, and the mixture was stirred for 30 minutes as the same temperature.

The reaction liquor was poured into saturated sodium bicarbonate solution. The organic layer was washed with water and with saturated saline solution, dried over anhydrous sodium sulfate and then solvent was distilled off. The residue was purified by means of silica gel column chromatography (CHCl₃-AcOEt 10.1) to obtain 2.75 g (9.27 mmol) of title compound (yield 85%).

¹H-NMR (90MHZ, CDCl₃, δ): 1.42 (3H, t, J=7.0Hz), 3.11 (3H, s), 4.44 (2H, q, J=7.0Hz), 7.6-7.8 (3H, m), 8.4-8.6 (1H, m). MS (M/Z) (296 (M⁺)).

EXAMPLE 19

3-Ethoxycarbonyl-2-mercapto-4-oxo-4H-1-benzothiopyran

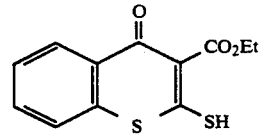

To a solution of 100 mg (0.337 mmol) of the compound of Example 18 in 1.8 ml of tetrahydrofuran was added 1N sodium hydrogensulfide (0.697 mmol), and the mixture was stirred for 3 hours. Solvent was distilled off and 87 mg of sodium bicarbonate and 6.5 ml of water were added to the residue, which was washed with dichloromethane. After added 2.2 ml of 1N hydrochloric acid, this was extracted with dichloromethane. The organic layer was washed with saturated saline solution and concentrated. The residue was purified by means of silica gel column chromatography (CHCl₃) to obtain title compound (yield 23%).

¹H - NMR (90MHz, CDCl₃, δ): 1.44 (3H, t, J=7.0Hz), 4.49 (2H, q, J=7.0Hz), 7.2-7.7 (3H, m), 8.2-8.4 (1H, m).

EXAMPLE 20

Diphenylmethyl 3-(3-ethoxycarbonyl-4-oxo-4H-1-benzothiopyran-2-yl)thiomethyl-7-[(Z)-2-methoxyimino-2-(2-tritylamino-thiazole-4-yl)acetamido]-3-cephem-4-carboxylate 1-oxide

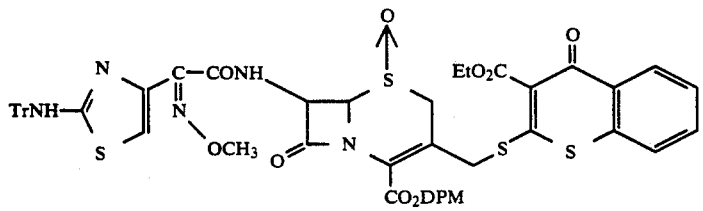

(Note) DPM: diphenylmethyl group

To a solution of 800 mg (0.934 mmol) of diphenylmethyl 3-chloromethyl-7-[(Z)-2-methoxyimino-2-(2-tritylaminothiazole-4-yl)acetamido]-3-cephem-4-carboxylate 1-oxide in 2 ml of dimethylformamide were added 168 mg (1.12 mmol) of sodium iodide, and the mixture was stirred for 1 hour. A solution of 274 mg (1.03 mmol) of the compound of Example 19 in 2.4 ml of dimethylformamide was added under cooling with ice and the mixture was stirred for 1.5 hours at room temperature, which was poured into ice-water and extracted with dichloromethane. The organic layer was washed with water and with saturated saline solution, dried over anhydrous sodium sulfate and then solvent was distilled off. The residue was purified by means of silica gel column chromatography (CHCl$_3$-AcOEt 10:3) to obtain 683 mg (0.628 mmol) of title compound (yield 67%).

$^1$H - NMR (90MHz, CDCl$_3$, δ): 1.35 (3H, t, J=7.0Hz), 3.5–3.7 (2H, m), 4.07 (3H, s), 4.35 (2H, q, J=7.0Hz), 4.86 (1H, d, J=5.0Hz), 5.0–5.3 (2H, m), 6.16 (1H, dd, J=5.0, 10.0Hz), 6.64 (1H, m), 7.0–7.7 (29H, m), 8.3–8.5 (1H, m).

EXAMPLE 21

Diphenylmethyl 3-(3-ethoxycarbonyl-4-oxo-4H-1-benzothiopyran-2-yl)thiomethyl-7-[(Z)-methoxyimino-2-(2-tritylamino-thiazole-4-yl)acetamido]-3-cephem-4-carboxylate

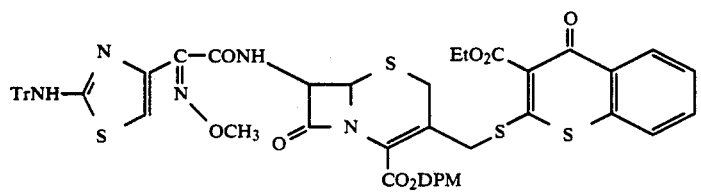

Similarly to Example 3, 320 mg (0.299 mmol) of title compound were obtained from 678 mg (0.624 mmol) of the compound of Example 20 (yield 48%).

$^1$H - NMR (90MHz, CDCl$_3$, δ): 1.35 (3H, t, J=7.0Hz), 3.4–4.0 (2H, m), 4.07 (3H, s), 4.2–4.6 (2H, m), 4.38 (2H, q, J=7.0Hz), 5.15 (1H, d, J=5.0Hz), 6.00 (1H, dd, J=5.0, 10Hz), 6.89 (1H, s), 6.9–7.6 (29H, m), 8.4–8.6 (1H, m).

EXAMPLE 22

Sodium 7β-[(Z)-2-(2-aminothiazole-4-yl)-2-methoxyiminoacetamido]-3-(3-ethoxycarbonyl-4-oxo-4H-1benzothiapyran-2-yl]thiomethyl-3-cephem-4-carboxylate

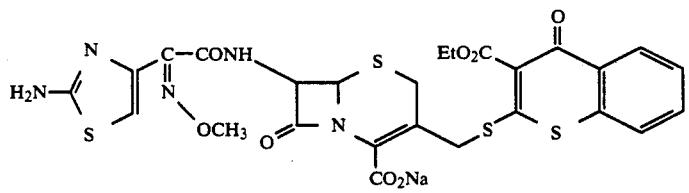

Similarly to Example 4, 58.6 mg (0.0899 mmol) of title compound were obtained from 314 mg (0.293 mmol) of the compound of Example 21 (yield 31%).

$^1$H - NMR (90MHz, CD$_3$OD, δ): 1.38 (3H, t, J=7.3Hz), 3.36 (1H, d, J=17.0Hz), 3.84 (1H, d, J=17.0Hz), 3.95 (3H, s), 4.0–4.8 (2H, m), 4.38 (2H, q, J=7.3Hz), 5.05 (1H, d, J=4.8Hz), 5.73 (1H, d, J=4.8Hz), 6.81 (1H, s), 7.4–7.9 (3H, m), 8.3–8.5 (1H, m).

IR (KBr, cm$^{-1}$): 1750, 1600.

EXAMPLE 23

7-Fluoro-2-methylthio-4-oxo-4H-1-benzothiopyran

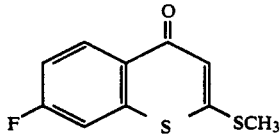

Similarly to Example 17, 385 mg (1.70 mmol) of title compound was obtained from 300 mg (1.92 mmol) of 2',4'-difluoroacetophenone (yield 89%).

$^1$H - NMR (90MHz, CDCl$_3$, δ): 2.62 (3H, s), 6.82 (1H, s), 7.1–7.4 (2H, m), 8.4–8.6 (1H, m).

EXAMPLE 24

7-Fluoro-2-methylsulfinyl-4-oxo-4H-1-benzothiopyran

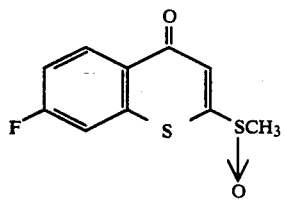

Similarly to Example 18, 2.20 g of title compound were obtained from 2.00 g (8.84 mmol) of the compound of Example 23.

EXAMPLE 25

7-Fluoro-2-mercapto-4-oxo-4H-1-benzothiopyran

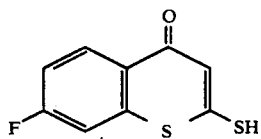

Similarly to Example 19, 947 mg of title compound were obtained from 1.06 g (4.39 mmol) of the compound of Example 24.

$^1$H - NMR (90MHz, d$_6$ DMSO, δ): 7.09 (1H, s), 7.40 (1H, ddd, J=2.6, 8.8, 9.2Hz), 7.67 (1H, dd, J=2.6, 9.0Hz), 8.22 (1H, dd, J=5.7, 9.2Hz).

EXAMPLE 26 p-Methoxybenzyl 3-(7-fluoro-4-oxo-4H-1-benzothiopyran-2-yl)thiomethyl-7-[(Z)-2-methoxyimino-2-(2-tritylaminothiazole-4-yl)acetamido]-3-cephem-4-carboxylate 1-oxide

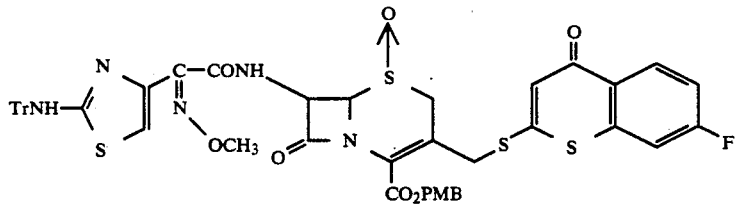

Similarly to Example 20, 573 mg (0.581 mmol) of title compound were obtained from 700 mg (0.864 mmol) of the compound of Example 1 and 202 mg (0.950 mmol) of the compound of Example 25 (yield 69%).

$^1$H-NMR (90NHz, CDCl$_3$, δ): 3.4–3.9 (2H, m), 3.78 (3H, s), 3.8–4.1 (1H, m), 4.06 (3H, s), 4.54 (1H, d, J=5.0Hz), 4.84 (1H, d, J=14.0Hz), 5.19 (2H, s), 6.14 (1H, dd, J=5.0, 10.0Hz), 6.67 (1H, dd, J=5.0, 10.0Hz), 6.8–7.4 (22H, m), 8.43 (1H, dd, J=5.7, 9.0Hz).

EXAMPLE 27 p-Methoxybenzyl 3-(7-fluoro-4-oxo-4H-1-benzothiopyran-2-yl)thiomethyl-7-[(Z)-2-methoxyimino-2-(2-tritylaminothiazole-4-yl)acetamido]-3-ephem-4-carboxylate

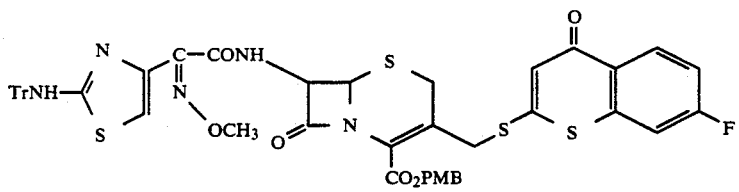

Similarly to Example 3, 279 mg (0.288 mmol) of title compound were obtained from 565 mg (0.573 mmol) of the compound of Example 26 (yield 50%).

$^1$ H - NMR (90MHz, CDCl$_3$, δ): 3.56 (1H, d, J=11.0Hz), 3.8–4.2 (2H, m), 3.77 (3H, s), 4.06 (3H, s), 4.36 (1H, d, J=13.0Hz), 5.00 (1H, d, J=5.0Hz), 5.03 (2H, s), 5.90 (1H, dd, J=5.0, 10.0Hz), 6.70 (1H, s), 6.8–7.4 (22H, m), 8.50 (1H, dd, J=6.0, 9.0Hz).

EXAMPLE 28

Sodium 7β-[(Z)-2-(2-aminothiazole-4-yl)-2-methoxyiminoacetamido]-3-(7-fluoro-4-oxo-4H-1-benzothiopyran-2-yl)thiomethyl-3-cephem-4-carboxylate

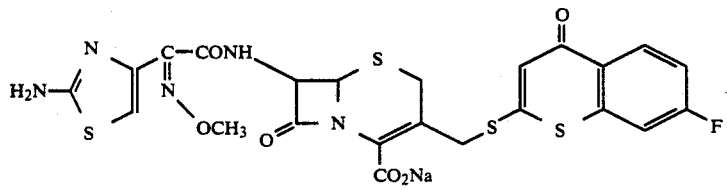

Similarly to Example 4, 291 mg (0.0487 mmol) of title compound were obtained from 271 mg (0.280 mmol) of the compound of Example 27 (yield 17%).

$^1$H - NMR (90MHz, CD$_3$ OD, δ): 3.40 (1H, d, J=17.0Hz), 3.78 (1H, d, J=17.0 Hz), 3.96 (3H, s), 4.08 (1H, d, J=13.0Hz), 4.72 (1H, d, J=13.0Hz), 5.07 (1H, d, J=4.8Hz), 5.74 (1H, d, J=4.8Hz), 6.82 (1H, d, J=4.8Hz), 7.02 (1H, s), 7.36 (1H, ddd, J=2.6, 9.0, 9.0Hz), 7.55 (1H, dd, J=2.6, 9.0Hz), 8.41 (1H, dd, J=5.7, 9.0Hz), Ir (KBr, cm$^{-1}$): 1750, 1600.

EXAMPLE 29

6,7,8-Trifluoro-2-methylthio-4-oxo-4H-1-benzothiopyran

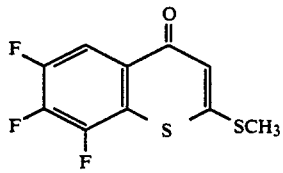

Similarly to Example 17, 60.5 mg (0.231 mmol) of title compound were obtained from 100 mg (0.521 mmol) of 2', 3', 4',5'-tetrafluoroacetophenone (yield 44%).

$^1$H - NMR (90MHz, CDCl$_3$, δ): 2.66 (3H, s), 6.83 (1H, s), 8.0-8.3 (1H, m).

EXAMPLE 30

6.8-Difluoro-2-methylthio-7-(4-methyl-4H-1,2,4-triazole-3-ylthio)-4-oxo-4H-1-benzothiopyran

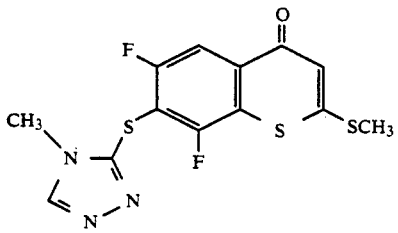

To a solution of 50 mg (0.191 mmol) of the compound of Example 29 in 1 ml of acetonitrile were added 24.2 mg (0.210 mmol) of 3-mercapto-4-methyl-4H-1,2,4-triazole and 29.0 mg (0.191 mmol) of 1.8-diazabicyclo[5,4,0]-7-undecene, and the mixture was stirred for 2 hours at 50° C. After cooling by allowing to stand, the crystals deposited were collected by filtration, washed with cold acetonitrile and dried to obtain 51 mg (0.143 mmol) of title compound (yield 75%).

MS (M/Z): 357 (M+)

EXAMPLE 31

6,8-Difluoro-7-(4-methyl-4H-1,2,4-triazole-3-ylthio)-2-methylsulfinyl-4-oxo-4H-1-benzothiopyran

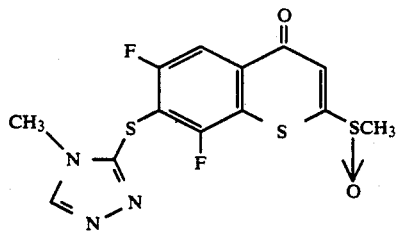

Similarly to Example 18, 28.6 mg (0.0766 mmol) of title compound were obtained from 38.2 mg (0.107 mmol) of the compound of Example 30 (yield 72%).

$^1$H - NMR (90MHz, d$_6$ DMSO, δ): 2.94 (3H, s), 3.62 (3H, s), 7.29 (1H, s), 7.89 (1H, dd, J=1.8, 9.2Hz), 8.57 (1H, s),

MS (M/Z): 357 (M+).

EXAMPLE 32

6.8-Difluoro-2-mercapto-7-(4-methyl-4H-1,2,4-triazole-3-ylthio)-4-oxo-4H-1-benzothiopyran

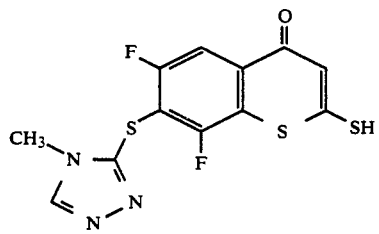

Similarly to Example 19, 407 mg (1.19 mmol) of title compound were obtained from 566 mg (1.52 mmol) of the compound of Example 31 (yield 78%).

EXAMPLE 33 p-Methoxybenzyl 3-[6,8-difluoro-7-(4-methyl-4H-1,2,4-triazole-3-ylthio)-4-oxo-4H-1-benzothiopyran-2-yl]thiomethyl-7-[(Z)-2-methoxyimino-2-(2-tritylaminothiazole-4-yl)-acetamido]-3-cephem-4-carboxylate 1-oxide

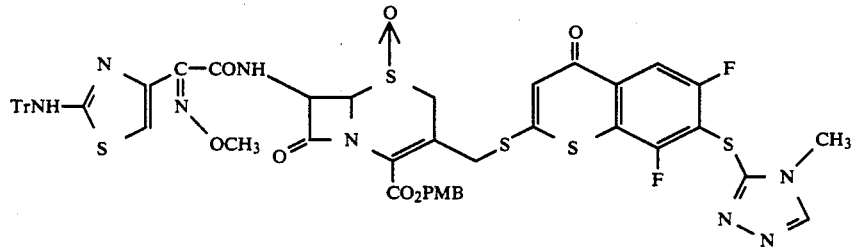

Similarly to Example 20, 828 mg (0.741 mmol) of title compound were obtained from 700 mg (0.864 mmol) of the compound of Example 1 and 236 mg (0.950 mmol) of the compound of Example 32 (yield 86%).

$^1$H - NMR (90MHz, CDCl$_3$, δ): 3.4-4.8 (4H, m), 3.78 (3H, s), 3.79 (3H, s), 4.06 (3H, s), 4.56 (1H, d, J=5.0Hz), 5.1-5.3 (2H, m), 6.40 (1H, dd, J=5.0, 10.0Hz), 6.68 (1H, s), 6.8-7.4 (20H, m), 7.9-8.1 (1H, m), 8.21 (1H, s).

EXAMPLE 34 p-Methoxybenzyl 3-[6,8-difluoro-7-(4-methyl-4H-1,2,4-triazole-3-ylthio)-4-oxo-4H-1-benzothiopyran-2-yl]thiomethyl-7-[(Z)-2-methoxyimino-2-(2-tritylaminothiazole-4yl)-acetamido]-3-cephem-4-carboxylate

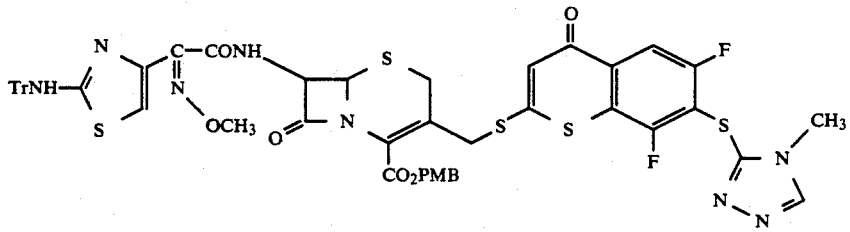

Similarly to Example 3, 203 mg (0.185 mmol) of title compound were obtained from 820 mg (0.734 mmol) of the compound of Example 33 (yield 25%).

¹H - NMR (90MHz, CDCl₃, δ): 3.77 (3H, s), 3.80 (3H, s), 3.4-4.6 (4H, m), 4.04 (3H, s), 5.06 (1H, d, J=5.0Hz), 5.1-5.3 (2H, m), 5.92 (1H, dd, J=5.0, 10.0Hz) 6.71 (1H, s), 6.8-7.4 (20H, m), 8.0-8.2 (1H, m), 8.22 (1H, s).

EXAMPLE 35

Sodium 7β-[(Z)2-(2-aminothiazole-4-yl)-2-methoxyiminoacetamido]-3-[6,8-difluoro-7-(4-methyl-4H-1,2,4-triazole-3-ylthio)-4-oxo-4H-1-benzothiopyran-2-yl]-thiomethyl-3-cephem-4-carboxylate

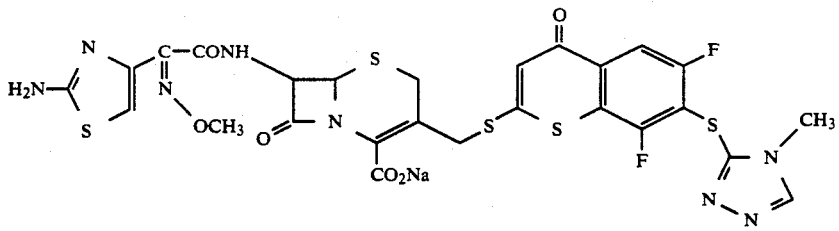

Similarly to Example 4, 70.7 mg (0.0953 mmol) of title compound were obtained from 203 mg (0.185 mmol) of the compound of Example 34 (yield 52%).

¹H - NMR (90MHz, CD₃OD, δ): 3.4-4.4 (4H, m) 3.85 (3H, s), 3.96 (3H, s), 5.07 (1H, d, J=5.0Hz), 5.80 (1H, d, J=5.0Hz), 6.82 (1H, s), 7.09 (1H, s), 7.9-8.1 (1H, m), 8.5-8.7 (1H, m).

EXAMPLE 36 p-Methoxybenzyl 3-(7-fluoro-4-oxo-4H-1-benzothiopyran-2-yl)thiomethyl-7-[(Z)-2-(2-tritylaminothiazole-4-yl)-2-trityloxyiminoacetamido]-3-cephem-4-carboxylate 1-oxide

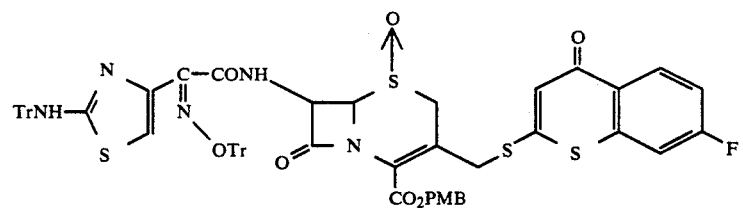

Similarly to Example 20, 1.37 g (1.13 mmol) of title compound were obtained from 1.48 g (1.43 mmol) of p-methoxybenzyl 3-chloromethyl 7-[(Z)-2-(2-tritylaminothiazole-4-yl)-2-trityloxyiminoacetamido]-3-cephem-4-carboxylate 1-oxide (yield 79%).

¹H - NMR (90MHz, CDCl₃, δ): 3.32 (1H, d, J=18.0Hz), 3.5-3.9 (2H, m), 3.79 (3H, s), 4.40 (1H, d, J=5.0 Hz), 4.80 (1H, d, J=14.0 Hz), 5.20 (2H, s), 6.24 (1H, dd, J=5.0, 10.0 Hz), 6.82 (1H, s), 6.9-7.6 (37H, m), 8.44 (1H, dd, J=5.7, 8.7 Hz).

EXAMPLE 37 p-Methoxybenzyl 3-(4-fluoro-4-oxo-4H-1-benzothiopyran-2-yl)thiomethyl-7-[(Z)-2-(2-tritylaminothiazole-4-yl)-2-trityloxyiminoacetamido]-3-cephem-4-carboxylate

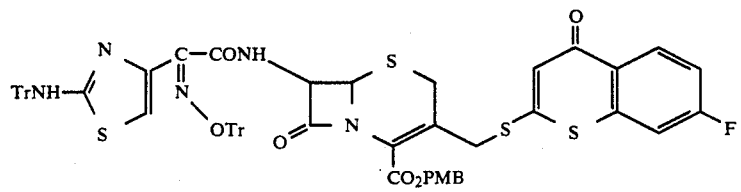

Similarly to Example 3, 357 mg (0.298 mmol) of title compound were obtained from 1.36 g (1.12 mmol) of the compound of Example 36 (yield 27%).

$^1$H-NMR (90 MHz, CDCl$_3$, δ): 3.20 (1H, d, J=18.0 Hz), 3.64 (1H, d, J=18.0 Hz), 3.78 (3H, s), 3.8–4.4 (2H, m), 5.04 (1H, d, J=5.0 Hz), 5.28 (2H, s), 6.04 (1H, dd, J=5.0, 10.0 Hz), 6.8–7.8 (38H, m), 8.4–8.6 (1H, m).

EXAMPLE 38

Sodium 7β-[(Z)-2-(2-aminothiazole-4-yl)-2-hydroxyiminoacetamido]-3-(7-fluoro-4-oxo-4H-1-benzothiopyran-2-yl)-thiomethyl-3-cephem-4-carboxylate

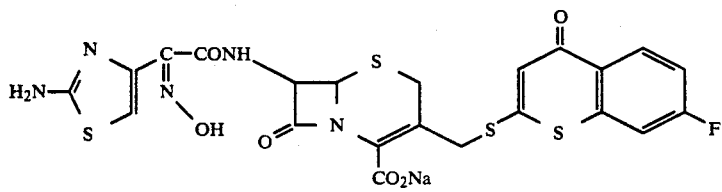

Similarly to Example 4, 88.0 mg (0.143 mmol) of title compound were obtained from 347 mg (0.289 mmol) of the compound of Example 37 (yield 49%).

$^1$H-NMR (90 MHz, CD$_3$OD, δ): 3.3–3.5 (1H, m), 3.72 (1H, d, J=18.0 Hz), 4.08 (1H, d, J=13.0 Hz), 4.6–4.9 (1H, m), 5.08 (1H, d, J=4.8 Hz) 5.77 (1H, d, J=4.8 Hz) 6.77 (1H, s), 6.0–6.7 (2H, m), 7.03 (1H, s), 8.2–8.6 (1H, m).

IR (KBr, cm$^{-1}$): 1740, 1600.

EXAMPLE 39 p-Methoxybenzyl 7-[(Z)-2-(1-tert-butoxycarbonyl-1-methylethoxy)imino-2-(2-tritylaminothiazole-4-yl)acetamido]-3-(7-fluoro-4-oxo-4H-1-benzothiopyran-2-yl)thiomethyl-3-cephem-4-carboxylate 1-oxide

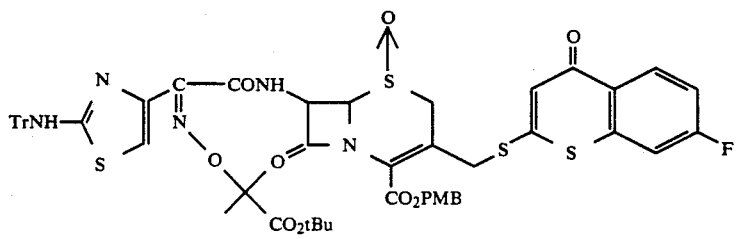

Similarly to Example 20, 601 mg (0.540 mmol) of title compound were obtained from 1.00 g (1.07 mmol) of p-methoxybenzyl 7-[(Z)-2-(1-tert-butoxycarbonyl-1-methylethoxyimino)-2-(2-tritylaminothiazole-4-yl)acetamido]-3-chloromethyl 3-cephem-4-carboxylate 1oxide (yield 50%).

$^1$H-NMR (90 MHz, CDCl$_3$, δ): 1.41 (9H, s), 1.55 (3H, s), 1.57 (3H, s), 3.40 (1H, d, J=18.0 Hz), 3.6–3.9 (2H, m), 3.79 (3H, s), 4.52 (1H, d, J=5.0 Hz), 4.92 (1H, d, J=14.0 Hz), 5.20 (2H, s), 6.96 (1H, dd, J=5.0, 10.0 Hz), 6.67 (1H, s), 6.8–7.4 (22H, m), 8.46 (1H, dd, J=5.7, 9.0 Hz).

EXAMPLE 40 p-Methoxybenzyl 7-[(Z)-2-(1-tert-butoxycarbonyl-1-methylethoxy)imino-2-(2-tritylaminothiazole-4-yl)acetamido]-3-(7-fluoro-4-oxo-4H-1-benzothiopyran-2-yl)thiomethyl-3-cephem-4-carboxylate

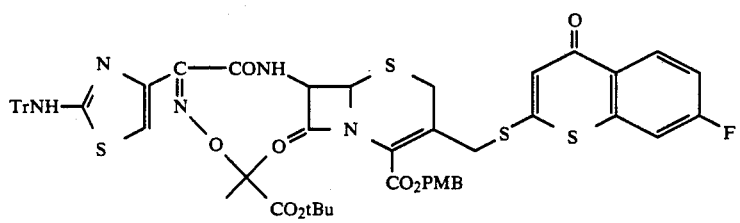

Similarly to Example 3, 208 mg (0.225 mmol) of title compound were obtained from 591 mg (0.630 mmol) of the compound of Example 39 (yield 36%).

$^1$H-NMR (90 MHz, CDCl$_3$, δ): 1.42 (9H, s), 1.58 (3H, s), 1.63 (3H, s), 3.36 (1H, d, J=18.0 Hz), 3.6–3.9 (1H, m), 3.78 (3H, s), 4.0–4.7 (2H, m), 5.00 (1H, d, J=5.0 Hz) 5.17 (2H, s), 5.96 (1H, d, J=5.0, 10.0 Hz) 6.71 (1H, s), 6.8–7.4 (22H, m), 8.48 (1H, dd, J=6.0, 9.0 Hz).

EXAMPLE 41

Disodium 7β-[(Z)-2-(2-aminothiazole-4-yl)-2-(1-carboxy-1-methylethoxy)iminoacetamido]-3-(7-fluoro-4-oxo-4H-1-benzothiopyran-2-yl)-thiomethyl-3-cephem-4-carboxylate

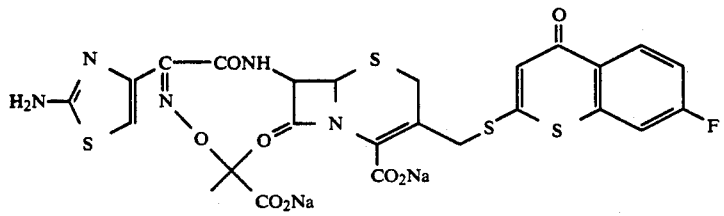

Similarly to Example 4, 73.9 mg (0.102 mmol) of title compound were obtained from 200 mg (0.217 mmol) of the compound of Example 40 (yield 47%).

$^1$H-NMR (90 MHz, CD$_3$, OD, δ): 1.53 (6H, s) 3.3–3.5 (1H, m), 3.76 (1H, d, J=17.0 Hz), 4.08 (1H, d, J=13.0 Hz), 4.7–4.9 (1H, m), 5.07 (1H, d, J=4.8 Hz) 5.74 (1H, d, J=4.8 Hz) 6.81 (1H, s), 7.05 (1H, s), 7.36 (1H, ddd, J=2.6, 9.0, 9.0 Hz), 7.56 (1H, dd, J=2.6, 9.0 Hz), 8.41 (1H, dd, J=5.7, 9.0 Hz), IR (KBr, cm$^{-1}$): 1750, 1500

EXAMPLE 42 p-Methoxybenzyl 7-[(Z)-2-tert-butoxycarbonylmethoxyimino-2-(2-tritylaminothiazole-4-yl)acetamido]-3-(7-fluoro-4-oxo-4H-1-benzothiopyran-2-yl)thiomethyl-3-cephem-4-carboxylate 1-oxide chloromethyl-3-cephem-4-carboxylate 1-oxide (yield 35%).

$^1$H-NMR (90 MHz, CDCl$_3$, δ): 1.43 (9H, s), 3.36 (1H, d, J=19.0 Hz), 3.5–3.8 (2H, m), 3.77 (3H, s), 4.52 (1H, d, J=5.0 Hz) 4.70 (2H, s), 4.8–5.2 (1H, m), 5.19 (2H, s), 5.96 (1H, dd, J=5.0, 10.0 Hz) 6.72 (1H, s), 6.8–7.4 (22H, m), 8.42 (1H, dd, J=5.7, 9.0 Hz).

EXAMPLE 43 p-Methoxybenzyl 7-[(Z)-2-tert-butoxycarbonylmethoxyimino-2-(2-tritylaminothiazole-4-yl)acetamido]-3-(7-fluoro-4-oxo-4H-1-benzothiopyran-2-yl)thiomethyl-3-cephem-4-carboxylate

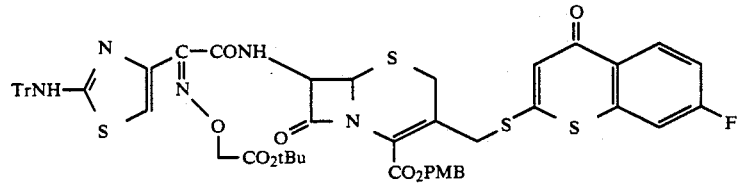

Similarly to Example 3, 137 mg (0.128 mmol) of title compound were obtained from 383 mg (0.352 mmol) of the compound of Example 42 (yield 36%).

$^1$H-NMR (90 MHz, CDCl$_3$, δ): 1.44 (9H, s), 3.36 (1H, d, J=18.0 Hz), 3.5–3.8 (1H, m), 3.77 (3H, s), 4.00 (1H, d, J=13.0 Hz), 4.36 (1H, d, J=13.0 Hz), 4.75 (2H, s), 5.00 (1H, dd, J=5.0 Hz), 5.17 (2H, s), 5.88 (1H, d, J=5.0, 10.0 Hz), 6.79 (1H, s), 6.8–7.4 (22H, m), 8.48 (1H, dd, J=6.0, 9.0 Hz).

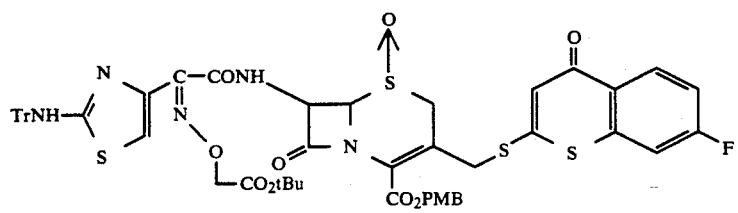

Similarly to Example 20, 400 mg (0.368 mmol) of title compound were obtained from 960 mg (1.05 mmol) of p-methoxybenzyl 7-[(Z)-2-tert-butoxycarbonylmethoxyimino-2-(2-tritylaminothiazole-4-yl)acetamido]-3-

EXAMPLE 44

Disodium
7β-[(Z)-2-(2-aminothiazole-4-yl)-2-carboxymethoxyiminoacetamido]-3-(7-fluoro-4-oxo-4H-1-benzothiopyran-2-yl)thiomethyl-3-cephem-4-carboxylate

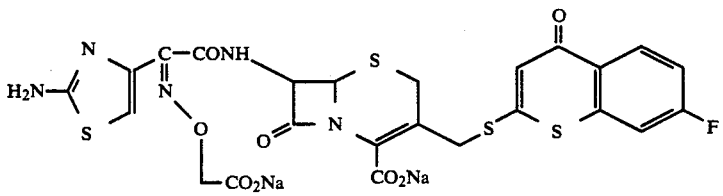

Similarly to Example 4, 45.2 mg (0.0650 mmol) of title compound were obtained from 130 mg (0.122 mmol) of the compound of Example 43 (yield 53%).

¹H-NMR (90 MHz, CD₃OD, δ): 3.0–4.8 (4H, m), 4.32 (2H, s), 5.04 (1H, d, J=5.0 Hz), 5.6–5.8 (1H, m), 6.83 (1H, s), 6.97 (1H, s), 7.48 (1H, ddd, J=3.0, 9.0, 9.0 Hz), 7.84 (1H, dd, J=3.0, 9.0 Hz), 8.36 (1H, dd, J=6.0, 9.0 Hz).

IR (KBr, cm⁻¹): 1740, 1580.

EXAMPLE 45 p-Methoxybenzyl 3-(4-oxo-4H-1-benzothiopyran-2-yl)-thiomethyl-7-[(Z)-2-(2-tritylamino-thiazole-4-yl)-2-trityloxyiminoacetamido]-3-cephem-4-carboxylate 1-oxide

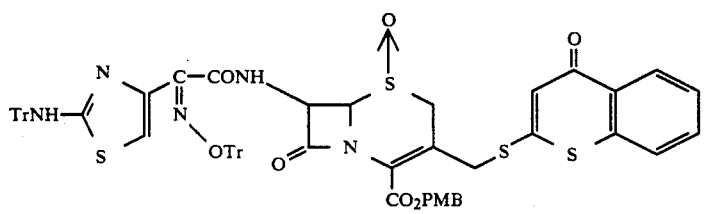

Similarly to Example 20, 669 mg (0.559 mmol) of title compound were obtained from 898 mg (0.865 mmol) of p-methoxybenzyl 3-chloromethyl 7-[(Z)-2-(2-tritylaminothiazole-4-yl)2-trityloxyiminoacetamido]-3-cephem-4-carboxylate 1-oxide (yield 65%).

¹H-NMR (90 MHz, CDCl₃, δ):
3.12 (1H, d, J=18.0 Hz), 3.38 (3H, s), 3.48 (1H, m), 4.36 (1H, d, J=5.0 Hz), 4.64 (1H, d, J=13.0 Hz), 4.96 (1H, d, J=13.0 Hz), 5.1–5.3 (2H, m), 6.20 (1H, dd, J=5.0, 10.0 Hz), 6.80 (1H, s), 6.8–7.6 (38H, m), 8.3–8.5 (1H, m).

EXAMPLE 46 p-Methoxybenzyl 3-(4-oxo-4H-1-benzothiopyran-2-yl)thiomethyl-7-[(Z)-2-(2-tritylaminothiazole-4-yl)-2-trityloxyiminoacetamido]-3-cephem-4-carboxylate

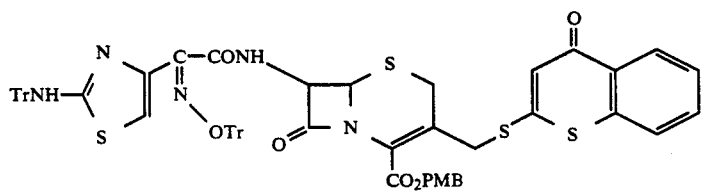

Similarly to Example 3, 360 mg (0.305 mmol) of title compound were obtained from 653 mg (0.546 mmol) of the compound of Example 45 (yield 56%).

¹H-NMR (90 MHz, CDCl₃, δ): 3.20 (1H, d, J=18.0 Hz), 3.60 (1H, d, J=18.0 Hz), 3.77 (3H, s), 3.96 (1H, d, J=13.0 Hz), 4.36 (1H, d, J=13.0 Hz), 5.00 (1H, d, J=4.8 Hz), 5.1–5.2 (2H, m), 5.96 (1H, dd, J=4.8, 10.0 Hz), 6.80 (1H, s), 6.8–7.6 (38H, m), 8.3–8.5 (1H, m).

EXAMPLE 47

Sodium
7β-[(Z)-2-(2-aminothiazole-4-yl)-2-hydroxyiminoacetamido]-3-(4-oxo-4H-1-benzothiopyran-2-yl)-thiomethyl-3-cephem-4-carboxylate

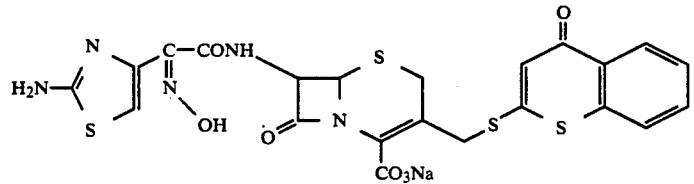

Similarly to Example 4, 82.7 mg (0.138 mmol) of title compound were obtained from 349 mg (0.296 mmol) of the compound of Example 46 (yield 47%).

¹H-NMR (90 MHz, CD₃OD, δ): 3.3–3.5 (1H, m), 3.76 (1H, d, J=17.0 Hz), 4.08 (1H, d, J=13.0 Hz), 4.68 (1H, d, J=13.0 Hz), 5.09 (1H, d, J=4.8 Hz), 5.77 (1H, d,

J=4.8 Hz), 6.76 (1H, s), 7.04 (1H, s), 7.3–7.8 (3H, m), 8.2–8.4 (1H, m),
IR (KBr, cm$^{-1}$): 1750, 1600.

EXAMPLE 48

6,7-Dimethoxy-2-methylthio-4-oxo-4H-1-benzothiopyran

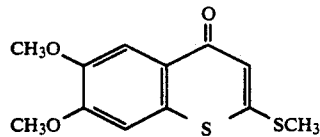

Similarly to Example 17, 150 mg (0.559 mmol) of title compound were obtained from 200 mg (1.0 mmol) of 2'-fluoro-4',5'-dimethoxyacetophenone (yield 57%).
$^1$H-NMR (90 MHz, CDCl$_3$, δ): 2.62 (3H, s), 3.97 (3H, s), 3.99 (3H, s), 6.85 (1H, s), 6.86 (1H, s), 7.88 (1H, s),
MS (M/Z): 268 (M+).

EXAMPLE 49

6,7-Dimethoxy-2-methylsulfinyl-4-oxo-4H-1-benzothiopyran

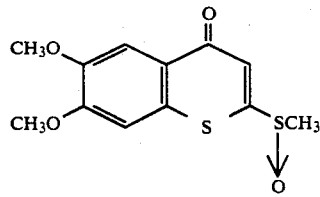

Similarly to Example 18, 1.25 g of title compound were obtained from 1.00 g (3.73 mmol) of the compound of Example 48.
$^1$H-NMR (90 MHz, d$_6$ DMSO, δ): 2.49 (3H, s), 3.01 (3H, s), 3.33 (3H, s), 7.24 (1H, s), 7.57 (1H, s), 7.71 (1H, s).

EXAMPLE 50

2-Mercapto-6,7-dimethoxy-4-oxo-4H-1-benzothiopyran

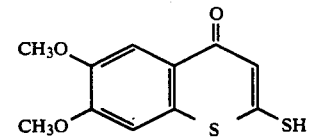

Similarly to Example 19, 1.15 g of title compound were obtained from 1.25 g (4.40 mmol) of the compound of Example 49.
MS (M/Z): 254 (M+)

EXAMPLE 51 p-Methoxybenzyl 3-(6,7-dimethoxy-4-oxo-4H-1-benzothiopyran-2-yl)thiomethyl-7-[(Z)-2-methoxyimino-2-(2-tritylaminothiazole-4-yl)acetamido]-3-cephem-4-carboxylate 1-oxide

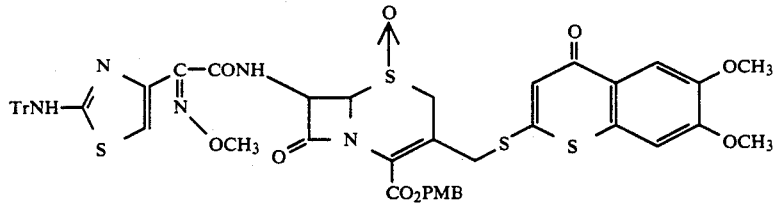

Similarly to Example 20, 1.64 g (1.59 mmol) of title compound were obtained from 2.10 g (2.59 mmol) of the compound of Example 1 and the compound of Example 50 (yield 62%).
$^1$H-NMR (90 MHz, CDCl$_3$, δ): 3.73 (3H, s), 3.89 (3H, s), 3.94 (3H, s), 4.01 (3H, s), 3.4–4.2 (2H, m), 4.64 (1H, d, J=5.0 Hz), 4.4–4.9 (2H, m), 4.7–5.3 (2H, m), 6.00 (1H, dd, J=5.0, 10.0 Hz), 6.64 (1H, s), 6.7–7.8 (22H, m).

EXAMPLE 52 p-Methoxybenzyl 3-(6,7-dimethoxy-4-oxo-4H-1-benzothiopyran-2-yl)thiomethyl-7-[(Z)-2-methoxyimino-2-(2-tritylaminothiazole-4-yl)acetamido]-3-cephem-4-carboxylate

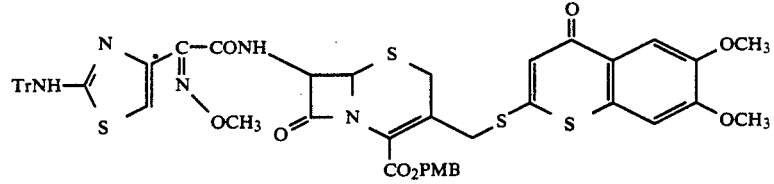

Similarly to Example 3, 664 mg (0.656 mmol) of title compound were obtained from 1.64 g (1.59 mmol) of the compound of Example 51 (yield 41%).
$^1$H-NMR (90 MHz, CDCl$_3$, δ): 3.2–4.3 (1H, m), 3.76 (3H, s), 3.95 (3H, s), 3.98 (3H, s), 4.05 (3H, s), 4.48 (1H, d, J=17.0 Hz), 4.96 (1H, d, J=5.0 Hz), 5.0–5.3 (4H, m), 5.94 (1H, dd, J=5.0, 10.0 Hz), 6.69 (1H, s), 6.7–7.4 (22H, m).

EXAMPLE 53

Sodium 7β-[(Z)-2-(2-aminothiazole-4-yl)-2-methoxyiminoacetamido]-3-(6,7-dimethoxy-4-oxo-4H-1-benzothiopyran-2-yl)thiomethyl-3-cephem-4-carboxylate

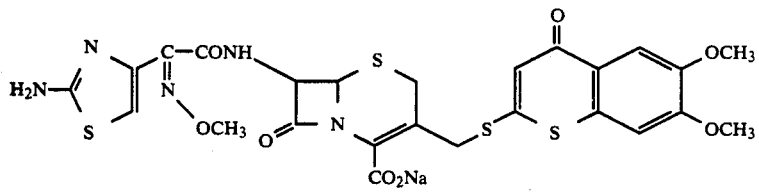

Similarly to Example 4, 21.1 mg (0.0314 mmol) of title compound were obtained from 154 mg (0.152 mmol) of the compound of Example 52 (yield 21%).

$^1$H-NMR (400 MHz, CD$_3$OD, δ): 3.42 (1H, d, J=17.6 Hz), 3.77 (1H, d, J=17.6 Hz), 3.90 (3H, s), 3.93 (3H, s), 3.97 (3H, s), 4.04 (1H, d, J=13.2 Hz), 4.72 (1H, d, J=13.2 Hz), 5.08 (1H, d, J=4.4 Hz), 5.56 (1H, d, J=4.4 Hz), 6.83 (1H, s), 7.01 (1H, s), 7.30 (1H, s), 7.81 (1H, s).

SIMS (M/Z): 672 (M+1)$^+$.

IR (KBr, cm$^{-1}$): 1740, 1620.

EXAMPLE 54

6,7-Dihydroxy-2-methylthio-4-oxo-4H-1-benzothiopyran

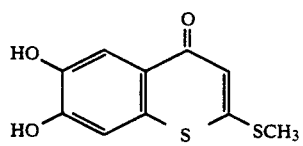

To a solution of 2.31 g (8.61 mmol) of the compound of Example 48 in 28 ml of dried dichloromethane was added a solution of 3.67 g (14.8 mmol) of boron tribromide in 9 ml of dichloromethane at −78° C., and the mixture was stirred overnight at room temperature. To the solution were added 31 ml of ice-water at 0° C. pH was brought to 11 with 1N aqueous solution of sodium hydroxide and the solution was washed with ether. The aqueous layer was made acidic with 1N hydrochloric acid. The crystals deposited were collected by filtration, washed with water, and dried to obtain 1.64 g (6.83 mmol) of title compound (yield 79%).

MS (M/Z): 240 (M+).

EXAMPLE 55

6,7-Isopropylidenedioxy-2-methylthio-4-oxo-4H-1-benzothiopyran

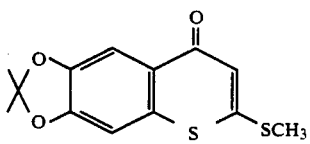

A mixture of 97.4 mg (0.405 mmol) of the compound of Example 54, phosphorous pentoxide, acetone and benzene was refluxed under heat for 21 hours at 120° C. After distilled off the solvents, dichloromethane was added. The organic layer was washed with saturated sodium bicarbonate solution and with saturated saline solution, dried over anhydrous sodium sulfate, and solvent was distilled off. The residue was purified by means of silica gel column chromatography (CHCl$_3$-AcOEt 10:1) to obtain 41 mg (0.146 mmol) of title compound (yield 36%).

$^1$H-NMR (90 MHz, CDCl$_3$, δ): 1.73 (6H, s), 2.60 (3H, s), 6.78 (1H, s), 6.81 (1H, s), 7.77 (1H, s),

Ms (M/Z): 280 (M+).

EXAMPLE 56

6,7-Isopropylidenedioxy-2-methylsulfinyl-4-oxo-4H-1-benzothiopyran

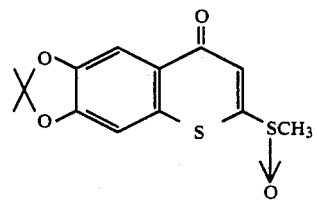

Similarly to Example 18, 345 mg of title compound were obtained from 297 mg (1.06 mmol) of the compound of Example 55.

$^1$H-NMR (90 MHz, CDCl$_3$, δ): 1.75 (6H, s), 2.95 (3H, s), 6.96 (1H, s), 7.19 (1H, s), 7.80 (1H, s).

MS (M/Z): 296 (M+).

EXAMPLE 57

6,7-Isopropylidenedioxy-2-mercapto-4-oxo-4H-1-benzothiopyran

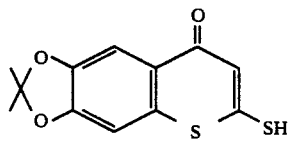

Similarly to Example 19, 280 mg of title compound were obtained from 345 mg (1.16 mmol) of the compound of Example 56.

MS (M/Z): 266 (M+).

EXAMPLE 58 p-Methoxybenzyl 3-(6,7-isopropylidenedioxy-4-oxo-4H-1-benzothiopyran-2-yl)thiomethyl-7-[(Z)-2-methoxyimino-2-(2-tritylaminothiazole-4-yl)acetamido]-3-cephem-4-carboxylate 1-oxide

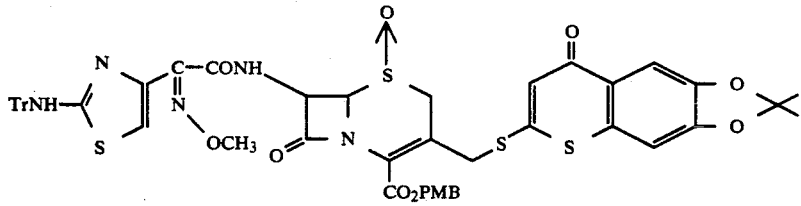

Similarly to Example 20, 634 mg (0.609 mmol) of title compound were obtained from 726 mg (0.895 mmol) of the compound of Example 1 and 239 mg (0.896 mmol) of the compound of Example 57 (yield 71%).

$^1$H-NMR (400 MHz, CDCl$_3$, δ): 1.73 (6H, s), 3.45 (1H, d, J=18.4 Hz), 3.66 (1H, d, J=14.2 Hz), 3.73 (1H, d, J=18.4 Hz), 3.79 (3H, s), 4.07 (3H, s), 4.50 (1H, d, J=4.9 Hz), 4.90 (1H, d, J=14.2 Hz), 5.12 (1H, d, J=11.7 Hz), 5.21 (1H, d, J=11.7 Hz), 6.11 (1H, dd, J=4.9, 10.3 Hz), 6.68 (1H, s), 6.7–7.4 (21H, m), 7.76 (1H, s).

EXAMPLE 59 p-Methoxybenzyl 3-(6,7-isopropylidenedioxy-4-oxo-4H-1-benzothiopyran-2-yl)thiomethyl-7-[(Z)-2-methoxyimino-2-(2-tritylaminothiazole-4-yl)acetamide]-3-cephem-4-carboxylate

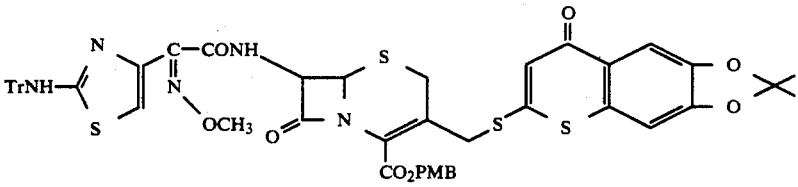

Similarly to Example 3, 328 mg (0.321 mmol) of title compound were obtained from 630 mg (0.606 mmol) of the compound of Example 58 (yield 53%).

$^1$H-NMR (400 MHz, CDCl$_3$, δ): 1.73 (6H, s), 3.40 (1H, d, J=18.6 Hz), 3.70 (1H, d, J=18.6 Hz), 3.79 (3H, s), 3.95 (1H, d, J=13.5 Hz), 4.07 (3H, s), 4.37 (1H, d, J=13.5 Hz), 5.00 (1H, d, J=4.9 Hz), 5.10 (1H, d, J=11.7 Hz), 5.18 (1H, d, J=11.7 Hz), 5.88 (1H, dd, J=4.9, 8.3 Hz), 6.72 (1H, s), 6.74 (1H, s), 6.8–6.9 (3H, m), 6.99 (1H, s), 7.01 (1H, s), 7.26–7.29 (15H, m), 7.77 (1H, s).

EXAMPLE 60

Sodium 7β-[(Z)-2-(2-aminothiazole-4-yl)-2-methoxyiminoacetamido]-3-(6,7-isopropylidenedioxy-4-oxo-4H-1-benzothiopyran-2-yl)thiomethyl-3-cephem-4-carboxylate

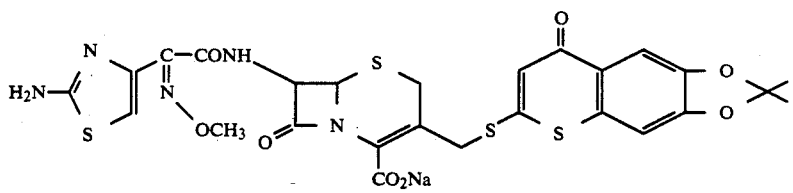

Similarly to Example 4, 38.6 mg (0.0565 mmol) of title compound were obtained from 137 mg (0.134 mmol) of the compound of Example 59 (yield 42%).

$^1$H-NMR (400 MHz, CD$_3$OD, δ): 1.64 (6H, s), 3.31 (1H, d, J=17.3 Hz), 3.66 (1H, d, J=17.3 Hz), 3.87 (3H, s), 3.93 (1H, d, J=13.2 Hz), 4.59 (1H, d, J=13.2 Hz), 4.97 (1H, d, J=4.9 Hz), 5.65 (1H, d, J=4.9 Hz), 6.73 (1H, s), 6.90 (1H, s), 7.05 (1H, s), 7.55 (1H, s),

EXAMPLE 61

6,7-Methylenedioxy-2-methylthio-4-oxo-4H-1-benzothiopyran

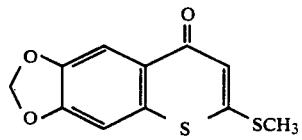

Similarly to Example 23, 99.9 mg (0.396 mmol) of title compound were obtained from 300 mg (1.23 mmol) of 2'-bromo-4',5'-methylenedioxyacetophenone (yield 32%).

$^1$H-NMR (90 MHz, CDCl$_3$, δ): 2.61 (3H, s), 6.09 (2H, s), 6.82 (1H, s), 6.87 (1H, s), 7.85 (1H, s),

MS (M/Z): 252 M$^+$.

EXAMPLE 62

6,7-Methylenedioxy-2-methylsulfinyl 4-oxo-4H-1-benzothiopyran

EXAMPLE 64 p-Methoxybenzyl 3-(6,7-methylenedioxy-4-oxo-4H-1benzothiopyran-2-yl)thiomethyl-7-[(Z)-2-2-trityloxyaminothiazole-4-yl)-2-trityloxyiminoacetamido]-3-cephem-4-carboxylate 1-oxide

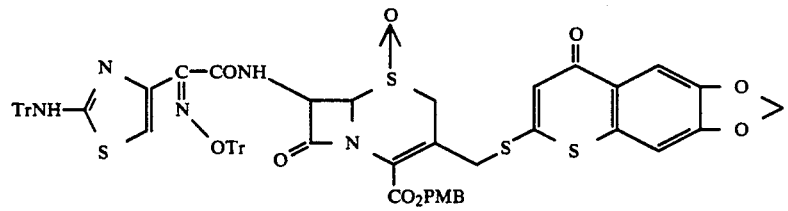

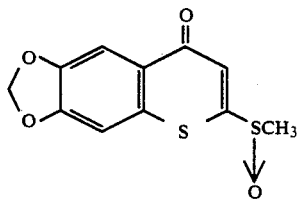

Similarly to Example 18, 1.72 g (6.41 mmol) of title compound were obtained from 2.00 g (7.93 mmol) of the compound of Example 61 (yield 81%).
MS (M/Z): 268 (M+).

Similarly to Example 20, 341 mg (0.279 mmol) of title compound were obtained from 900 mg (0.867 mmol) of p-methoxybenzyl 3-chloromethyl-7-[(Z)-2-(tritylaminothiazole-4-yl)-2-trityloxyiminoacetamido]-3-cephem-4-carboxylate 1-oxide and the compound of Example 63 (yield 32%).

$^1$H-NMR (400 MHz, CDCl$_3$, δ): 3.14 (1H, d, J=19.0 Hz), 3.45 (1H, d, J=19.0 Hz), 3.63 (1H, d, J=14.0 Hz), 3.80 (3H, s), 4.36 (1H, d, J=4.9 Hz), 4.84 (1H, d, J=14.0 Hz), 5.14 (1H, d, J=11.7 Hz), 5.21 (1H, d, J=11.7 Hz), 6.11 (2H, s), 6.24 (1H, d, J=4.9, 10.3 Hz), 6.76 (1H, s), 6.9–7.4 (36H, m), 7.84 (1H, s).

EXAMPLE 63

6,7-Methylenedioxy-2-mercapto-4-oxo-4H-1-benzothiopyran

EXAMPLE 65 p-Methoxybenzyl 3-(6,7-methylenedioxy-4-oxo-4H-1-benzothiopyran-2-yl)thiomethyl-7-[(Z)-2-(2-tritylaminothiazole-4-yl)-2-trityloxyiminoacetamido]-3-cephem-4-carboxylate

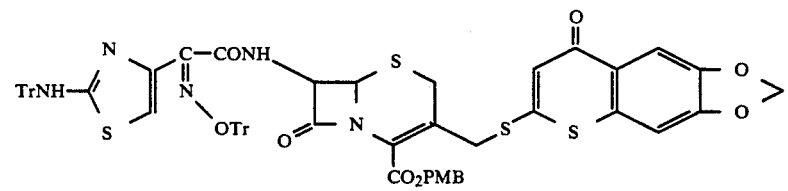

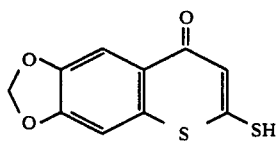

Similarly to Example 19, 1.20 g (5.04 mmol) of title compound were obtained from 1.72 g (6.41 mmol) of the compound of Example 62 (yield 79%).
MS (M/Z): 238 (M+)

Similarly to Example 3, 341 mg (0.279 mmol) of title compound were obtained rom 437 mg (0.352 mmol) of the compound of Example 64 (yield 79%).

$^1$H-NMR (400 MHz, CDCl$_3$, δ): 3.24 (1H, d, J=18.1 Hz), 3.60 (1H, d, J=18.1 Hz), 3.79 (3H, s), 3.94 (1H, d, J=13.5 Hz), 4.34 (1H, d, J=13.5 Hz), 5.01 (1H, d, J=4.9 Hz), 5.13 (1H, d, J=12.2 Hz) 5.18 (1H, d, J=12.2 Hz) 6.00 (1H, dd, J=4.9, 8.8 Hz), 6.10 (2H, s), 6.4–7.9 (38H, m).

EXAMPLE 66

Sodium 7β-[(Z)-2-(2-aminothiazole-4-yl)-2-hydroxyiminoacetamido]-3-6,7-methylenedioxy-4-oxo-4H-1-benzothiopyran-2-yl)thiomethyl-3-cephem-4-carboxylate

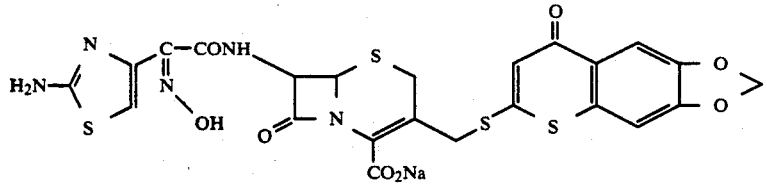

Similarly to Example 4, 109 mg (0.169 mmol) of title compound were obtained from 335 mg (0.274 mmol) of the compound of Example 65 (yield 62%).

$^1$H-NMR (400 MHz, CD$_3$OD, δ): 3.40 (1H, d, J=17.6 Hz), 3.75 (1H, d, J=17.6 Hz), 4.04 (1H, d, J=13.5 Hz), 4.67 (1H, d, J=13.5 Hz), 5.09 (1H, d, J=4.4 Hz), 5.78 (1H, d, J=4.4 Hz), 6.15 (2H, s), 6.77 (1H, s), 6.99 (1H, s) 7.23 (1H, s), 7.72 (1H, s).

IR (KBr, cm$^{-1}$): 1750, 1590.

EXAMPLE 67 p-Methoxybenzyl 3-(6,7-methylenedioxy-4-oxo-4H-1-benzothiopyran-2-yl)thiomethyl-7-[(Z)-2-methoxyimino-2-(2-tritylaminothiazole-4-yl)acetamido]-3-cephem-4-carboxylate 1-oxide

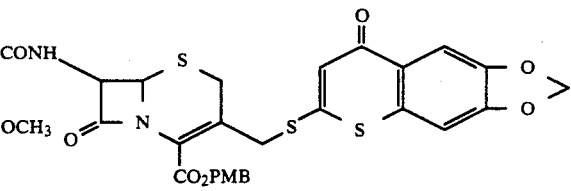

Similarly to Example 20, 511 mg (0.504 mmol) of title compound were obtained from 700 mg (0.864 mmol) of the compound of Example 1 and 226 mg (0.950 mmol) of the compound of Example 63 (yield 58%).

$^1$H-NMR (400 MHz, CDCl$_3$, δ): 34.5 (1H, d, J=18.4 Hz), 3.68 (1H, d, J=14.2 Hz), 3.74 (1H, d, J=18.4 Hz), 3.79 (3H, s), 4.07 (3H, s), 4.51 (1H, d, J=4.4 Hz), 4.87 (1H, d, J=14.2 Hz), 5.13 (1H, d, J=11.7 Hz), 5.19 (1H, d, J=11.7 Hz), 6.10 (2H, s), 6.1–6.2 (1H, m), 6.68 (1H, s), 6.8–7.3 (21H, m), 7.83 (1H, s).

EXAMPLE 68 p-Methoxybenzyl 3-(6,7-methylenedioxy-4-oxo-4H-1-benzothiopyran-2-yl)thiomethyl-7-[(Z)-2-methoxyimino-2-(2-tritylaminothiazole-4-yl)acetamido]-3-cephem-4-carboxylate

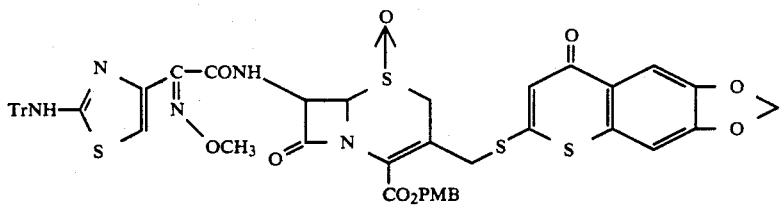

Similarly to Example 3, 424 mg (0.425 mmol) of title compound were obtained from 506 mg (0.500 mmol) of the compound of Example 67 (yield 85%), $^1$H-NMR (400 MHz, CDCl$_3$, δ): 3.41 (1H, d, J=18.1 Hz), 3.70 (1H, d, J=18.1 Hz), 3.79 (3H, s), 3.97 (1H, d, J=13.5 Hz), 4.07 (3H, s), 4.34 (1H, d, J=13.5 Hz), 5.00 (1H, d, J=4.9 Hz), 5.11 (1H, d, J=12.0 Hz), 5.16 (1H, d, J=12.0 Hz), 5.88 (1H, dd, J=4.9, 8.8 Hz), 6.10 (2H, s), 6.7–7.3 (23H, m).

EXAMPLE 69

Sodium 7β-[(Z)-2-(2-aminothiazole-4-yl)-2-methoxyiminoacetamido]-3-(6,7-methylenedioxy-4-oxo-4H-1-benzothiopyran-2-yl)thiomethyl-3-cephem-4-carboxylate

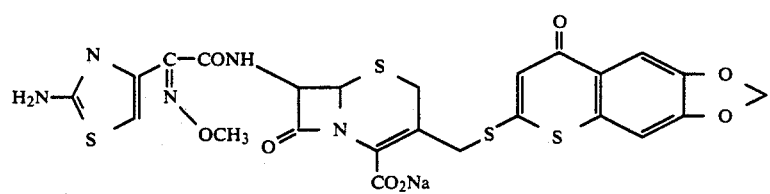

Similarly to Example 4, 131 mg (0.199 mmol) of title compound were obtained from 419 mg (0.421 mmol) of the compound of Example 68 (yield 47%).

¹H-NMR (400 MHz, CD₃OD, δ): 3.41 (1H, d, J=17.4 Hz), 3.75 (1H, d, J=17.4 Hz), 3.96 (3H, s), 4.04 (1H, d, J=13.5 Hz), 4.67 (1H, d, J=13.5 Hz), 5.07 (1H, d, J=4.9 Hz), 5.75 (1H, d, J=4.9 Hz), 6.15 (2H, s), 6.83 (1H, s), 7.00 (1H, s), 7.23 (1H, s), 7.72 (1H, s).

IR (KBr, cm⁻¹): 1750, 1590.

EXAMPLE 70

6,7-Di-tert-butoxycarbonyloxy-2-methylthio-4-oxo-4H-1-benzothiopyran

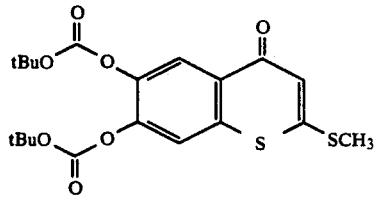

To a suspension of 300 mg (1.25 mmol) of the compound of Example 54 in 10 ml of dichloromethane were added 21.4 mg (0.175 mmol) of 4-dimethylaminopyridine and 599 mg (2.75 mmol) of di-tert-butyl dicarbonate at room temperature and the mixture was stirred for 30 minutes. Solvent was concentrated and the residue was purified by means of silica gel column chromatography (CHCl₃-AcOEt 40:1) to obtain 319 mg (0.725 mmol) of title compound (yield 58%).

Melting point: 110°–111° C.

Elemental analysis (1%): As $C_{20}H_{24}O_7S_2$; Calculated C:54.53;H:5.49; Observed C:54.61; H:5.46;

¹H-NMR (90 MHz, CDCl₃, δ): 1.55 (18H, s), 2.61 (3H, s), 6.82 (1H, s), 7.48 (1H, s), 8.32 (1H, s).

MS (M/Z): 440 (M+).

EXAMPLE 71

6,7-Di-tert-butoxycarbonyloxy-2-methylsulfinyl-4-oxo-4H-1-benzothiopyran

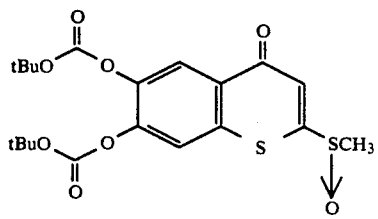

Similarly to Example 18, 310 mg of title compound were obtained from 276 mg (0.625 mmol) of the compound of Example 70.

¹H - NMR (400 MHz, CDCl₃, δ): 1.57 (18H, s), 2.96 (3H, s), 7.25 (1H, s), 7.69 (1H, s), 8.40 (1H, s).

EXAMPLE 72

6,7-Di-tert-butoxycarbonyloxy-2-mercapto-4-oxo-4H-1-benzothiopyran

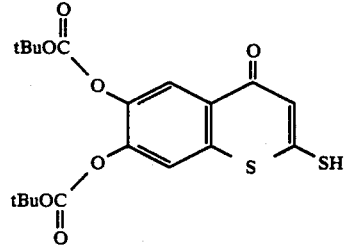

Similarly to Example 19, 241 mg (0.564 mmol) of title compound were obtained from 310 mg (0.678 mmol) of the compound of Example 71 (yield 83%).

¹H - NMR (400 MHz, CDCl₃, δ): 1.57 (18H, s), 7.18 (1H, s), 7.38 (1H, s), 8.13 (1H, s).

EXAMPLE 73 p-Methoxybenzyl 3-(6,7-di-tert-butoxycarbonyloxy-4-oxo-4H-1-benzothiopyran-2-yl) thiomethyl-7-[(Z)-2-methoxyimino-2-(2-tritylaminothiazole-4-yl) acetamido]-3-cephem-4-carboxylate 1-oxide

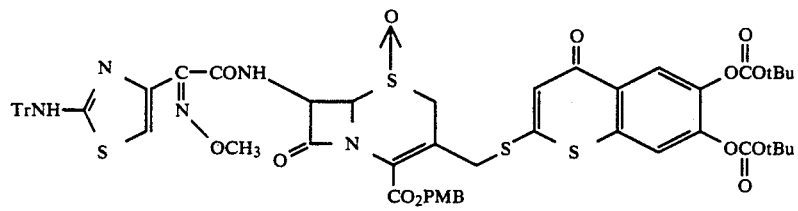

Similarly to Example 20, 783 mg (0.652 mmol) of title compound were obtained from 834 mg (1.03 mmol) of the compound of Example 1 and 483 mg (1.13 mmol) of the compound of Example 72 (yield 63%).

¹H - NMR (400 MHz, CDCl₃, δ): 1.57 (18H, s), 3.41 (1H, d, J=18.6 Hz), 3.7–3.8 (2H, m), 3.78 (3H, s), 4.07 (3H, s), 4.52 (1H, d, J=4.9 Hz), 4.84 (1H, d, J=14.2 Hz), 5.16 (1H, d, J=11.7 Hz), 5.25 (1H, d, J=11.7 Hz), 6.13 (1H, dd, J=4.9, 10.0 Hz), 6.69 (1H, s), 6.9–7.4 (21H, m), 8.32 (1H, s).

EXAMPLE 74 p-Methoxybenzyl 3-(6,7-di-tert-butoxycarbonyloxy-4-oxo-4H-1-benzothiopyran-2-yl) thiomethyl-7-[(Z)-2-methoxyimino-2-(2-tritylaminothiazole-4-yl) acetamido]-3-cephem-4-carboxylate

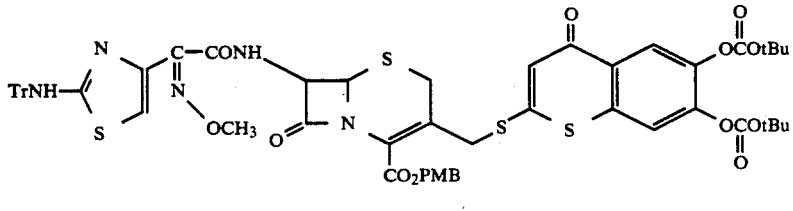

Similarly to Example 3, 484 mg (0.408 mmol) of title compound were obtained from 778 mg (0.648 mmol) of the compound of Example 73 (yield 63%).

$^1$H - NMR (400 MHz, CDCl$_3$, δ): 1.56 (18H, s), 3.41 (1H, d, J=18.1 Hz), 3.68 (1H, d, J=18.1 Hz), 3.77 (3H, s), 4.02 (1H, d, J=13.5 Hz), 4.07 (3H, s), 4.34 (1H, d, J=13.5 Hz), 5.01 (1H, d, J=4.9 Hz), 5.13 (1H, d, J=11.7 Hz), 5.21 (1H, d, J=11.7 Hz), 5.89 (1H, dd, J=4.9, 8.8 Hz), 6.73 (1H, s), 6.8–7.4 (21H, m), 8.33 (1H, s).

EXAMPLE 75

Sodium 7β-[(Z)-2-(2-aminothiazole-4-yl)-2-methoxyiminoacetamido]-3-(6,7-dihydroxy-4-oxo-4H-1-benzothiopyran-2-yl) thiomethyl-3-cephem-4-carboxylate

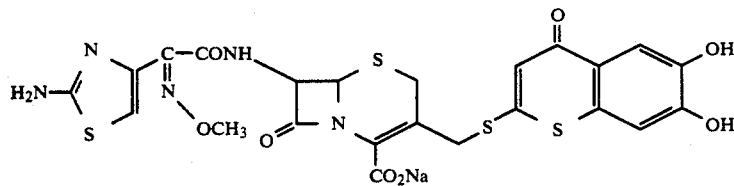

Similarly to Example 4, 96.8 mg (0.150 mmol) of title compound were obtained from 266 mg (0.224 mmol) of the compound of Example 74 (yield 67%).

$^1$H - NMR (400 MHz, CD$_3$OD, δ): 3.40 (1H, d, J=17.4 Hz), 3.75 (1H, d, J=17.4 Hz), 3.96 (3H, s), 4.02 (1H, d, J=13.7 Hz), 4.66 (1H, d, J=13.7 Hz), 5.07 (1H, d, J=4.9 Hz), 5.75 (1H, d, J=4.9 Hz), 6.83 (1H, s), 6.94 (1H, s), 7.00 (1H, s), 7.71 (1H, s).

IR (KBr, cm$^{-1}$): 1750, 1550.

EXAMPLE 76 p-Methoxybenzyl 3-(6,7-di-tert-butoxycarbonyloxy-4-oxo-4H-1-benzothiopyran-2-yl) thiomethyl-7-[(Z)-2-(2-tritylaminothiazole-4-yl)-2-trityloxyiminoacetamido)-3-cephem-4-carboxylate 1-oxide

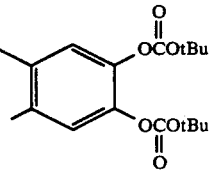

Similarly to Example 20, 461 mg (0.323 mmol) of title compound were obtained from 1.07 g (1.03 mmol) of p-methoxybenzyl 3-chloromethyl-7-[(Z)-2-trityloxyimino-2-(tritylaminothiazole-4-yl) acetamido]-3-cephem-4-carboxylate 1-oxide and 483 mg (1.13 mmol) of the compound of Example 72 (yield 31%).

$^1$H - NMR (400 MHz, CDCl$_3$, δ): 1.57 (18H, s), 3.12 (1H, d, J=18.4 Hz), 3.47 (1H, d, J=18.4 Hz), 3.71 (1H, d, J=14.2 Hz), 3.78 (3H, s), 4.39 (1H, d, J=4.9 Hz), 4.82 (1H, d, J=14.2 Hz), 5.17 (1H, d, J=11.7 Hz), 5.27 (1H, d, J=11.7 Hz), 6.26 (1H, d, J=4.9, 10.3 Hz), 6.87 (1H, s), 6.9–7.4 (36H, m), 8.33 (1H, s).

EXAMPLE 77 p-Methoxybenzyl 3-(6,7-di-tert-butoxycarbonyloxy-4-oxo-4H-1-benzothiopyran-2-yl) thiomethyl-7-[(Z)-2-(2-tritylaminothiazole-4-yl)-2-trityloxyiminoacetamido]-3-cephem-4-carboxylate

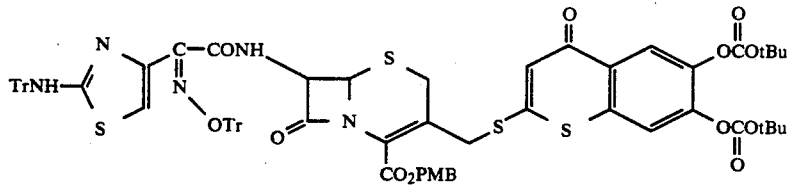

Similarly to Example 3, 353 mg (0.250 mmol) of title compound were obtained from 457 mg (0.320 mmol) of the compound of Example 76 (yield 78%).

$^1$H - NMR (400 NHz, CDCl$_3$, δ): 1.56 (18H, s), 3.23 (1H, d, J=18.4 Hz), 3.59 (1H, d, J=18.4 Hz), 3.77 (3H, s), 3.98 (1H, d, J=12.7 Hz), 4.34 (1H, d, J=12.7 Hz), 5.02 (1H, d, J=4.9 Hz), 5.14 (1H, d, J=11.7 Hz), 5.23 (1H, d, J=11.7 Hz), 6.01 (1H, dd, J=4.9, 8.8 Hz), 6.86 (1H, s), 6.9–7.4 (36H, m), 8.32 (1H, s).

EXAMPLE 78

Sodium 7β-[(Z)-2-(2-aminothiazole-4-yl)-2-hydroxyiminoacetamido]-3-(6,7-dihydroxy-4-oxo-4H-1-benzothiopyran-2-yl)thiomethyl-3-cephem-4-carboxylate

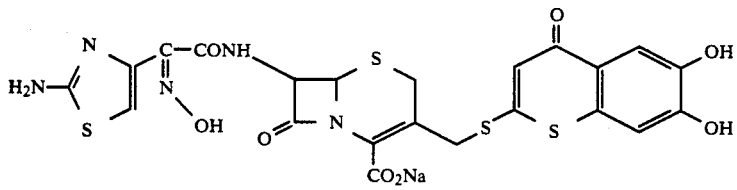

Similarly to Example 4, 101 mg (0.160 mmol) of title compound were obtained from 349 mg (0.247 mmol) of the compound of Example 77 (yield 65%).

$^1$H - NMR (400 MHz, CD$_3$OD, δ): 3.40 (1H, d, J=17.4 Hz), 3.73 (1H, d, J=17.4 Hz), 4.06 (1H, d, J=13.0 Hz), 4.55 (1H, d, J=13.0 Hz), 5.08 (1H, d, J=4.9 Hz), 5.78 (1H, d, J=4.9 Hz), 6.76 (1H, s), 6.84 (1H, s), 6.91 (1H, s), 7.64 (1H, s).

IR (KBr, cm$^{-1}$):1750, 1540.

SIMS (M/Z):630 (M+1)$^+$.

EXAMPLE 79

2-Bromo-3-chloro-4,5-dimethoxybenzaldehyde

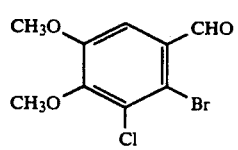

Into 50 ml of acetonitrile were suspended 5.39 g (20.3 mmol), of 6-bromo-5-chlorovanillin, and 3.04 ml (20.3 mmol) of 1.8-diazabicyclo[5,4,0]-7-undecene and 2.53 ml (40.6 mmol) of methyl iodide were added dropwise under cooling with ice. After stirred for 5 hours at room temperature, 3.9 ml (22.33 mmol) if diisopropylethylamine and 2.53 ml (40.6 mmol) of methyl iodide were added under cooling with ice and the mixture was stirred for 20 hours at room temperature. After distilled off the solvent, 200 ml of dichloromethane were added to the residue, which was washed with water. After dried over anhydrous magnesium sulfate, the concentrated residue was purified by means of silica gel column chromatography (hexane-AcOEt 5:1) to obtain 4.04 g (yield 71%) of title compound as colorless needle-like crystals.

Melting point: 118.5°–119.1° C.

$^1$H - NMR (90 MHz, CDCl$_3$, δ): 3.93 (3H, s), 3.96 (3H, s), 7.44 (1H, s), 10.28 (1H, s).

Elemental analysis (%): As C$_9$H$_8$Br ClO$_3$; Calculated C:38.67;H:2.88; Observed C:38.65;H:2.75

EXAMPLE 80

2-Bromo-3-chloro-4,5-dimethoxyacetophenone

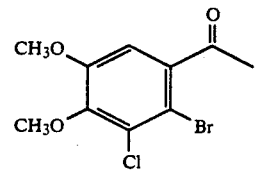

To a solution of 3.90 g (14 mmol) of the compound of Example 79 was added dropwise Grignard's reagent prepared from 3.40 g (14 mmol) of magnesium, 1.05 ml (16.8 mmol) of methyl iodide and 5.7 ml of diethyl ether under cooling with ice. After stirred for 40 minutes at room temperature, 8.5 ml of saturated aqueous solution of NH$_4$Cl were added and the mixture was stirred further for 10 minutes. The organic layer was separated and the aqueous layer was extracted with ether (50 ml×2). The organic layers were combined, washed with saturated saline solution, and then dried over anhydrous magnesium sulfate. The concentrated residue was purified by means of silica gel column chromatography (hexane-AcOEt 4.1) to obtain pale yellow powder. After dissolved the pale yellow powder obtained into 2.7 ml of dichloromethane, 55 ml of dichloromethane containing 4.81 g (22.32 mmol) of pyridinium chlorochromate and 5.58 g of molecular-sieve powder were added dropwise. After stirred the mixture for 50 minutes at room temperature, the organic layer was separated. To the residue were added 50 ml of diethyl ether, and the mixture was stirred violently, then the ether layer was separated. This procedure was repeated thrice and the ether layers and previous dichloromethane layer were combined, which was washed with saturated sodium bicarbonate solution and with saturated saline solution. After dried over anhydrous magnesium sulfate, the concentrated residue was purified by means of silica gel column chromatography (hexane-AcOEt 4:1) to obtain 2.86 g (yield 70%) of title compound as pale yellow powder.

$^1$H - NMR (90 MHz, CDCl$_3$, δ): 2.64 (3H, s), 3.88 (6H, s), 6.88 (1H, s).

EXAMPLE 81

8-Chloro-6,7-dimethoxy-2-methylthio-4-oxo-4H-1-benzothiopyran

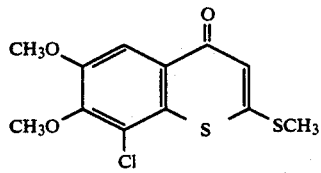

Similarly to Example 17, 2.50 g (yield 85%) of title compound were obtained as white powder from 2.85 g (9.70 mmol) of the compound of Example 80.

$^1$H - NMR (90 MHz, CDCl$_3$, δ): 2.65 (3H, s), 3.98 (6H, s), 6.84 (1H, s), 7.93 (1H, s).

EXAMPLE 82

8-Chloro-6,7-dihydroxy-2-methylthio-4-oxo-4H-1-benzothiopyran

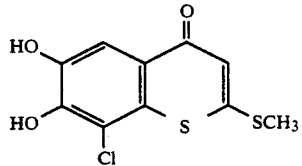

Similarly to Example 54, 0.947 g (yield 52%) of title compound were obtained as pale yellow powder from 2.03 g (6.69 mmol) of the compound of Example 81.

$^1$H - NMR (90 MHz, DMSO-d$_6$, δ): 2.69 (3H, s), 6.76 (1H, s), 7.70 (1H, s).

EXAMPLE 83

8-Chloro-6,7-di-tert-butoxycarbonyloxy-2-methylthio-4-oxo-4H-1-benzothiopyran

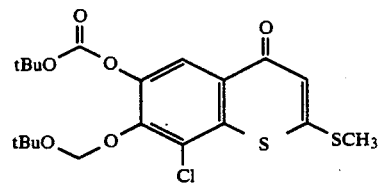

Similarly to Example 70, 1.43 g (yield 87%) of title compound were obtained as colorless oil from 0.947 g (3.45 mmol) of the compound of Example 82.

$^1$H - NMR (400 MHz, CDCl$_3$, δ): 1.55 (9H, s), 1.57 (9H, s), 2.66 (3H, s), 6.84 (1H, s), 8.33 (1H, s).

EXAMPLE 84

8-Chloro-6,7-di-tert-butoxycarbonyloxy-2-methylsulfinyl-4-oxo-4H-1-benzothiopyran

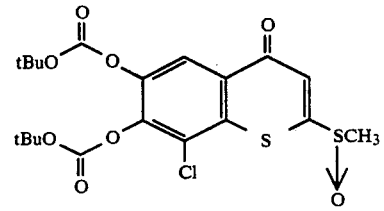

Similarly to Example 18, 1.40 g (yield 99%) of title compound were obtained as white powder from 1.37 g (2.88 mmol) of the compound of Example 83.

$^1$H - NMR (400 MHz, CDCl$_3$, δ): 1.56 (9H, s), 1.58 (9H, s), 2.98 (3H, s), 7.30 (1H, s), 8.40 (1H, s).

EXAMPLE 85 p-Methoxybenzyl 3-(8-chloro-6,7-di-tert-butoxycarbonyl-oxy-4-oxo-4H-1-benzothiopyran-2-yl)thiomethyl-7-[(Z)-methoxyimino-2-(2-trizylaminothiazole-4-yl) acetamido]-3-cephem-4-carboxylate

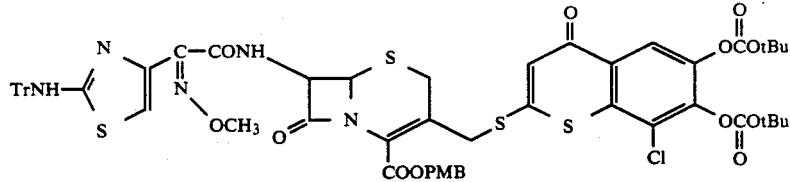

After dissolved 0.446 g (0.912 mmol) of the compound of Example 84 into 5.0 ml of THF, 1.82 ml of 1N aqueous solution of NaSH were added dropwise under cooling with ice and the mixture was stirred for 1 hour at room temperature. The reaction liquor was concentrated under reduced pressure and the residue was dissolved into 2.0 ml of dimethylformamide. Under cooling with ice, pH was adjusted to 3.0 using 3N HCl to obtain an orange solution (liquor A). Into 1.5 ml of dimethylformamide were dissolved 0.60 g (0.76 mmol) of p-methoxybenzyl 3-chloromethyl-7-[(Z)-2-methoxyimino-2-(2-tritylaminothiazole-4-yl) acetamido]-3-cephem-4-carboxylate, and, after added 136.8 mg (0.912 mmol) of sodium iodide under cooling with ice, the mixture was stirred for 30 minutes at room temperature. Then, previous liquor A was added to this reaction liquor under cooling with ice and the mixture was stirred for 1 hour at room temperature. The reaction liquor was poured into 40 ml of ice-water and the deposits were collected by filtration. The deposits thus obtained were dissolved into 200 ml of dichloromethane, which was washed with water and then with saturated saline solution. After dried over anhydrous magnesium sulfate, the concentrated residue was purified through column (MeOH-CH$_2$Cl$_2$ 1.99) to obtain 0.290 g (yield 31%) of title compound as pale yellow caramel.

$^1$H - NMR (400 MHz, CDCl$_3$, δ): 1.56 (9H, s), 1.57 (9H, s), 3.56 (2H, ABq, J=18.1 Hz), 3.77 (3H, s), 4.21 (2H, ABq, J=13.2 Hz), 4.07 (3H, s), 5.02 (1H, d, J=4.9 Hz), 5.18 (2H, ABq, J=11.7 Hz), 5.89 (1H, dd, J=4.9, 9.3 Hz), 6.73 (1H, s), 6.85 (2H, d, J=8.8 Hz) 6.98 (1H, s), 7.28-7.31 (17H, m), 8.33 (1H, s).

EXAMPLE 86

Sodium 7β-[(Z)-2-(2-aminothiazole-4-yl)-2-methoxy-iminoacetamido]-3-(8-chloro-6,7-dihydroxy-4-oxo-4H-1-benzothiopyran-2-yl)thiomethyl-3-cephem-4-carboxylate

EXAMPLE 87 p-Methoxybenzyl 7-[(Z)-2-tert-butoxycarbonylmethoxyimino-2-(2-tritylaminothiazole-4-yl) acetamido]-3-(8-chloro-6,7-di-tert-butoxycarbonyloxy-4-oxo-4H-1-benzothiopyran-2-yl)thiomethyl-3-cephem-4-carboxylate

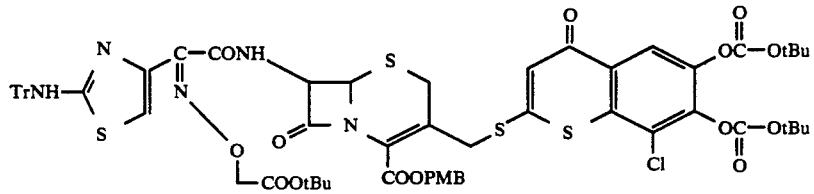

Similarly to Example 85, 0.177 g (yield 52%) of title compound were obtained as pale yellow caramel using 0.151 g (0.307 mmol) of the compound of Example 84 and 0.229 g (0.256 mmol) of p-methoxybenzyl 7-[(Z)-2-tert-butoxycarbonylmethoxyimino-2-(2-tritylamino-thiazole-4-yl) acetamide]-3-chloromethyl-3-cephem-4-carboxylate.

$^1$H - NMR (400 MHz, CDCl$_3$, δ): 1.44 (9H, s), 1.56 (9H, s), 1.57 (9H, s), 3.52 (2H, ABq, J=18.1 Hz), 3.77 (3H, s), 4.20 (2H, ABq, J=13.2 Hz), 4.76 (2H, ABq, J=17.1 Hz), 5.01 (1H, d, J=4.9 Hz), 5.18 (2H, ABq, J=11.7 Hz), 5.87 (1H, dd, J=4.9, 8.8 Hz), 6.80 (1H, s), 6.85 (2H, d, J=8.3 Hz), 6.96 (1H, s), 7.27-7.32 (17H, m), 8.33 (1H, s), 8.70 (1H, d, J=8.8 Hz).

EXAMPLE 88

Disodium 7β-[(Z)-2-(2-aminothiazole-4-yl)-2-carboxymethoxy-yiminoacetamido]-3-(8-chloro-6,7-dihydroxy-4-oxo-4H-1-benzothiopyran-2-yl)thiomethyl-3-cephem-4-carboxylate

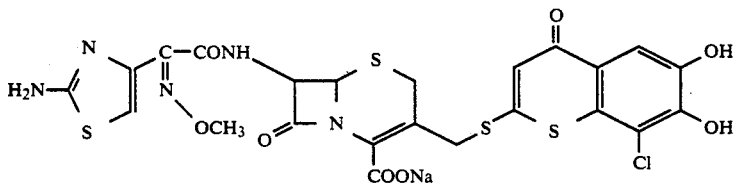

Similarly to Example 4, 71.6 mg (yield 45%) of title compound were obtained as pale yellow powder from 0.284 g (0.233 mmol) of the compound of Example 85.

$^1$H - NMR (400 MHz, D$_2$O, δ): 3.63 (2H, ABq, J=17.6 Hz), 4.18 (2H, ABq, J=13.7 Hz), 3.98 (3H, s), 5.16 (1H, d, J=4.4 Hz), 5.73 (1H, d, J=4.4 Hz), 6.97 (1H, s), 7.00 (1H, s), 7.52 (1H, s).

IR (KBr, cm$^{-1}$):1740, 1600.

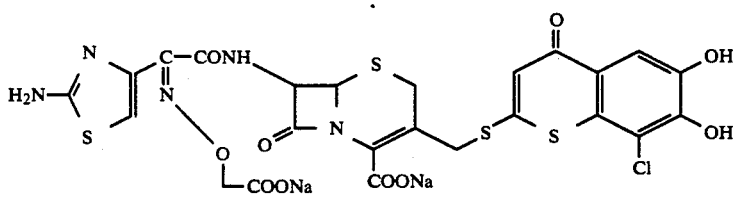

Similarly to Example 4, 87.8 mg (yield 92%) of title compound were obtained as pale yellow powder from 0.169 g (0.128 mmol) of the compound of Example 87.

$^1$H - NMR (400 MHz, D$_2$O, δ): 3.63 (2H, ABq, J=17.6 Hz), 4.22 (2H, ABq, J=13.7 Hz), 4.57 (2H, s), 5.17 (1H, d, J=4.9 Hz), 5.75 (1H, d, J=4.9 Hz), 7.04 (1H, s), 7.05 (1H, s), 7.54 (1H, s).

IR (KBr, cm$^{-1}$): 1760, 1690.

EXAMPLE 89 p-Methoxybenzyl
7-[(Z)-2-(5-amino-1,2,4-thiadiazole-3-yl)-2-methoxyiminoacetamido]-3-(6,7-di-tert-butoxycarbonyloxy-4-oxo-4H-1-benzothiopyran-2-yl)
thiomethyl-3-cephem-4-carboxylate

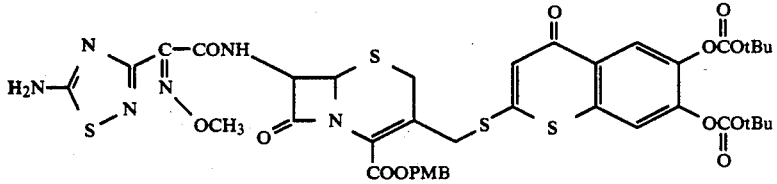

Similarly to Example 85, 0.724 g (yield 85%) of title compound were obtained as pale yellow caramel using 0.493 g (1.08 mmol) of the compound of Example 71 and 0.50 g (0.90 mmol) of p-methoxybenzyl 7-[(Z)-2-(5-amino-1,2,4-thiadiazole-3-yl)-2-methoxyiminoacetamido]-3-chloromethyl-3-cephem-4-carboxylate.

$^1$H - NMR (400 MHz, CDCl$_3$, δ): 1.56 (18H, s), 3.55 (2H, ABq, J=18.6 Hz), 3.76 (3H, s), 4.09 (3H, s), 4.21 (2H, ABq, J=13.2 Hz), 5.06 (1H, d, J=4.9 Hz), 5.16 (2H, ABq, J=11.7 Hz), 6.10 (1H, dd, J=4.9, 8.8 Hz), 6.63 (2H, brs), 6.85 2H, d, J=8.8 Hz), 6.95 (1H, s), 7.29 (2H, d, J=8.8 Hz), 7.44 (1H, s), 8.31 (1H, s), 8.45 (1H, d, J=8.8 Hz).

EXAMPLE 90

Sodium
7β[(Z)-2-(5-amino-1,2,4-thiadiazole-3-yl)-2-methoxyiminoacetamido]-3-(6,7-dihydroxy-4-oxo-4H-1-benzothiopyran-2-yl) thiomethyl-3-cephem-4-carboxylate

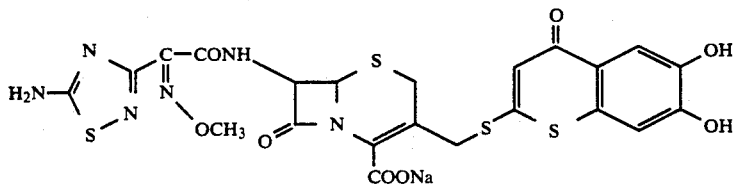

Similarly to Example 4, 191.8 mg (yield 41%) of title compound were obtained as pale yellow powder from 0.691 g (0.73 mmol) of the compound of Example 89.

$^1$H - NMR (400 MHz, CD$_3$OD, δ): 3.56 (2H, ABq, J=17.6 Hz), 4.04 (3H, s), 4.28 (2H, ABq, J=12.7 Hz), 5.07 (1H, d, J=4.9 Hz), 5.79 (1H, d, J=4.9 Hz), 6.71 (1H, s), 6.91 (1H, s), 7.60 (1H, s).

JR (KBr, cm$^{-1}$): 1755, 1590.

EXAMPLE 91 p-Methoxybenzyl
7-[(Z)-2-(5-amino-1,2,4-thiadiazole-3-yl)-2-ethoxyiminoacetamido]-3-(6,7-di-tert-butoxycarbonyloxy-4-oxo-4H-1-benzothiopyran-2-yl) thiomethyl 3-cephem-4-carboxylate

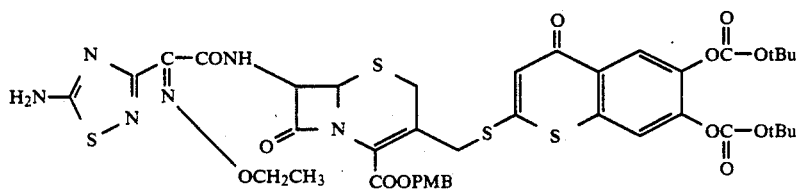

Similarly to Example 85, 0.631 g (yield 75%) of title compound were obtained as pale yellow caramel using 0.482 g (1.06 mmol) of the compound of Example 71 and 0.50 g (0.88 mmol) of p-methoxybenzyl 7-[(Z)-2-(5-amino-1,2,4-thiadiazole-3-yl) -2-ethoxyiminoacetamido]-3-chloromethyl-3-cephem-4-carboxylate.

$^1$H - NMR (400 MHz, CDCl$_3$, δ): 1.32 (3H, t), 1.56 (18H, s), 3.55 (2H, ABq, J=18.1 Hz), 3.77 (3H, s), 4.20 (2H, ABq, J=13.2 Hz), 4.37 (2H, q), 5.06 (1H, d, J=4.9 Hz), 5.16 (2H, ABq, J=11.7 Hz), 6.08 (1H, dd, J=4.9, 9.3 Hz), 6.51 (2H, brs), 6.86 (2H, d, J=8.8 Hz), 6.96 (1H, s), 7.29 (2H, d, J=8.8 Hz), 7.44 (1H, s), 8.05 (1H, d, J=9.3 Hz), 8.32 (1H, s).

EXAMPLE 92

Sodium 7β-[(Z)-2-(5-amino-1,2,4-thiadiazole-3-yl)-2-ethoxyiminoacetamido]-3-(6,7-dihydroxy-4-oxo-4H-1-benzothiopyran-2-yl) thiomethyl-3-cephem-4-carboxylate

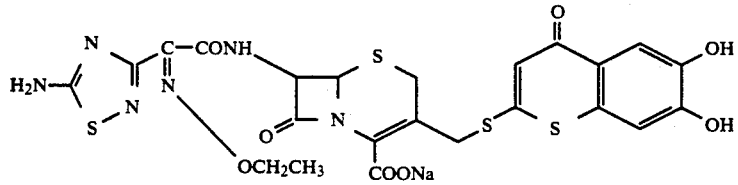

Similarly to Example 4, 171.2 mg (yield 40%) of title compound were obtained as pale yellow powder from 0.620 g (0.647 mmol) of the compound of Example 91.

$^1$H - NMR (400 MHz, CD$_3$OD, δ): 1.34 (3H, t), 3.56 (2H, ABq, J=17.6 Hz), 4.299 (2H, ABq, J=13.2 Hz), 4.304 (2H, q), 5.08 (1H, d, J=4.9 Hz), 5.79 (1H, d, J=4.9 Hz), 6.82 (1H, s), 6.92 (1H, s), 7.64 (1H, s).

IR (KBr, cm$^{-1}$): 1760, 1600.

EXAMPLE 93

3-Bromo-6,7-methylenedioxy-2-methylthio-4-oxo-4H-1-benzothiopyran

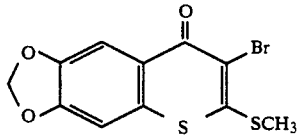

To a suspension of 600 mg (2.38 mmol) of the compound of Example 61 in 6 ml of acetic acid were added 0.227 ml (2.38 mmol) of bromine at room temperature, and the mixture was stirred for 3 hours at 50° C. The crystals deposited were collected by filtration and washed with ethyl acetate to obtain 935 mg of title compound.

$^1$H - NMR (400 MHz, d$_6$DMSO, δ): 2.74 (3H, s), 6.25 (2H, s), 7.58 (1H, s), 7.68 (1H, s).

MS (M/Z) 330 (M+).

EXAMPLE 94

3-Bromo-6,7-dihydroxy-2-methylthio-4-oxo-4H-1-benzothiopyran

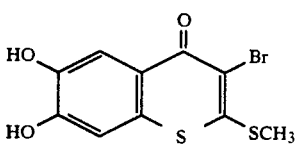

Similarly to Example 54, 232 mg (0.726 mmol) of title compound were obtained from 935 mg (2.82 mmol) of the compound of Example 93 (yield 26%).

$^1$H - NMR (400 MHz, d$_6$DMSO, δ): 2.71 (3H, s), 7.13 (1H, s), 7.70 (1H, s).

MS (M/Z):318 (M+).

EXAMPLE 95

3-Bromo-6,7-di-tert-butoxycarbonyloxy-2-methylthio-4-oxo-4H-1-benzothiopyran

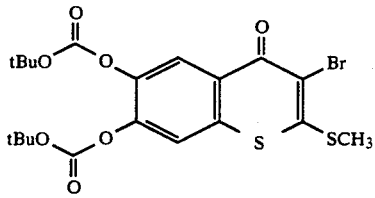

Similarly to Example 70, 189 mg (0.365 mmol) of title compound were obtained from 232 mg (0.726 mmol) of the compound of Example 94 (yield 50%).

$^1$H - NMR (400 MHz, CDCl$_3$, δ): 1.56 (18H, s), 2.68 (3H, s), 7.59 (1H, s), 8.39 (1H, s).

EXAMPLE 96

3-Bromo-6,7-di-tert-butoxycarbonyloxy-2-methylsulfinyl-4-oxo-4H-1-benzothiopyran

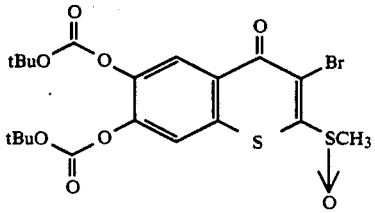

Similarly to Example 18, 204 mg of title compound were obtained from 189 mg (0.365 mmol) of the compound of Example 95.

$^1$H - NMR (400 MHz, CDCl$_3$, δ): 1.57 (18H, s), 3.08 (3H, s), 7.75 (1H, s), 8.43 (1H, s).

EXAMPLE 97 p-Methoxybenzyl 3-(3-bromo-6,7-di-tert-butoxycarbonyloxy-4-oxo-4H-1-benzothiopyran-2-yl) thiomethyl-7-[(Z)-2-methoxyimino-2-(2-tritylaminothiazole-4-yl) acetamido]-3-cephem-4-carboxylate

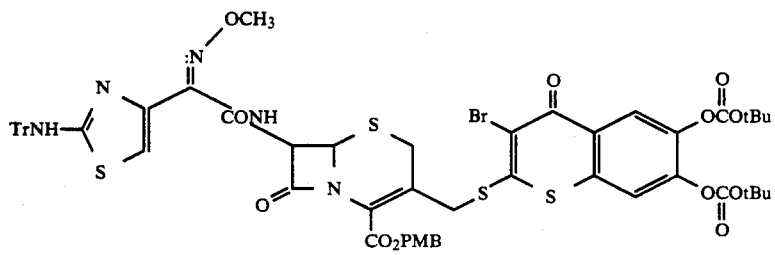

To a solution of 92.8 mg (0.173 mmol) of the compound of Example 96 in 0.9 ml of tetrahydrofuran was added 1N sodium hydrogensulfide (0.358 mmol) at room temperature, and the mixture was stirred for 10 minutes. Solvent was distilled off and a solution of 44.7 mg of sodium bicarbonate in 3.4 ml of water was added to the residue, which was washed with dichloromethane. To the aqueous solution were added 0.7 ml of 1N hydrochloric acid, and the solution was extracted with 1 ml of dichloromethane to obtain dichloromethane solution (liquor A). To a solution of 138 mg (0.173 mmol) of p-methoxybenzyl 3-chloromethyl-7-[(Z)-2-methoxyimino-2-(2-tritylaminothiazole-4-yl) acetamido]-3-cephem-4-carboxylate in 0.4 ml of dimethylformamide were added 31.2 mg (1.12 mmol) of sodium iodide, and the mixture was stirred for 1 hour (liquor B).

Liquor A was added to liquor B under cooling with ice and the mixture was stirred for 2 hours, which was poured into ice-water and extracted with dichloromethane. The organic layer was washed with water and with saturated saline solution, dried over anhydrous sodium sulfate, and then solvent was distilled off. The residue was purified by means of silica gel column chromatography (dichloromethane-ethyl acetate 20:1) to obtain 54.0 mg (0.0428 mmol) of title compound (yield 25%).

$^1$H - NMR (400 MHz, CDCl$_3$, δ): 1.57 (18H, s), 3.44 (1H, d, J=18.1 Hz), 3.70 (3H, s), 3.7–3.8 (1H, m), 4.0–4.1 (1H, m), 4.06 (3H, s), 4.44 (1H, d, J=12.7 Hz), 5.04 (1H, d, J=4.9 Hz), 5.17 (1H, d, J=11.7 Hz), 5.22 (1H, d, J=11.7 Hz), 5.92 (1H, dd, J=4.9, 8.8 Hz), 6.8–7.3 (20H, m), 7.41 (1H, s), 8.37 (1H, s).

EXAMPLE 98

Sodium 7β-[(Z)-2-(2-aminothiazole-4-yl)-2-methoxyiminoacetamido]-3-(3-bromo-6,7-dihydroxy-4-oxo-4H-1-benzothiopyran-2-yl) thiomethyl-3-cephem-4-carboxylate

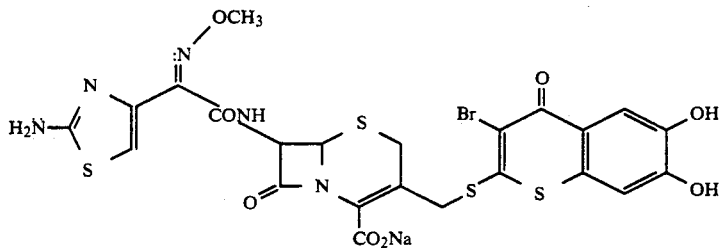

Similarly to Example 4, 94.3 mg (0.131 mmol) of title compound were obtained from 204 mg (0.162 mmol) of the compound of Example 97 (yield 81%).

$^1$H - NMR (400 MHz, CD$_3$OD, δ): 3.45 (1H, d, J=17.3 Hz), 3.78 (1H, d, J=17.3 Hz), 3.97 (3H, s), 4.14 (1H, d, J=12.2 Hz), 4.59 (1H, d, J=12.2 Hz), 5.11 (1H, d, J=4.9 Hz), 5.78 (1H, d, J=4.9 Hz), 6.68 (1H, s), 6.84 (1H, s), 7.60 (1H, s).

IR (KBr, cm$^{-1}$): 1750, 1620.

EXAMPLE 99 p-Methoxybenzyl 3-(3-bromo-6,7-di-tert-butoxycarbonyloxy-4-oxo-4H-1-benzothiopyran-2-yl)thiomethyl-7-[(Z)-2-tertbutoxycarbonylmethoxyimino-2-(2-tritylaminothiazole-4-yl)-acetamido]-3-cephem-4-carboxylate

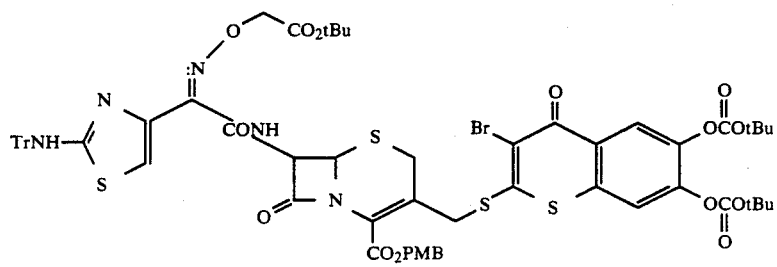

Similarly to Example 97, 262 mg (0.192 mmol) of title compound were obtained from 301 mg (0.336 mmol) of p-methoxybenzyl 7-[(Z)-2-tert-butoxycarbonylmethoxyimino-2-(2-tritylaminothiazole-4-yl) acetamido]-3-chloromethyl-3-cephem-4-carboxylate (yield 57%).

$^1$H - NMR (400 MHz, CDCl$_3$, δ): 1.45 (9H, s), 1.57 (18H, s), 3.44 (1H, d, J=18.1 Hz), 3.67 (1H, d, J=18.1 Hz), 3.71 (3H, s), 4.10 (1H, d, J=12.2 Hz), 4.32 (1H, d, J=12.2 Hz), 4.73 (1H, d, J=17.1 Hz), 4.79 (1H, d, J=17.1 Hz), 5.04 (1H, d, J=4.9 Hz), 5.20 (1H, d, J=11.7 Hz), 5.25 (1H, d, J=11.7 Hz), 5.90 (1H, dd, J=4.9, 8.8 Hz), 6.8–7.3 (20H, m), 7.43 (1H, s), 8.37 (1H, s).

EXAMPLE 100

Disodium 7β-[(Z)-2-(2-aminothiazole-4-yl)-2-carboxymethoxyiminoacetamido]-3-(3-bromo-6,7-dihydroxy-4-oxo-4H-1-benzothiopyran-2-yl)thiomethyl-3-cephem-4-carboxylate.

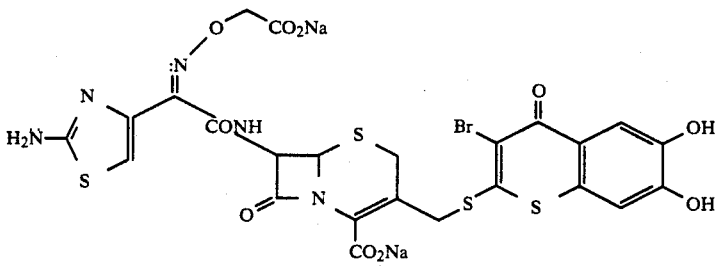

Similarly to Example 4, 113 mg (0.146 mmol) of title compound were obtained from 260 mg (0.191 mmol) of the compound of Example 99 (yield 77%).

$^1$H - NMR (400 MHz, CD$_3$OD, δ): 3.46 (1H, d, J=17.8 Hz), 3.78 (1H, d, J=17.8 Hz), 4.12 (1H, d, J=12.2 Hz), 4.54 (2H, s), 4.69 (1H, d, J=12.2 Hz), 5.12 (1H, d, J=4.9 Hz), 5.76 (1H, d, J=4.9 Hz), 6.68 (1H, s), 6.89 (1H, s), 7.59 (1H, s).

IR (KBr, cm$^{-1}$): 1750, 1600.

EXAMPLE 101

3-cyano-2-methylsulfinyl-4-oxo-4H-1-benzothiopyran

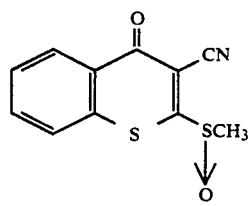

Similarly to Example 18, 106 mg (0.423 mmol) of title compound were obtained from 100 mg (0.429 mmol) of 3-cyano-2-methylthio-4-oxo-4H-3-benzothiopyran (W. D. Rudorf, Tetrahedron, 34, 725 (1978))(yield 99%).

$^1$H - NMR (400 MHz, d$_6$DMSO, δ): 3.14 (3H, s), 7.81 (1H, dd, J=7.3, 7.8 Hz), 7.93 (1H, dd, J=7.3, 8.3 Hz), 8.23 (1H, d, J=8.3 Hz), 8.40 (1H, d, J=7.8 Hz).

MS (M/Z): 249 (M$^+$).

EXAMPLE 102

3-cyano-2-mercapto-4-oxo-4H-1-benzothiapyran

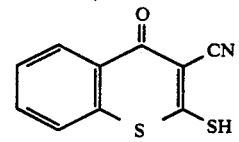

Similarly to Example 19, 70.0 mg (0.319 mmol) of title compound were obtained from 92.9 mg (0.373 mmol) of the compound of Example 101 (yield 86%).

$^1$H - NMR (400 MHz, d$_6$DMSO, δ): 7.3–7.5 (2H, m), 7.54 (1H, dd, J=7.3, 7.8 Hz), 8.13 (1H, d, J=7.8 Hz).

MS (M/Z): 219 (M$^+$).

EXAMPLE 103 p-Methoxybenzyl 3-(3-cyano-4-oxo-4H-1-benzothiopyran-2-yl-thiomethyl-7-[(Z)-2-methoxyimino-2-(2-tritylaminothiazole-4-yl) acetamido]-3-cephem-4-carboxylate

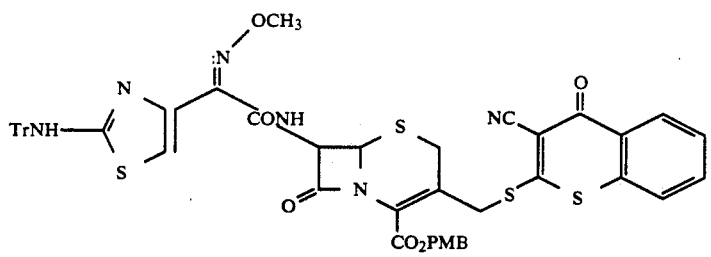

Similarly to Example 20, 276 mg (0.282 mmol) of title compound were obtained from 300 mg (0.378 mmol) of p-methoxybenzyl 3-chloromethyl-7-[(Z)-2-methoxyimino-2-(2-tritylaminothiazole-4-yl) acetamido]-3-cephem-4-carboxylate and 91.1 mg (0.416 mmol) of the compound of Example 102 (yield 75%).

$^1$H - NMR (400 MHz, CDCl$_3$, δ): 3.44 (1H, d, J=18.1 Hz), 3.74 (3H, s), 3.79 (1H, d, J=18.1 Hz), 4.08 (3H, s), 4.19 (1H, d, J=12.7 Hz), 4.58 (1H, d, J-12.7 Hz), 5.07 (1H, d, J=4.9 Hz), 5.16 (1H, d, J=11.7 Hz), 5.20 (1H, d, J=11.7 Hz), 5.93 (1H, dd, J=4.9, 8.8 Hz), 6.8–7.6 (24H, m).

EXAMPLE 104

Sodium 7β-[(Z)-2-(2-aminothiazole-4-yl)-2-methoxyiminoacetamido]-3-(3-cyano-4-oxo-4H-1-benzothiopyran-2-yl)-thiomethyl-3-cephem-4-carboxylate

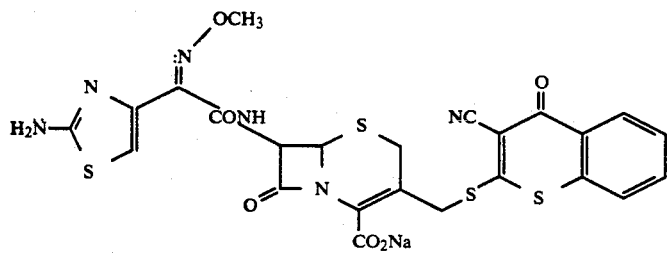

Similarly to Example 4, 63.6 mg (0.0999 mmol) of title compound were obtained from 269 mg (0.275 mmol) of the compound of Example 103 (yield 36%).

$^1$H - NMR (400 MHz, CD$_3$OD, δ): 3.45 (1H, d, J=17.6Hz), 3.82 (1H, d, J=17.6 Hz), 3.97 (3H, s), 4.22 (1H, d, J=13.7 Hz), 5.04 (1H, d, J=13.7 Hz), 5.12 (1H, d, J=4.9 Hz), 5.78 (1H, d, J - 4.9 Hz), 6.83 (1H, s), 7.3–8.4 (4H, m).

SIMS (M/Z): 637 (M+1)+.

IR (KBr, cm$^{-1}$): 1750, 1600.

EXAMPLE 105 p-Methoxybenzyl 3-(3-cyano-4-oxo-4H-1-benzothiopyran-2-yl)thiomethyl-7-[(Z)-2-(2-tritylaminothiozole-4-yl)-2-trityloxyiminoacetamido]-3-cephem-4-carboxylate

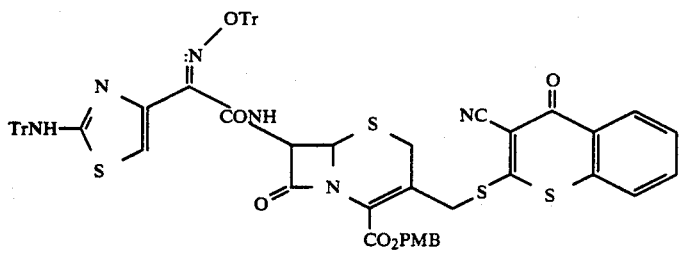

Similarly to Example 20, 200 mg (0.166 mmol) of title compound were obtained from 386 mg (0.378 mmol) of p-methoxybenzyl 3-chloromethyl-7-[(Z)-2-(2-tritylaminothiazole-4-yl)-2-trityloxyiminoacetamido]-3-cephem-4-carboxylate and 91.1 mg (0.416 mmol) of the compound of Example 102 (yield 44%).

$^1$H - NMR (400 MHz, CDCl$_3$, δ): 3.25 (1H, d, J=18.1 Hz), 3.67 (1H, d, J=18.1 Hz), 3.74 (3H, s), 4.1–4.2 (1H, m), 4.60 (1H, d, J=13.2 Hz), 5.06 (1H, d, J=4.9 Hz), 5.19 (1H, d, J=11.7 Hz), 5.23 (1H, d, J=11.7 Hz), 6.05 (1H, dd, J=4.9, 8.8 Hz), 6.8–7.7 (39H, m).

EXAMPLE 106

Sodium 7β-[(Z)-2-(2-aminothiazole-4-yl)-2-hydroxyiminoacetamido]-3-(3-cyano-4-oxo-4H-1-benzothiopyran-2-yl)thiomethyl-3-cephem-4-carboxylate

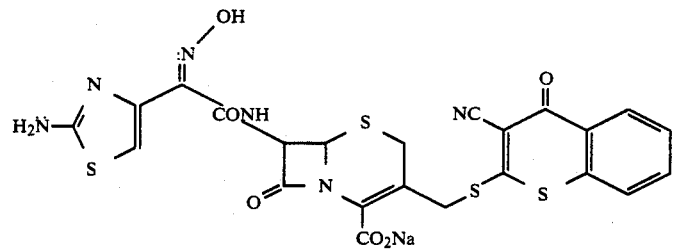

Similarly to Example 4, 52.8 mg (0.0848 mmol) of title compound were obtained from 196 mg (0.162 mmol) of the compound of Example 105 (yield 52%)

$^1$H - NMR (400 MHz, CDCl$_3$, δ): 3.43 (1H, d, J=17.6 Hz), 3.81 (1H, d, J=17.6 Hz), 4.21 (1H, d, J=13.7 Hz), 5.05 (1H, d, J=13.7 Hz), 5.13 (1H, d, J=4.9 Hz), 5.81 (1H, d, J=4.9 Hz), 6.77 (1H, s), 7.3–8.4 (4H, m).

SIMS (M/Z): 623 (M+1)+.

IR (KBr, cm$^{-1}$): 1760, 1600.

EXAMPLE 107 p-Methoxybenzyl
7-[(Z)-2-tert-butoxycarbonylmethoxyimino-
2-(2-tritylaminothiazole-4-yl)acetamido]-3-(6,7-di-tert-
butoxycarbonyloxy-4-oxo-4H-1-benzothiopyran-2-
yl)thiomethyl-3-cephem-4carboxylate

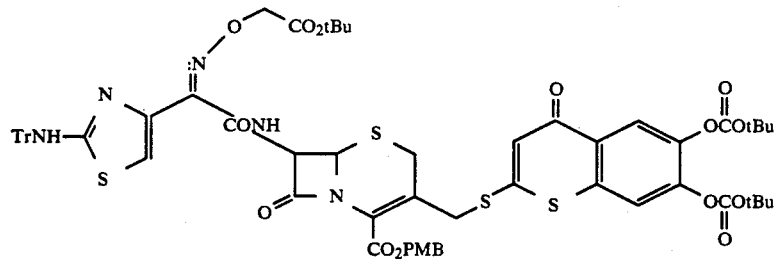

Similarly to Example 20, 230 mg (0.179 mmol) of title compound were obtained from 262 mg (0.293 mmol) of p-methoxybenzyl 7-[(Z)-2-tert-butoxycarbonylmethoxyimino-2-(2-tritylaminothiazole-4-yl)acetamido]-3-chloromethyl-3-cephem-4-carboxylate and 138 mg (0.323 mmol) of the compound of Example 72 (yield 61%).

$^1$H - NMR (400 MHz, CDCl$_3$, δ): 1.43 (9H, s), 1.56 (18H, s), 3.38 (1H, d, J=18.3 Hz), 3.63 (1H, d, J=18.3 Hz), 3.77 (3H, s) 4.02 (1H, d, J=13.2 Hz), 4.32 (1H, d, J=13.2 Hz), 4.72 (1H, d, J=17.1 Hz), 4.78 (1H, d, J=17.1 Hz), 5.01 (1H, d, J=4.9 Hz), 5.15 (1H, d, J=12.0 Hz), 5.21 (1H, d, J=12.0 Hz), 5.86 (1H, dd, J=4.9, 8.3 Hz), 6.8–7.4 (22H, m), 8.33 (1H, S).

EXAMPLE 108

Disodium
7β-[(Z)-2-(2-aminothiazole-4-yl)-2-carboxymethox-
yiminoacetamido]-3-(6,7-dihydroxy-4-oxo-4H-1-benzo-
thiopyran-2-yl)thiomethyl-3-cephem-4-carboxylate

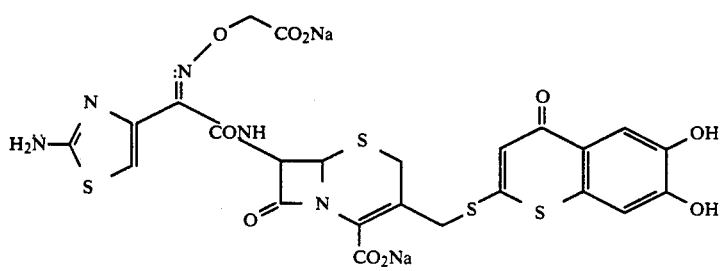

Similarly to Example 4, 84.0 mg (0.118 mmol) of title compound were obtained from 230 mg (0.179 mmol) of the compound of Example 107 (yield 66%)

$^1$H - NMR (400 MHz, CD$_3$OD, δ): 3.42 (1H, d, J=17.3 Hz), 3.74 (1H, d, J=17.3 Hz), 4.05 (1H, d, J=13.7 Hz), 4.54 (2H, s), 4.72 (1H, d, J=13.7 Hz), 5.07 (1H, d, J=4.9 Hz), 5.74 (1H, d, J=4.9 Hz), 6.87 (1H, s), 6.96 (1H, s), 7.05 (1H, s), 7.73 (1H, s).

IR (KBr, cm$^{-1}$): 1760, 1580.

EXAMPLE 109 p-Methoxybenzyl
7-[(Z)-2-(1-tert-butoxycarbonyl-1-methylethoxy)-
imino-2-(2-tritylaminothiazole-4-yl)acetamido]-3-(6,7-
di-tert-butoxycarbonyloxy-4-oxo-4H-1-benzothiopy-
ran-2-yl)thiomethyl-3-cephem-4-carboxylate

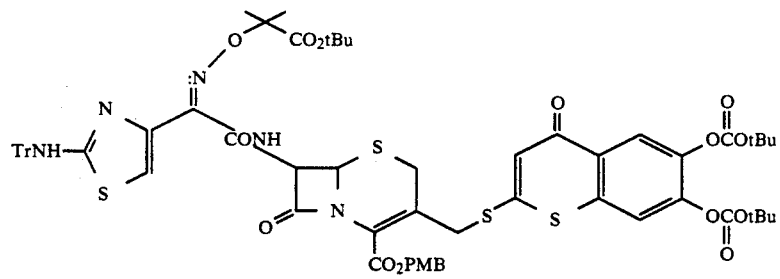

Similarly to Example 20, 239 mg (0.182 mmol) of title compound were obtained from 232 mg (0.752 mmol) of p-methoxybenzyl 7-[(Z)-2-(1-tert-butoxycarbonyl-1-methylethoxyimino)-2-(2-tritylaminothiazole-4-yl)acetamido]-3-chloromethyl-3-cephem-4-carboxylate and 118 mg (0.277 mmol) of the compound of Example 72 (yield 72%).

$^1$H - NMR (400 MHz, CDCl$_3$, δ): 1.42 (9H, s), 1.56 (18H, s), 1.58 (3H, s), 1.62 (3H, s), 3.38 (1H, d, J=18.1 Hz), 3.65 (1H, d, J=18.1 Hz), 3.77 (3H, s), 4.00 (1H, d, J=12.9 Hz), 4.37 (1H, d, J=12.9 Hz), 5.00 (1H, d, J=4.9 Hz), 5.16 (1H, d, J=11.7 Hz), 5.20 (1H, d,

J=11.7 Hz), 5.96 (1H, dd, J=4.9, 8.8 Hz), 6.7–7.4 (22H, m), 8.33 (1H, s).

EXAMPLE 110

Disodium 7β-[(Z)-2-(2-aminothiazole-4-yl)-2-(1-carboxy-1-methylethoxy)iminoacetamido]-3-(6,7-dihydroxy-4-oxo-4H-1-benzothiopyran-2-yl)thiomethyl-3-cephem-4-carboxylate

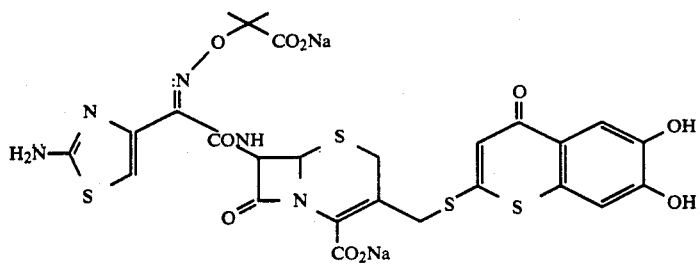

Similarly to Example 4, 35.1 mg (0.0476 mmol) of title compound were obtained from 120 mg (0.0914 mmol) of the compound of Example 109 (yield 52%).

$^1$H - NMR (400 MHz, CD$_3$OD, δ): 1.52 (3H, s), 1.55 (3H, s), 3.43 (1H, d, J=17.6 Hz), 3.74 (1H, d, J=17.6 Hz), 4.06 (1H, d, J=13.2 Hz), 4.63 (1H, d, J=13.2 Hz), 5.08 (1H, d, J=4.9 Hz), 5.75 (1H, d, J=4.9 Hz), 6.81 (1H, s), 6.82 (1H, s), 6.92 (1H, s), 7.63 (1H, s),

IR(KBr, cm$^{-1}$): 1760, 1580.

EXAMPLE 111

3-Ethoxycarbonyl-2-methylthio-4-oxo-6,7,8-trifluoro-4H-1-benzothiopyran

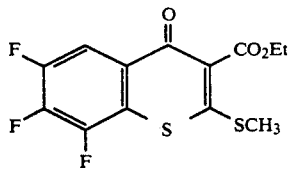

To a solution of 3.00 g (11.4 mmol) of ethyl 2,3,4,5-tetrafluorobenzoylacetate, 870 mg (11.4 mmol) of carbon disulfide and 9 ml of dried dimethyl sulfoxide were added 2.31 g (22.8 mmol) of triethylamine at room temperature, and the mixture was stirred for 1 hour at room temperature. Then, at room temperature, 3.24 g (22.8 mmol) of methyl iodide were added and the mixture was stirred for 2 hours, which was poured into ice-water. The crystals deposited were collected by filtration and dried to obtain 2.81 g (8.41 mmol) of title compound (yield 74%.

Melting point: 113°–115° C.

$^1$H - NMR (90 MHz, CDCl$_3$, δ): 1.40 (3H, t, J=7.0 Hz), 2.71 (3H, s), 4.44 (2H, q, J=7.0 Hz), 8.11 (1H, ddd, J=2.2, 7.5, 10.3 Hz).

Elemental analysis (%): As C$_{13}$H$_9$F$_3$O$_3$S$_2$; Calculated C: 46.70; H:2.71; Observed C: 46.66; H: 2.69

EXAMPLE 112

3-Carboxy-2-methylthio-4-oxo-6,7,8-trifluoro-4H-1-benzothiopyran

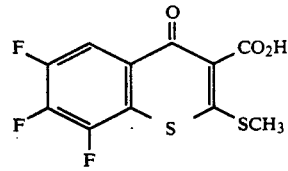

A mixture of 300 mg (0.897 mmol) of the compound of Example 111, 0.54 ml of acetic acid, 0.072 ml of concentrated sulfuric acid and 0.36 ml of water was stirred for 3 hours at 100° C. After cooling by allowing to stand, the crystals deposited were collected by filtration, washed with water, and dried to obtain 147 mg (0.481 mmol) of title compound (yield 54%).

$^1$H - NMR (90 MHz, d$_6$DMSO, δ): 2.77 (3H, s), 8.12 (1H, ddd, J=2.2, 7.5, 10.8 Hz).

MS (M/Z): 306 (M+).

EXAMPLE 113

3-(4-Methoxybenzyloxycarbonyl)-2-methylthio-4-oxo-6,7,8-trifluoro-4H-1-benzothiopyran

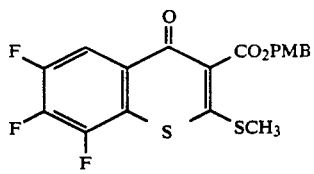

To a suspension of 50 mg (0.163 mmol) of the compound of Example 112 in 0.2 ml of chloroform were added 30.7 mg (0.196 mmol) of p-methoxybenzyl chloride, 16.5 mg (0.163 mmol) of triethylamine and 29.4 mg (0.196 mmol) of sodium iodide, and the mixture was stirred for 5 hours at room temperature, which was poured into ice-water and extracted with dichloromethane. The organic layer was washed with water and with saturated saline solution, dried over anhydrous sodium sulfate and concentrated. The residue was purified by means of silica gel column chromatography (CHCl$_3$) to obtain 22.5 mg (0.0528 mmol) of title compound (yield 32%).

$^1$H - NMR (400 MHz, CDCl$_3$, δ): 2.66 (3H, s), 3.81 (3H, s), 5.34 (2H, s), 6.90 (2H, d, J=8.6 Hz), 7.40 (2H, d, J=8.6 Hz), 8.12 (1H, ddd, J=2.2, 7.6, 10.0 Hz).

EXAMPLE 114

3-(4-Methoxybenzylcarbonyl)-2-methylsulfinyl-4-oxo-6,7,8-trifluoro-4-oxo-4H-1-benzothiopyran

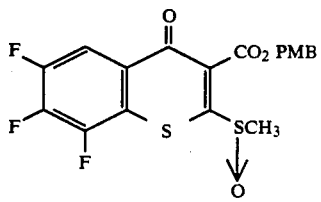

Similarly to Example 18, 53.7 mg (0.121 mmol) of title compound were obtained from 55.8 mg (0.131 mmol) of the compound of Example 113 (yield 93%).

$^1$H - NMR (400 MHz, CDCl$_3$, δ): 3.00 (3H, s), 3.82 (3H, s), 5.31 (1H, d, J=11.5 Hz), 5.37 (1H, d, J=11.5 Hz), 6.92 (2H, d, J=8.8 Hz), 7.39 (2H, d, J=8.8 Hz), 8.15 (1H, ddd, J=2.4, 7.5, 9.9 Hz).

EXAMPLE 115

2-Mercapto-3-(4-methoxybenzyloxycarbonyl-4-oxo-6,7,8-trifluoro-4H-1-benzothiopyran

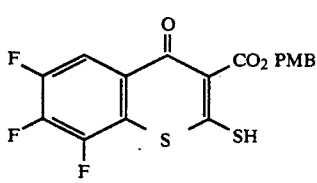

Similarly to Example 19, 40.2 mg (0.0975 mmol) of title compound were obtained from 53.7 mg (0.121 mmol) of the compound of Example 114 (yield 80%).

$^1$H - NMR (400 MHz, CDCl$_3$, 67): 3.81 (3H, s), 5.41 (2H, s), 6.91 (2H, d, J=8.8 Hz), 7.42 (2H, d, J=8.8 Hz), 7.9-8.0 (1H, m).

EXAMPLE 116 p-Methoxybenzyl 3-[3-(4-methoxybenzyloxycarbonyl)-4-oxo-6,7,8-trifluoro-4H-1-benzothiopyran-2-yl]thiomethyl-7-[(Z)-2-methoxyimino-2-(2-tritylaminothiazole-4-yl)acetamido] -3-cephem-4-carboxylate

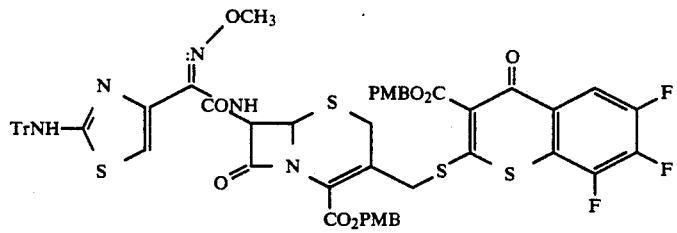

Similarly to Example 20, 139 mg (0.119 mmol) of title compound were obtained from 157 mg (0.198 mmol) of p-methoxybenzyl 3-chloromethyl-7-[(Z)-2-methoxyimino-2-(2-tritylaminothiazole-4-yl)acetamido]-3-cephem-4-carboxylate and 89.7 mg (0.218 mmol) of the compound of Example 115 (yield 60%).

$^1$H - NMR (400 MHz, CDCl$_3$,δ): 3.14 (1H, d, J=18.3 Hz), 3.52 (1H, d, J=18.3 Hz), 3.76 (3H, s), 3.77 (3H, s), 3.84 (1H, d, J=13.7 Hz), 4.07 (3H, s), 4.45 (1H, d, J=13.7 Hz), 4.95 (1H, d, J=4.9 Hz), 5.06 (1H, d, J=12.0 Hz), 5.12 (1H, d, J=12.0 Hz), 5.32 (2H, s), 5.85 (1H, dd, J=4.9, 9.0 Hz), 6.8-7.4 (24H, m), 8.0-8.1 (1H, m),

EXAMPLE 117

Sodium 7β-[(Z)-2-(2-aminothiazole-4-yl)-2-methoxyiminoacetamido]-3-(3-carboxy-4-oxo-6,7,8-trifluoro-4H-1-benzothiopyran-2-yl)thiomethyl-3-cephem-4-carboxylate

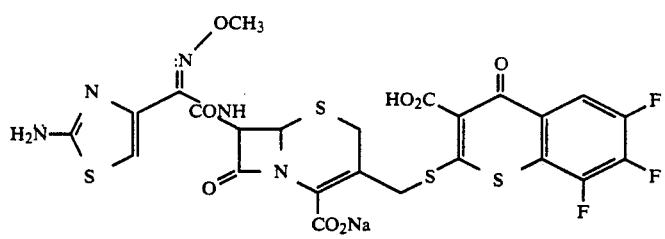

Similarly to Example 4, 64.1 mg (0.0903 mmol) of title compound were obtained from 139 mg (0.119 mmol) of the compound of Example 116 (yield 76%).

$^1$H - NMR (400 MHz, CD$_3$OD, δ): 3.46 (1H, d, J=17.6 Hz), 3.86 (1H, d, J=17.6 Hz), 3.96 (3H, s), 4.09 (1H, d, J=12.7 Hz), 4.68 (1H, d, J=12.7 Hz), 5.11 (1H, d, J=4.9 Hz), 5.74 (1H, d, J=4.9 Hz), 6.83 (1H, s), 8.0-8.2 (1H, m),.

IR (KBr, cm$^{-1}$): 1760, 1600.

EXAMPLE 118

P-Methoxybenzyl 3-[3-(4-methoxybenzyloxycarbonyl)-4-oxo-6,7,8-trifluoro-4H-1-benzothiopyran-2-yl]thiomethyl-7-[(Z)-2-(2-tritylaminothiazole-4-yl)-2-trityloxyiminoacetamido]-3-cephem-4-carboxylate

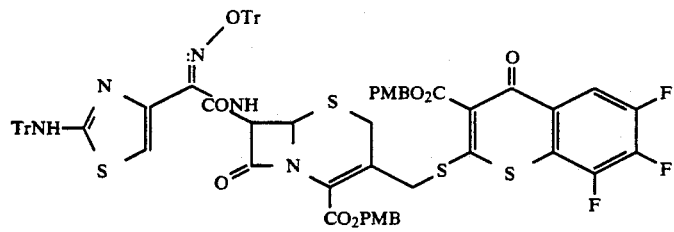

Similarly to Example 20, 163 mg (0.116 mmol) of title compound were obtained from 209 mg (0.204 mmol) of p-methoxybenzyl 3-chloromethyl-7-[(Z)-2-(2-tritylaminothiazole-4-yl)-2-trityloxyiminoacetamide]-3-cephem-4-carboxylate and 92.5 mg (0.224 mmol) of the compound of Example 115 (yield 57%).

$^1$H - NMR (400 MHz, CDCl$_3$, δ): 3.00 (1H, d, J=18.6 Hz), 3.46 (1H, d, J=18.6 Hz), 3.69 (3H, s), 3.78 (3H, s), 3.8-3.9 (1H, m), 4.44 (1H, d, J=13.2 Hz), 4.97 (1H, d, J=4.9 Hz), 5.09 (1H, d, J=11.7 Hz), 5.18 (1H, d, J=11.7 Hz), 5.30 (2H, d, J=2.9 Hz), 6.00 (1H, dd, J=4.9, 9.0 Hz), 6.8-7.4 (39H, m), 8.0-8.1 (1H, m).

EXAMPLE 119

Sodium 7β-[(Z)-2-(2-aminothiazole-4-yl)-2-hydroxyiminoacetamido]-3-(3-carboxy-4-oxo-6,7,8-trifluoro-4H-1-benzothiopyran-2-yl)thiomethyl-3-cephem-4-carboxylate

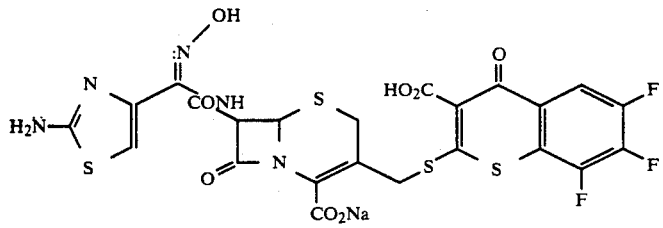

Similarly to Example 4, 50.3 mg (0.0723 mmol) of title compound were obtained from 160 mg (0.115 mmol) of the compound of Example 118 (yield 63%).

$^1$H - NMR (400 MHz, CD$_3$OD, δ): 3.46 (1H, d, J=17.6 Hz), 3.86 (1H, d, J=17.6 Hz), 4.10 (1H, d, J=12.7 Hz), 4.67 (1H, d, J=12.7 Hz), 5.13 (1H, d, J=4.9 Hz), 5.77 (1H, d, J=4.9 Hz), 6.77 (1H, s), 8.0-8.2 (1H, m).

IR (KBr, cm$^{-1}$): 1760, 1600.

EXAMPLE 120

2,3-Dibromo-4,5-dimethoxybenzaldehyde

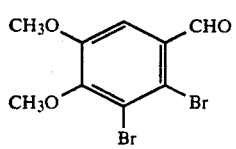

Similarly to Example 79, 8.30 g (25.6 mmol) of title compound were obtained from 9.99 g (32.2 mmol) of 5,6-dibromovanillin (Isao Kubo et al., Journal of Natural Products, 53, 50 (1990.)(yield 79%).

Melting point: 126°-127° C.

$^1$H - NMR (400 MHz, CDCl$_3$, δ): 3.93 (3H, s), 3.95 (3H, s), 7.49 (1H, s).

MS (M/Z) 322 (M+).

EXAMPLE 121

2,3-Dibromo-4,5-dimethoxyacetophenone

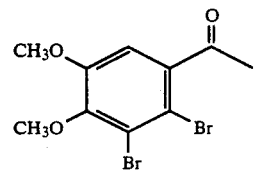

Similarly to Example 80, 4.52 g (13.4 mmol) of title compound were obtained from 8.30 g (25.6 mmol) of the compound of Example 120 (yield 52%).

$^1$H - NMR (400 MHz, CDCl$_3$, δ): 2.64 (3H, s), 3.88 (3H, s), 3.88 (3H, s), 6.91 (1H, s).

MS (M/Z) 336 (M+).

EXAMPLE 122

8-Bromo-6,7-dimethoxy-2-methylthio-4-oxo-4H-1-benzothiopyran

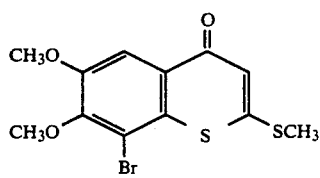

Similarly to Example 17, 2.52 g (7.26 mmol) of title compound were obtained from 3.00 g (8.88 mmol) of the compound of Example 121 (yield 82%).

$^1$H - NMR (400 MHz, CDCl$_3$, δ): 2.66 (3H, s), 3.98 (3H, s), 4.00 (3H, s), 6.85 (1H, s), 8.01 (1H, s),

MS (M/Z) 346 (M+).

EXAMPLE 123

8-Bromo-6,7-dihydroxy-2-methylthio-4-oxo-4H-1-benzothiopyran

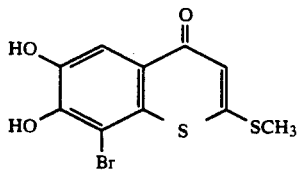

Similarly to Example 54, 2.28 g of title compound were obtained from 2.23 g (6.42 mmol) of the compound of Example 122.

$^1$H - NMR (400 MHz, d$_6$DMSO, δ): 2.69 (3H, s), 6.75 (1H, s), 7.76 (1H, s), MS (M/Z) 318 (M+).

EXAMPLE 124

8-Bromo-6,7-di-tert-butoxycarbonyloxy-2-methylthio-4-oxo-4H-1-benzothiopyran

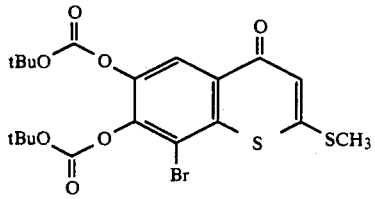

Similarly to Example 70, 2.43 g (4.68 mmol) of title compound were obtained from 1.98 g (6.19 mmol) of the compound of Example 123 (yield 76%).

$^1$H - NMR (400 MHz, CDCl$_3$, δ): 1.55 (9H, s), 1.57 (9H, s), 2.66 (3H, s), 6.83 (1H, s), 8.39 (1H, s).

EXAMPLE 125

8-Bromo-6,7-di-tert-butoxycarbonyloxy-2-methylsulfinyl-4-oxo-4H-1-benzothiopyran

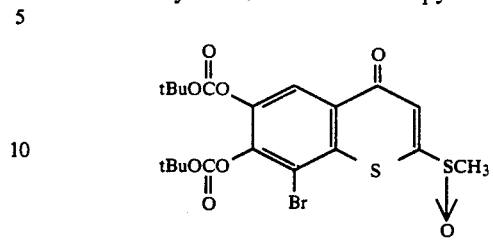

Similarly to Example 18, 1.96 g of title compound were obtained from 1.86 g (3.58 mmol) of the compound of Example 124.

$^1$H - NMR (400 MHz, CDCl$_3$, δ): 1.56 (9H, s), 1.58 (9H, s), 2.99 (3H, s), 7.28 (1H, s), 8.45 (1H, s).

EXAMPLE 126 p-Methoxybenzyl 3-(8-bromo-6,7-di-tert-butoxycarbonyloxy-4oxo-4H-1-benzothiopyran-2-yl)thiomethyl-7-[(Z)-2-methoxyimino-2-(2-tritylaminothiazole-4-yl)acetamido]-3-cephem-4-carboxylate

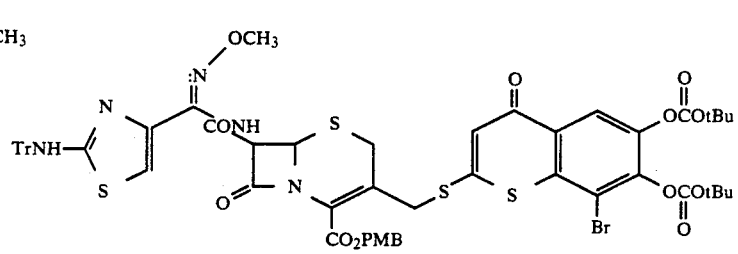

Similarly to Example 85, 307 mg (0.243 mmol) of title compound were obtained from 267 mg (0.336 mmol) of p-methoxybenzyl 3-chloromethyl-7-[(Z)-2-methoxyimino-2-(2-tritylaminothiazole-4-yl)acetamido]-3-cephem-4-carboxylate and 180 mg (0.336 mmol) of the compound of Example 125 (yield 72%).

$^1$H - NMR (400 MHz, CDCl$_3$, δ): 1.56 (9H, s), 1.57 (9H, s), 3.43 (1H, d, J=18.1 Hz), 3.70 (1H, d, J=18.1 Hz), 3.77 (3H, s), 4.0–4.1 (1H, m), 4.07 (3H, s), 4.36 (1H, d, J=13.2 Hz), 5.02 (1H, d, J=4.9 Hz), 5.13 (1H, d, J=11.7 Hz), 5.23 (1H, d, J=11.7 Hz), 5.90 (1H, dd, J=4.9, 8.6 Hz), 6.8–7.4 (21H, m), 8.38 (1H, s).

EXAMPLE 127

Sodium 7β-[(Z)-2-(2-aminothiazole-4-yl)-2-methoxyiminoacetamido]-3-(8-bromo-6,7-dihydroxy-4-oxo-4H-1-benzothiopyran-2-yl)thiomethyl-3-cephem-4-carboxylate

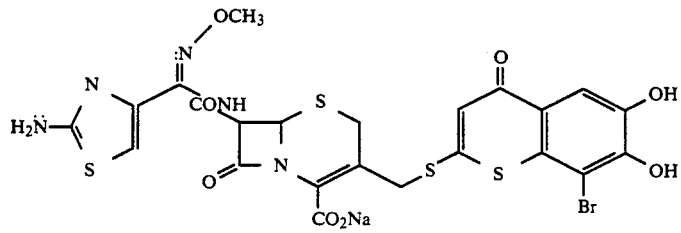

Similarly to Example 4, 130 mg (0.181 mmol) of title compound were obtained from 302 mg (0.239 mmol) of the compound of Example 126 (yield 75%).

$^1$H - NMR (400 MHz, CD$_3$OD, δ): 3.44 (1H, d, J=17.3 Hz), 3.75 (1H, d, J=17.3 Hz), 3.96 (3H, s), 4.17 (1H, d, J=12.7 Hz), 4.43 (1H, d, J=12.7 Hz), 5.10 (1H, d, J=4.9 Hz), 5.76 (1H, d, J=4.9 Hz), 6.83 (1H, s), 6.95 (1H, s), 7.63 (1H, s).

IR (KBr, cm$^{-1}$): 1760, 1600.

EXAMPLE 128 p-Methoxybenzyl 3-(8-bromo-6,7-di-tert-butoxycarbonyloxy-4-oxo-4H-1-benzothiopyran-2-yl)thiomethyl-7-[(Z)-2-tertbutoxycarbonylmethoxyimino-2-(2-tritylaminothiazole-4-yl)acetamido]-3-cephem-4-carboxylate

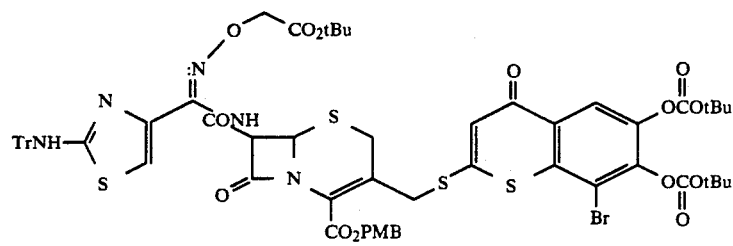

Similarly to Example 85, 291 mg (0.213 mmol) of title compound were obtained from 227 mg (0.254 mmol) of p-methoxybenzyl 7-[(Z)-2-tert-butoxycarbonyl methoxyimino-2-(2-tritylaminothiazole-4-yl)acetamido]-3-chloromethyl-3-cephem-4-carboxylate and 136 mg (0.254 mmol) of the compound of EXAMPLE 125 (yield 84%).

$^1$H - NMR (400 MHz, CDCl$_3$, δ): 1.44 (9H, s), 1.56 (9H, s), 1.57 (9H, s), 3.40 (1H, d, J=18.1 Hz), 3.65 (1H, d, J=18.1 Hz), 3.77 (3H, s), 4.06 (1H, d, J=12.7 Hz), 4.35 (1H, d, J=12.7 Hz), 4.7–4.8 (2H, m), 5.02 (1H, d, J=4.9 Hz), 5.15 (1H, d, J=11.7 Hz), 5.22 (1H, d, J=11.7 Hz), 5.8–5.9 (1H, m), 6.8–7.4 (21H, m), 8.38 (1H, s).

EXAMPLE 129

Disodium 7β-[(Z)-2-(2-aminothiazole-4-yl)-2-carboxymethoxyiminoacetamido]-3-(8-bromo-6,7-dihydroxy-4-oxo-4H-1-benzothiopyran-2-yl)thiomethyl-3-cephem-4-carboxylate

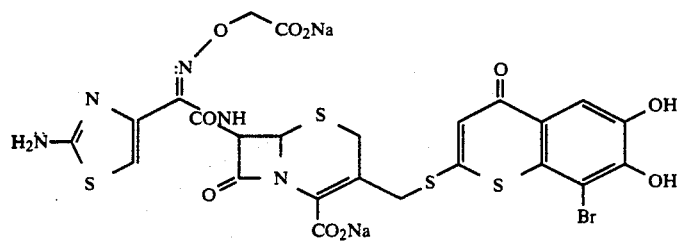

Similarly to Example 4, 117 mg (0.148 mmol) of title compound were obtained from 288 mg (0.211 mmol) of the compound of Example 128 (yield 70%).

$^1$H - NMR (400 MHz, CD$_3$OD, δ): 3.44 (1H, d, J=17.6 Hz), 3.75 (1H, d, J=17.6 Hz), 4.12 (1H, d, J=12.7 Hz), 4.53 (2H, s), 4.33 (1H, d, J=12.7 Hz), 5.10 (1H, d, J=4.9 Hz), 5.73 (1H, d, J=4.9 Hz), 6.87 (1H, s), 6.93 (1H, s), 7.62 (1H, s).

IR (KBr, cm$^{-1}$): 1760, 1600.

EXAMPLE 130

6,7-Dimethoxy-2-methylthio-4-oxo-4H-1-benzothiopyran

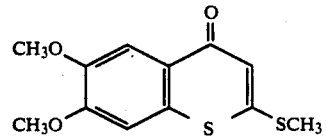

Similarly to Example 17, 802 mg (2.99 mmol) of title compound were obtained from 1.00 g (3.86 mmol) of 2-bromo-4,5-dimethoxyacetophenone (Edward McDonald and Paul Smith, J.C.S. Perkin I, 837 (1980).)(yield 77%).

Melting point: 161°–162° C.

Elemental analysis (%): As C$_{12}$H$_{12}$O$_3$S$_2$; Calculated C: 53.70; H: 4.51; Observed C: 53.60; H: 4.37.

The spectral data of this compound were consistent with those of the compound of Example 48.

EXAMPLE 131

6,7-Dihydroxy-2-methylthio-4-oxo-4H-1-benzothiopyran

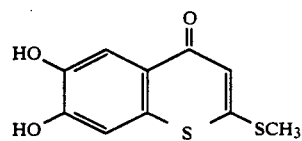

Similarly to Example 54, 6.81 g (28.3 mmol) of title compound were obtained from 33.6 g (133 mmol) of the compound of Example 61 (yield 21%).

Melting point: 164°–166° C.

The spectral data of this compound were consistent with those of the compound of Example 54.

What is claimed is:

1. A cephem compound represented by formula or a pharmacologically acceptable salt or ester thereof:

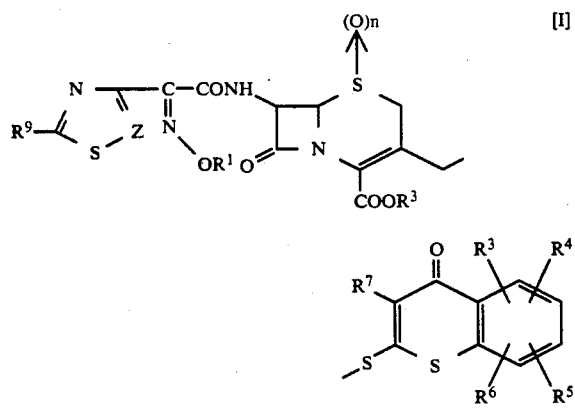

wherein $R^1$ indicates a straight-chain or branched lower alkyl group which may be substituted by a carboxyl group or a protected carboxyl group, trityl group, hydrogen atom or fluorine-substituted lower alkyl group, $R^2$ indicates a hydrogen atom, metal atom or a carboxyl-protective group, $R^3$, $R^4$, $R^5$ and $R^6$, which may be identical or different, indicate hydrogen atoms, halogen atoms, straight-chain or branched lower alkyl groups which may be substituted with alkoxy, halogen, hydroxyl, protected hydroxyl, amino, alkylamino or acyl, mercapto groups which may be substituted with alkyl, phenyl, 4-methyl-1,2,4-triazole-3-yl or 1-methyltetrazole-5-yl, lower alkylamino groups, hydroxyl groups which may be protected, lower alkoxy groups, lower alkanoyl groups, lower alkoxycarbonyl groups or lower alkylenedioxy group which may be substituted with alkyl, $R^7$ indicates a hydrogen atom, cyano group, halogen atom or $COOR^8$ where $R^8$ is hydrogen or lower alkyl group, $R^9$ indicates an amino group which may be protected, Z indicates N or CH, and n indicates 0 or 1.

2. An antibacterial pharmaceutical composition comprising an effective amount of the compound of claim 1 in admixture with a pharmacologically acceptable carrier or excipient.

3. A method of treating bacterial infection in a subject which comprises administering to the subject an effective amount of the compound of claim 1.

* * * * *